(12) United States Patent
LaVoie et al.

(10) Patent No.: US 8,729,060 B2
(45) Date of Patent: May 20, 2014

(54) MACROCYCLIC POLYOXAZOLE COMPOUNDS AND USE THEREOF

(75) Inventors: Edmond J. LaVoie, New Brunswick, NJ (US); Joseph E. Rice, New Brunswick, NJ (US); Satyanarayana Mavurapu, New Brunswick, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 820 days.

(21) Appl. No.: 12/671,893

(22) PCT Filed: Aug. 1, 2008

(86) PCT No.: PCT/US2008/072023
§ 371 (c)(1),
(2), (4) Date: Feb. 2, 2010

(87) PCT Pub. No.: WO2009/018549
PCT Pub. Date: Feb. 5, 2009

(65) Prior Publication Data
US 2011/0230531 A1   Sep. 22, 2011

Related U.S. Application Data

(60) Provisional application No. 60/953,660, filed on Aug. 2, 2007.

(51) Int. Cl.
*A61K 31/35* (2006.01)
*C07D 245/00* (2006.01)

(52) U.S. Cl.
USPC ...... 514/183; 514/460; 514/369; 514/254.02; 514/254.11; 514/375

(58) Field of Classification Search
CPC .... C07D 17/12; C07D 277/34; C07D 499/00; C07D 295/092; C07D 311/30; C07D 317/54
USPC ............... 514/183, 460, 369, 254.02, 254.11, 514/375, 456, 464, 652; 549/403, 434; 536/23.1; 540/546; 544/369, 376; 548/181, 183
See application file for complete search history.

(56) References Cited

U.S. PATENT DOCUMENTS

2009/0156627 A1   6/2009 Lavoie et al.

FOREIGN PATENT DOCUMENTS

EP           1350794 A1    10/2003
WO      WO 02/48153        6/2002
WO    WO 2009/018551       2/2009

OTHER PUBLICATIONS

Han et al., TiPS, 2000, 21, 136-142.*
Patent Cooperation Treaty, International Search Report and Written Opinion, PCT/US2008/072023, 9 pages, Jan. 19, 2009.
Barbieri, C.M. et al., "Defining the mode, energetic and specificity with which a macrocyclic hexaoxazole binds to human telomeric G-quadruplex DNA", *Nucleic Acids Res.*, 35(10), pp. 3272-3286, (2007) (Epub Apr. 22, 2007).
Binz, N. et al., "Telomerase inhibition, telomere shortening, cell growth suppression and induction of apoptosis by telomestatin in childhood neuroblastoma cells", *Eur. J. Cancer*, 41, pp. 2873-2881, (2005).
Chattopadhyay, S.K.et al., "Convergent synthesis of a 24-membered macrocyclic hexaoxazole derivative related to the novel telomerase inhibitor telomestatin", *Tetrahedron Letters*, 47(45), pp. 7897-7900, (2006).
Kim, M. et al., "The Different Biological Effects of Telomestatin and TMPyP4 Can Be Attributed to Their Selectivity for Interaction with Intramolecular or Intermolecular G-Quadruplex Structures", *Cancer Res.*, 63, pp. 3247-3256, (2003).
Kim, M. et al., "Telomestatin, a potent telomerase inhibitor that interacts quite specifically with the human telomeric intramolecular g-quadruplex", *J. Am. Chem. Soc.*, 124, pp. 2098-2099, (2002).
Liu, W. et al., "Binding of G-Quadruplex-Interactive Agents to Distinct G-Quadruplexes Induces Different Biological Effects in MiaPaCa Cells", *Nucleosides, Nucleotides, and Nucleic Acids*, 24, pp. 1801-1815, (2005).
Marson, C.M. et al., "Synthesis of the penta-oxazole core of telomestatin in a convergent approach to poly-oxazolemacrocycles", *Organic & Biomolecular Chemistry*, 4(21), pp. 3892-3893, (2006).
Minhas, G.S. et al., "Synthesis and G-quadruplex stabilizing properties of a series of oxazole-containing macrocycles", *Bioorganic & Medicinal Chemistry Letters*, 16, pp. 3891-3895, (2006).
Nakajima, A., et al., "Telomerase inhibition enhances apoptosis in human acute leukemia cells: possibility of antitelomerase therapy", *Leukemia.* 17, pp. 560-567, (2003).
Satyanarayana, M. et al., "Macrocyclic hexaoxazoles: Influence of aminoalkyl substituents on RNA and DNA G-quadruplex stabilization and cytotoxicity", *Bioorg. Med. Chem. Lett.*, vol. 20, pp. 3150-3154, (2010).
Satyanarayana, M. et al., "Ring-closing metathesis for the synthesis of a highly G-quadruplex selective macrocyclic hexaoxazole having enhanced cytotoxic potency", *Bioorg. Med. Chem. Lett.*, 18(13), pp. 3802-3804 (Jul. 1, 2008) (Epub May 15, 2008).

(Continued)

*Primary Examiner* — Savitha Rao
(74) *Attorney, Agent, or Firm* — Viksnins Harris & Padys PLLP

(57) ABSTRACT

The invention provides compounds of formula (I) wherein A, B, $R^1$, F, G, n, n' and the dotted line have any values defined herein, as well as salts thereof. The compounds have activity as anti-proliferative agents.

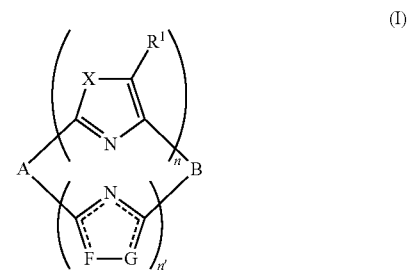

(I)

22 Claims, No Drawings

(56) References Cited

OTHER PUBLICATIONS

Shin-Ya, K. et al., "Telomestatin, a Novel Telomerase Inhibitor from *Streptomyces anulatus*", *J. Am. Chem. Soc.*, 123, pp. 1262-1263, (2001).

Sohda, K. et al., "YM-216391, a Novel Cytotoxic Cyclic Peptide from *Streptomyces nobilis*. I. Fermentation, Isolation and Biological Activities", *J. Antibiotics*, 58(1), pp. 27-31, (2005).

Sohda, K. et al., "YM-216391, a novel cytotoxic cyclic peptide from *Streptomyces nobilis*. II. Physico-chemical properties and structure elucidation", *J. Antibiot.* (Tokyo), 58(1), pp. 32-36, (Jan. 2005).

Tauchi, T. et al., "Activity of a novel G-quadruplex-interactive telomerase inhibitor, telomestatin (SOT-085), against human leukemia cells: involvement of ATM-dependent DNA damage response pathways", *Oncogene*, 22, pp. 5338-5347, (2003).

* cited by examiner

MACROCYCLIC POLYOXAZOLE COMPOUNDS AND USE THEREOF

PRIORITY OF INVENTION

This application claims priority from U.S. Provisional Application No. 60/953,660, filed 2 Aug. 2007, which application is incorporated by reference.

BACKGROUND OF THE INVENTION

A diverse array of compounds, including anthraquinones, acridines, cationic porphyrins, perylenes, thidium derivatives, fluorenones, pentacyclic acridinium salts, fluoroquinophenoxazines, and other specific miscellaneous polycyclic compounds, have been reported to stabilize G-quadruplex DNA. Most of these compounds have little or no selectivity for G-quadruplex vs. duplex DNA.

Telomestatin is a natural product isolated from *Streptomyces anulatus* 3533-SV4 (Shin-ya et al., *J. Am. Chem. Soc.*, 2001, 123, 1262-1263). At the time of its discovery, telomestatin was viewed as the most potent inhibitor of telomerase. In vitro, telomestatin stabilizes G-quadruplex vs. duplex DNA in a 70:1 ratio (Kim et al., *Cancer Res.*, 2003, 63, 3247-3256). It has been suggested that telomestatin also inhibits telomerase function in vivo, since cells treated with the natural product exhibit a cellular senescence phenotype. Like telomere dysfunction, telomestatin activates the ATM signaling pathway. While the precise mechanism by which telomestatin interacts with a G-quadruplex has not been definitively elucidated, telomestatin does suppress the plating efficiency of K62 leukemia cells but has a much lesser effect on burst-forming units—erythrocyte (BFU-E) and colony-forming units—granulocyte/macrophage (CFU-GM) from natural bone marrow CD34-positive cells (Tauchi et al., *Oncogene*, 2003, 22, 5338-5347).

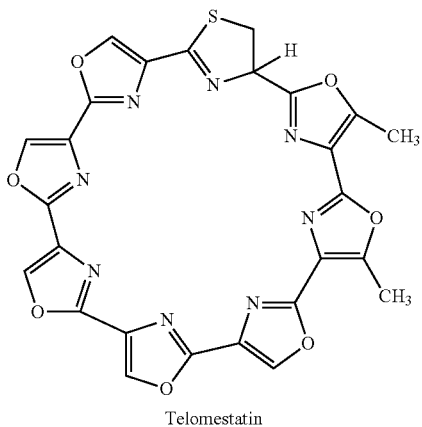 [SMILES: Cc1oc2nc1-c1nc(co1)-c1nc(co1)-c1nc(co1)-c1nc(co1)-c1nc(co1)C1=NC(CS1)c1nc-2c(C)o1]

Telomestatin

The anticancer potential of telomestatin resides in its telomerase inhibitory activity ($IC_{50}$ 5 nM) and in its ability to enhance apoptosis. Telomestatin has been evaluated for cytotoxicity in the human neuroblastoma cell lines SK-N-AS, LAN5, WAC2, and LAN1 with $IC_{50}$ values of 0.8, 2.5, 3.2, and 4.0 μM respectively (Binz et al., *Eur. J. Cancer*, 2005, 41, 2873-2881) and in the human pancreatic carcinoma MiaPaCa with an $IC_{50}$ value of 0.5 μM (Liu et al., *Nucleosides, Nucleotides, and Nucleic Acids*, 2005, 24, 1801-1815).

Another macrocyclic polyoxazole, YM-216391 isolated from *Streptomyces nobilis* is active against the human breast cancer cell lines HBC-4, BSY-1, HBC-5, MCF-7, and MDA-MB-231 with $GI_{50}$ values ranging from 15-33 nM (Sohda, K.-y., et al., *J. Antibiotics*, 2005, 58, 27-31 and Sohda, K.-y., et al., Hiramoto, M., Suzumura, K.-i., Takebayashi, Y., Suzuki, K.-i., Tanaka, A. *J. Antibiotics*, 2005, 58, 32-36).

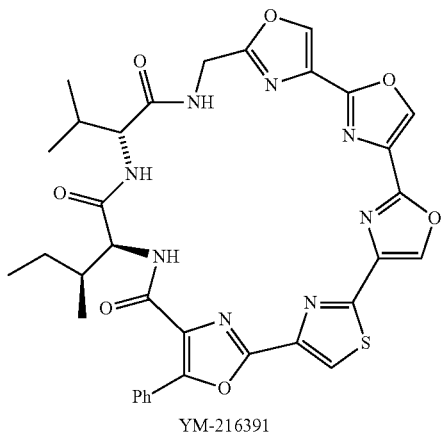

YM-216391

The mechanism of action of YM-216391 has not yet been elucidated.

Currently, there is a need for novel therapeutic agents and therapeutic methods that are useful for treating diseases such as cancer. Such agents may have improved binding affinity for G-quadruplex DNA and/or they may have advantageous drug-like properties.

SUMMARY OF THE INVENTION

The present invention provides compounds that possess anti-cancer properties. Accordingly there is provided a compound of the invention which is compound of formula (I):

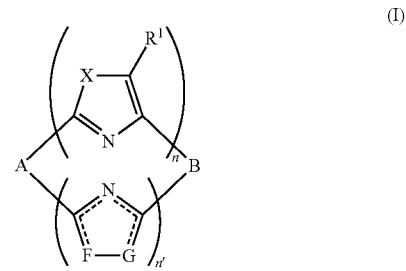

wherein:
one of A and B is —CH($R^b$)CH($R^c$)($R^d$)($R^e$)—;
and the other of A and B is:

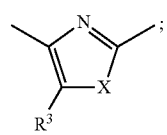

—CH($R^a$)NHC(=O)— or —CH($R^b'$)CH($R^{c'}$)C($R^{d'}$)($R^{e'}$)—;
one of F and G is X and the other is C($R^2$);
each X is independently NH, S, or O;

the dotted line in the ring containing F and G signifies that two double bonds are present in the ring, the positions of which depend upon the values selected for F and G;

n and n' each independently represents 1, 2, 3, 4 and 5, provided that the sum of n and n' is 6;

$R^a$ represents hydrogen, $(C_1-C_6)$alkyl, $(C_2-C_6)$alkenyl, $(C_1-C_6)$alkoxy or $(C_1-C_6)$alkanoyloxy, wherein each $(C_1-C_6)$alkyl, $(C_2-C_6)$alkenyl, $(C_1-C_6)$alkoxy and $(C_1-C_6)$alkanoyloxy is optionally substituted with OH, $(C_1-C_6)$alkoxy, $(C_1-C_6)$alkylthio, aryl, heteroaryl, $NR^fR^g$, or —C(=O)$NR^fR^g$; and wherein each aryl and heteroaryl is optionally substituted with one or two substituents selected independently from halo, hydroxy, $(C_1-C_6)$alkyl, $NR^fR^g$, and $NR^fR^g(C_1-C_6)$alkyl- $R^b$ and $R^c$ each represents hydrogen, or $R^b$ and $R^c$ together represent a bond or —O—;

$R^d$ and $R^e$ together represent (=O) or $R^d$ represents hydrogen and $R^e$ represents hydrogen, hydroxy, $(C_1-C_6)$alkanoyloxy, $NR^jR^k$, $CH_2C(=O)OR^s$ or $CH_2C(=O)NR^mR^n$, wherein each $(C_1-C_6)$alkanoyloxy is optionally substituted with one or more $NR^tR^u$;

$R^{b'}$ and $R^{c'}$ each represents hydrogen, or $R^{b'}$ and $R^{c'}$ together represent a bond or —O—;

$R^{d'}$ and $R^{e'}$ together represent (=O) or $R^{d'}$ represents hydrogen and $R^{e'}$ represents hydrogen, hydroxy, $(C_1-C_6)$alkanoyloxy, $NR^jR^k$, $CH_2C(=O)OR^s$ or $CH_2C(=O)NR^mR^n$, wherein each $(C_1-C_6)$alkanoyloxy is optionally substituted with one or more $NR^tR^u$;

each of $R^f$ and $R^g$ is independently hydrogen, $(C_1-C_6)$alkyl or $(C_1-C_6)$alkanoyl, which $(C_1-C_6)$alkyl is optionally substituted with one or more $NR^tR^u$; or $R^f$ and $R^g$ together with the nitrogen to which they are attached form a pyrrolidino, piperidino, piperazino, morpholino, thiomorpholino, or azepino ring;

each of $R^j$ and $R^k$ is independently hydrogen or $(C_1-C_6)$alkyl, which $(C_1-C_6)$alkyl is optionally substituted with one or more $NR^tR^u$; or $R^j$ and $R^k$ together with the nitrogen to which they are attached form a pyrrolidino, piperidino, piperazino, morpholino, thiomorpholino, or azepino ring;

each of $R^m$ and $R^n$ is independently hydrogen or $(C_1-C_6)$alkyl, which $(C_1-C_6)$alkyl is optionally substituted with one or more $NR^tR^u$; or $R^m$ and $R^n$ together with the nitrogen to which they are attached form a pyrrolidino, piperidino, piperazino, morpholino, thiomorpholino, or azepino ring;

each of $R^1$, $R^2$, and $R^3$ is independently hydrogen $(C_1-C_6)$alkyl, $(C_1-C_6)$alkoxy, aryl or heteroaryl wherein each $(C_1-C_6)$alkyl and $(C_1-C_6)$alkoxy is optionally substituted with OH, $(C_1-C_6)$alkoxy, $(C_1-C_6)$alkylthio, aryl, $NR^oR^p$, or —C(=O)$NR^qR^r$; and wherein each aryl or heteroaryl is optionally substituted with one or two substituents selected independently from a halogen atom and $(C_1-C_4)$alkyl wherein $(C_1-C_4)$alkyl is optionally substituted with $NR^oR^p$;

each of $R^o$ and $R^p$ is independently hydrogen or $(C_1-C_6)$alkyl, which $(C_1-C_6)$alkyl is optionally substituted with one or more $NR^tR^u$; or $R^o$ and $R^p$ together with the nitrogen to which they are attached form a pyrrolidino, piperidino, piperazino, morpholino, thiomorpholino, or azepino ring;

each of $R^q$ and $R^r$ is independently hydrogen or $(C_1-C_6)$alkyl, which $(C_1-C_6)$alkyl is optionally substituted with one or more $NR^tR^u$; or $R^q$ and $R^r$ together with the nitrogen to which they are attached form a pyrrolidino, piperidino, piperazino, morpholino, thiomorpholino, or azepino ring;

$R^s$ is hydrogen or $(C_1-C_6)$alkyl, which $(C_1-C_6)$alkyl is optionally substituted with one or more $NR^tR^u$; and each of $R^t$ and $R^u$ is independently hydrogen, $(C_1-C_6)$alky or $(C_1-C_6)$alkanoyl; or $R^t$ and $R^u$ together with the nitrogen to which they are attached form a pyrrolidino, piperidino, piperazino, morpholino, thiomorpholino, or azepino ring;

or a salt thereof.

The invention also provides a pharmaceutical composition comprising a compound of formula (I), or a pharmaceutically acceptable salt thereof, in combination with a pharmaceutically acceptable diluent or carrier.

Additionally, the invention provides a therapeutic method for treating cancer comprising administering to a mammal (e.g., a human male or female) in need of such therapy, an effective amount of a compound of formula (I), or a pharmaceutically acceptable salt thereof.

The invention provides a compound of formula (I) or a pharmaceutically acceptable salt thereof for use in medical therapy (e.g., for use in treating cancer), as well as the use of a compound of formula (I) or a pharmaceutically acceptable salt thereof for the manufacture of a medicament useful for the treatment of cancer in a mammal, such as a human.

The invention also provides a compound of formula (I) or a pharmaceutically acceptable salt thereof for use in the prophylactic or therapeutic treatment of cancer.

The invention also provides processes and intermediates disclosed herein that are useful for preparing compounds of formula (I) or salts thereof.

DETAILED DESCRIPTION

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl denotes an aromatic heterocyclic ring containing 5 or 6-ring members including from one to four ring hetero atoms selected from oxygen, sulfur and nitrogen, the remainder being carbon, which ring is optionally ortho-fused to a benzene ring or another 5- or 6-membered heteroaromatic ring.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Unless otherwise indicated, the divalent groups A and B, can have either of their two possible orientations (forward or reversed) in the compounds of formula (I) and other ring systems disclosed herein. For example, when A represents —CH($R^a$)NHC(=O)—, this group may have the orientation —CH($R^a$)NHC(=O)— or —(O=C)NHCH($R^a$)—.

In cases where $R^b$ and $R^c$ together represent a bond, the resulting bond between CH($R^b$) and CH($R^c$) is a double bond.

In cases where $R^{b'}$ and $R^{c'}$ together represent a bond, the resulting bond between $CH(R^{b'})$ and $CH(R^{c'})$ is a double bond.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; and aryl can be phenyl, indenyl, or naphthyl. Heteroaryl can be pyridyl.

In one embodiment, the compounds of formula (I) include

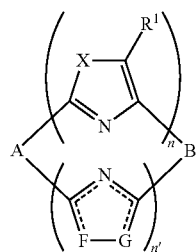

(I)

wherein:
one of A and B is —$CH(R^b)CH(R^c)CH(R^d)C(R^e)$—;
and the other of A and B is:

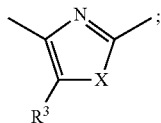

—$CH(R^a)NHC(=O)$— or —$CH(R^{b'})CH(R^{c'})C(R^{d'})(R^{e'})$—;
one of F and G is X and the other is $C(R^2)$;
each X is independently NH, S, or O;
the dotted line in the ring containing F and G signifies that two double bonds are present in the ring, the positions of which depend upon the values selected for F and G;
n and n' each independently represents 1, 2, 3, 4 and 5, provided that the sum of n and n' is 6;
$R^a$ represents hydrogen, $(C_1-C_6)$alkyl, $(C_1-C_6)$alkoxy or $(C_1-C_6)$alkanoyloxy, wherein each $(C_1-C_6)$alkyl, $(C_1-C_6)$alkoxy and $(C_1-C_6)$alkanoyloxy, is optionally substituted with OH, $(C_1-C_6)$alkoxy, $(C_1-C_6)$alkylthio, aryl, heteroaryl, $NR^fR^g$ or —$C(=O)NR^fR^g$; and wherein each aryl and heteroaryl is optionally substituted with one or two substituents selected independently from halo, $(C_1-C_6)$alkyl, $NR^fR^g$ and $NR^fR^g(C_1-C_6)$alkyl-
$R^b$ and $R^c$ each represents hydrogen, or $R^b$ and $R^c$ together represent a bond or —O—;

$R^d$ and $R^e$ together represent (=O) or $R^d$ represents hydrogen and $R^e$ represents hydrogen, hydroxy, $(C_1-C_6)$alkanoyloxy, $NR^jR^k$, $CH_2C(=O)OR^s$ or $CH_2C(=O)NR^mR^n$, wherein each $(C_1-C_6)$alkanoyloxy is optionally substituted with one or more $NR^tR^u$;

$R^{b'}$ and $R^{c'}$ each represents hydrogen, or $R^{b'}$ and $R^{c'}$ together represent a bond or —O—;

$R^{d'}$ and $R^{e'}$ together represent (=O) or $R^{d'}$ represents hydrogen and $R^{e'}$ represents hydrogen, hydroxy, $(C_1-C_6)$alkanoyloxy, $NR^jR^k$, $CH_2C(=O)OR^s$ or $CH_2C(=O)NR^mR^n$, wherein each $(C_1-C_6)$alkanoyloxy is optionally substituted with one or more $NR^tR^u$;

each of $R^f$ and $R^g$ is independently hydrogen or $(C_1-C_6)$alkyl, which $(C_1-C_6)$alkyl is optionally substituted with one or more $NR^tR^u$; or $R^f$ and $R^g$ together with the nitrogen to which they are attached form a pyrrolidino, piperidino, piperazino, morpholino, thiomorpholino, or azepino ring;

each of $R^j$ and $R^k$ is independently hydrogen or $(C_1-C_6)$alkyl, which $(C_1-C_6)$alkyl is optionally substituted with one or more $NR^tR^u$; or $R^j$ and $R^k$ together with the nitrogen to which they are attached form a pyrrolidino, piperidino, piperazino, morpholino, thiomorpholino, or azepino ring;

each of $R^m$ and $R^n$ is independently hydrogen or $(C_1-C_6)$alkyl, which $(C_1-C_6)$alkyl is optionally substituted with one or more $NR^tR^u$; or $R^m$ and $R^n$ together with the nitrogen to which they are attached form a pyrrolidino, piperidino, piperazino, morpholino, thiomorpholino, or azepino ring;

each of $R^1$, $R^2$, and $R^3$ is independently hydrogen, $(C_1-C_6)$alkyl, $(C_1-C_6)$alkoxy, aryl or heteroaryl wherein each $(C_1-C_6)$alkyl and $(C_1-C_6)$alkoxy is optionally substituted with OH, $(C_1-C_6)$alkoxy, $(C_1-C_6)$alkylthio, aryl, $NR^oR^p$, or —$C(=O)NR^qR^r$; and wherein each aryl or heteroaryl is optionally substituted with one or two substituents selected independently from a halogen atom and $(C_1-C_4)$alkyl wherein $(C_1-C_4)$alkyl is optionally substituted with $NR^oR^p$;

each of $R^o$ and $R^p$ is independently hydrogen or $(C_1-C_6)$alkyl, which $(C_1-C_6)$alkyl is optionally substituted with one or more $NR^tR^u$; or $R^o$ and $R^p$ together with the nitrogen to which they are attached fowl a pyrrolidino, piperidino, piperazino, morpholino, thiomorpholino, or azepino ring;

each of $R^q$ and $R^r$ is independently hydrogen or $(C_1-C_6)$alkyl, which $(C_1-C_6)$alkyl is optionally substituted with one or more $NR^tR^u$; or $R^q$ and $R^r$ together with the nitrogen to which they are attached form a pyrrolidino, piperidino, piperazino, morpholino, thiomorpholino, or azepino ring;

$R^s$ is hydrogen or $(C_1-C_6)$alkyl, which $(C_1-C_6)$alkyl is optionally substituted with one or more $NR^tR^u$; and each of $R^t$ and $R^u$ is independently hydrogen, $(C_1-C_6)$alkyl or $(C_1-C_6)$alkanoyl, or $R^t$ and $R^u$ together with the nitrogen to which they are attached form a pyrrolidino, piperidino, piperazino, morpholino, thiomorpholino, or azepino ring.

or a salt thereof.

In one embodiment, the compounds of formula (I) have the structure (I'):

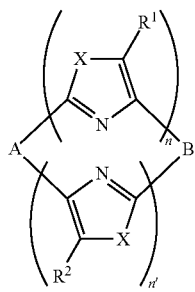
(I')

In another embodiment, they have the structure (I"):

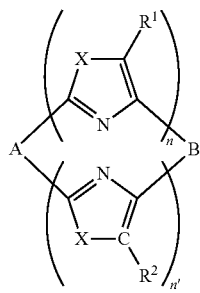
(I")

An example of a particular value for each X in the compounds of formulae (I) is O.

An example of a value for A when it represents

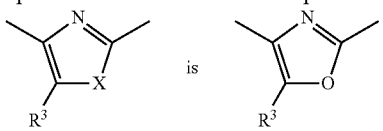

An example of a value for $R^3$ is hydrogen.

Examples of values for A when it represents —CH($R^a$)NHC(=O)— are —CH$_2$NHC(=O)—, —CH(CH$_3$)NHC(=O)—, —CH(CH(CH$_3$)$_2$)NHC(=O)—, —CH(CH(CH$_3$)(CH$_2$CH$_3$))NHC(=O)—, —CH(CH$_2$CH(CH$_3$)$_2$)NHC(=O)—, and —CH(CH$_2$Ph)NHC(=O)—.

Examples of particular values for $R^a$ are hydrogen, methyl, isopropyl, 1-methylpropyl, 2-methylpropyl, benzyl, 4-hydroxybenzyl, 4-iodobenzyl, 4-aminobenzyl, and 4-(2-N,N-dimethylaminoethylamino)benzyl, more particularly methyl, isopropyl, 1-methylpropyl, 2-methylpropyl and benzyl.

Examples of particular values for $R^a$ are $(C_1-C_6)$alkyl or $(C_2-C_6)$alkenyl wherein each $(C_1-C_6)$alkyl, and $(C_2-C_6)$alkenyl, is optionally substituted with $NR^fR^g$.

Examples of particular values for $R^a$ are aminomethyl, 2-aminoethyl, 3-aminopropyl or 4-aminobutyl.

Examples of particular values for A when it represents —CH($R^{b'}$)CH($R^{c'}$)C($R^{d'}$)($R^{e'}$)— are —CH=CH—CH$_2$—, —CH=CH—CH(OH)—, —CH=CH—CH(CH$_2$CON(CH$_3$)$_2$))— and —CH=CH—CH(CH$_2$CO$_2$CH$_3$)—

Examples of particular values for $R^{b'}$ and $R^{c'}$ are, together are a bond.

An example of a particular value for $R^{d'}$ is hydrogen.

Examples of particular values for $R^{e'}$ are hydrogen, hydroxy, CH$_2$C(=O)OCH$_3$, CH$_2$C(=O)N(CH$_3$)$_2$, and CH$_2$C(=O)NHCH$_2$CH$_2$N(CH$_3$)$_2$. Examples of values for B are —CH=CH—CH$_2$—, —CH=CH—CH(OH)—, —CH=CH—CH(CH$_2$CON(CH$_3$)$_2$))— and —CH=CH—CH(CH$_2$CO$_2$CH$_3$)—.

Examples of particular values for $R^b$ and $R^c$ are, together are a bond.

An example of a particular value for $R^d$ is hydrogen.

Examples of particular values for $R^e$ are hydrogen, hydroxy, CH$_2$C(=O)OCH$_3$, CH$_2$C(=O)N(CH$_3$)$_2$, and CH$_2$C(=O)NHCH$_2$CH$_2$N(CH$_3$)$_2$.

A particular value for $R^1$ is hydrogen.

A particular value for $R^2$ is hydrogen.

Examples of compounds of formula (I) are compounds of formulae:

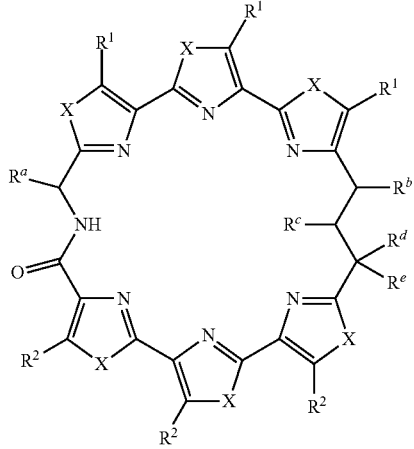
(Ia')

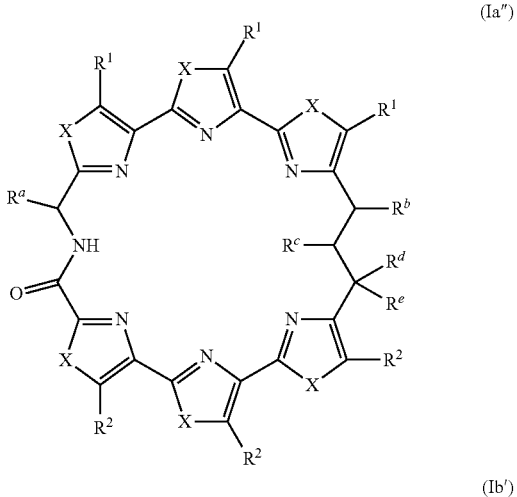
(Ia")

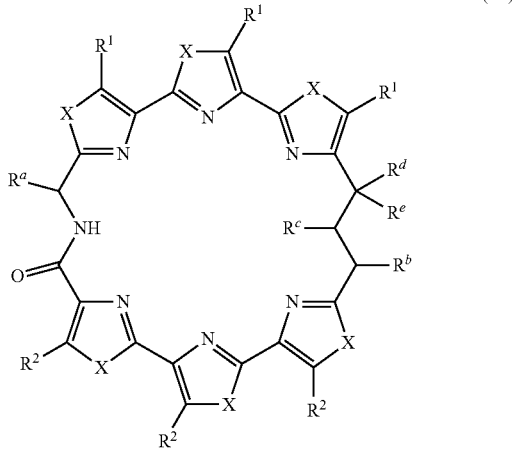
(Ib')

(Ib″)
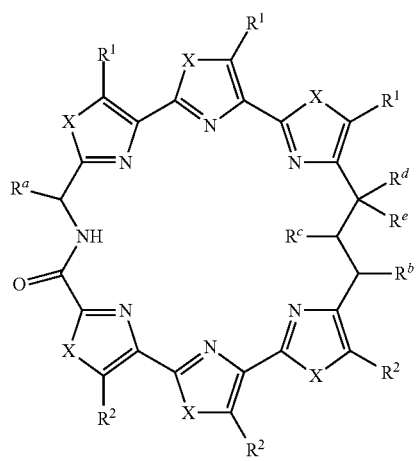
(Id′)
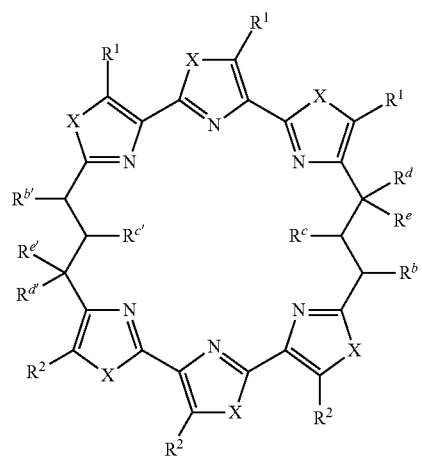
(Ic′)
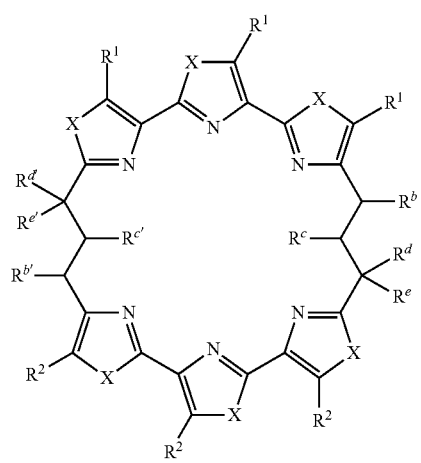
(Id″)
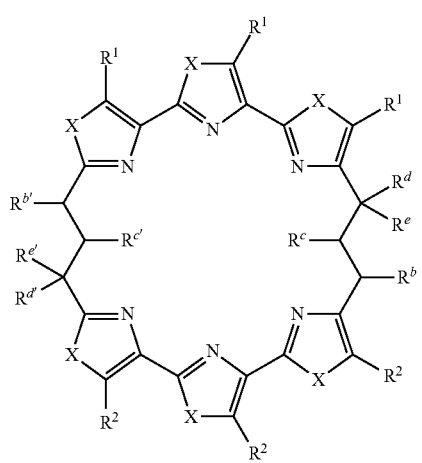
(Ic″)
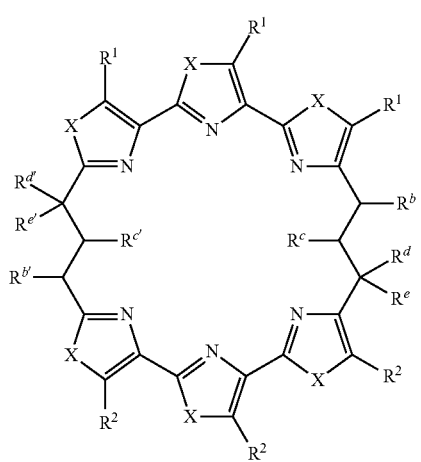
(Ie″)
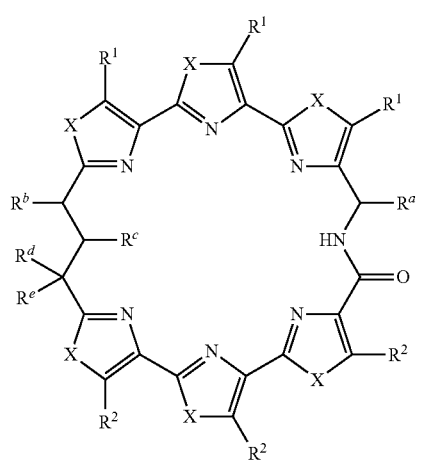
and

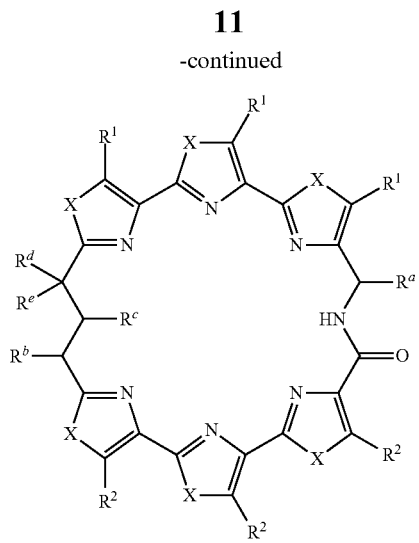

in which:
$R^1$, $R^2$, $R^a$, $R^b$, $R^c$, $R^d$, $R^e$, $R^{b'}$, $R^{c'}$, $R^{d'}$ and $R^{e'}$ have any of the meanings described hereinabove.

A particular value, for $R^1$ is hydrogen; and for $R^2$ is hydrogen.

Additional examples of compounds of formula (I) are compounds of formulae:

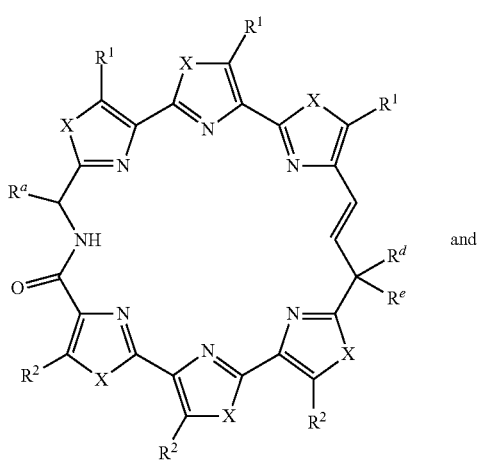

and in which:
$R^1$, $R^2$, $R^a$, $R^b$, $R^c$, $R^d$, $R^e$, $R^{b'}$, $R^{c'}$, $R^{d'}$ and $R^{e'}$ have any of the meanings described hereinabove.

A particular value for $R^a$ is alkyl, for $R^1$ is hydrogen and for $R^2$ is hydrogen.

A particular value for $R^a$ is also $(C_1-C_6)$alkyl or $(C_2-C_6)$alkenyl wherein each $(C_1-C_6)$alkyl, and $(C_2-C_6)$alkenyl, is optionally substituted with $NR^f R^g$.

A particular value for $R^a$ is also aminomethyl, 2-aminoethyl, 3-aminopropyl or 4-aminobutyl.

The compounds of formula (I) can be prepared by forming an intermediate comprising a linear chain of the requisite polyazoles, olefin and peptide/olefin, or a protective derivative thereof, then cyclizing this by olefin metathesis or by using the Heck coupling reaction, and optionally derivatizing one or more olefin groups, removing any protecting groups and optionally forming a salt.

Examples of representative synthetic routes to compounds of formula (I) are provided in Schemes 1 to 6 below. Although $R^1$, $R^2$, and $R^3$ are hydrogen in the illustrated compounds, these or similar synthetic routes can also be used to prepare other compounds wherein $R^1$, $R^2$, and $R^3$ have other values.

Scheme 1
Preparation of Macrocyclic Azoles via Condensation and Metathesis

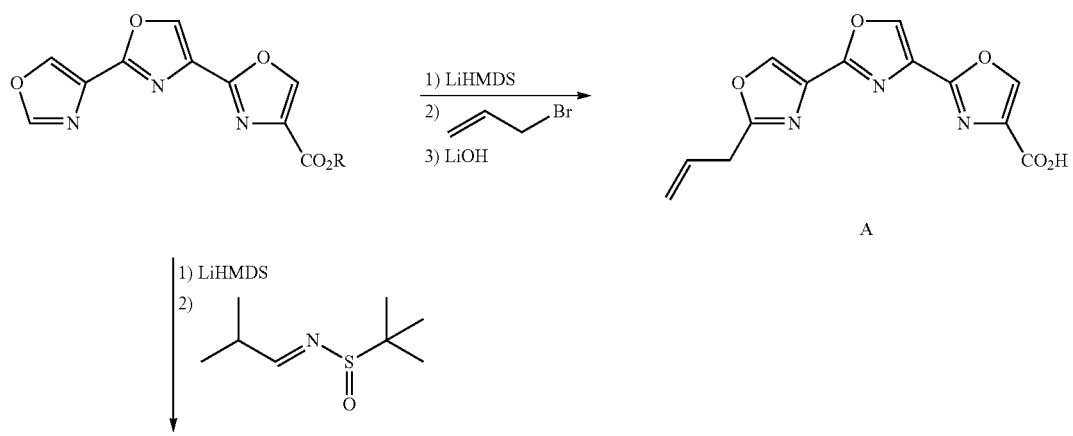

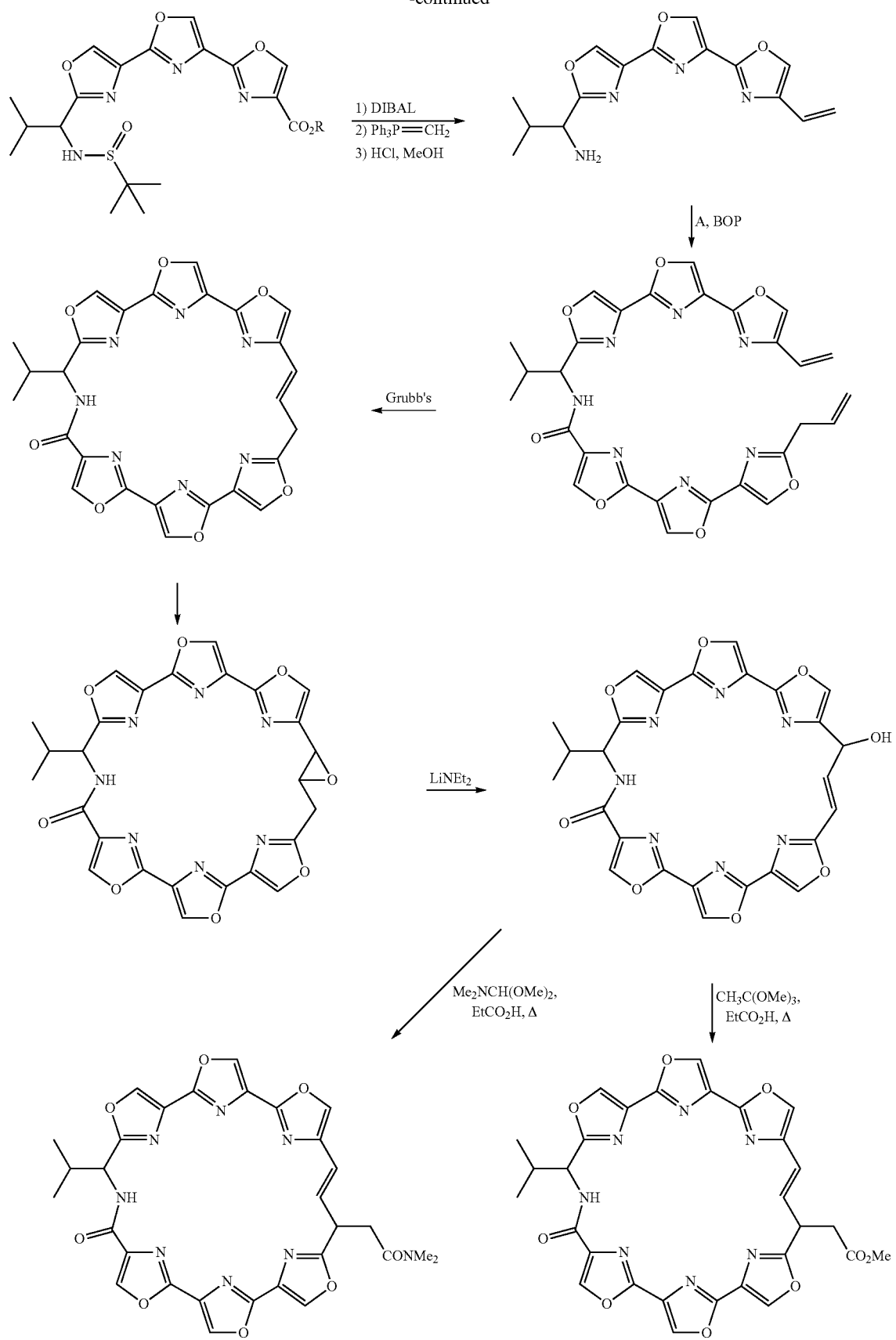

Scheme 2
Preparation of Macrocyclic Azoles via Heck Coupling and Metathesis
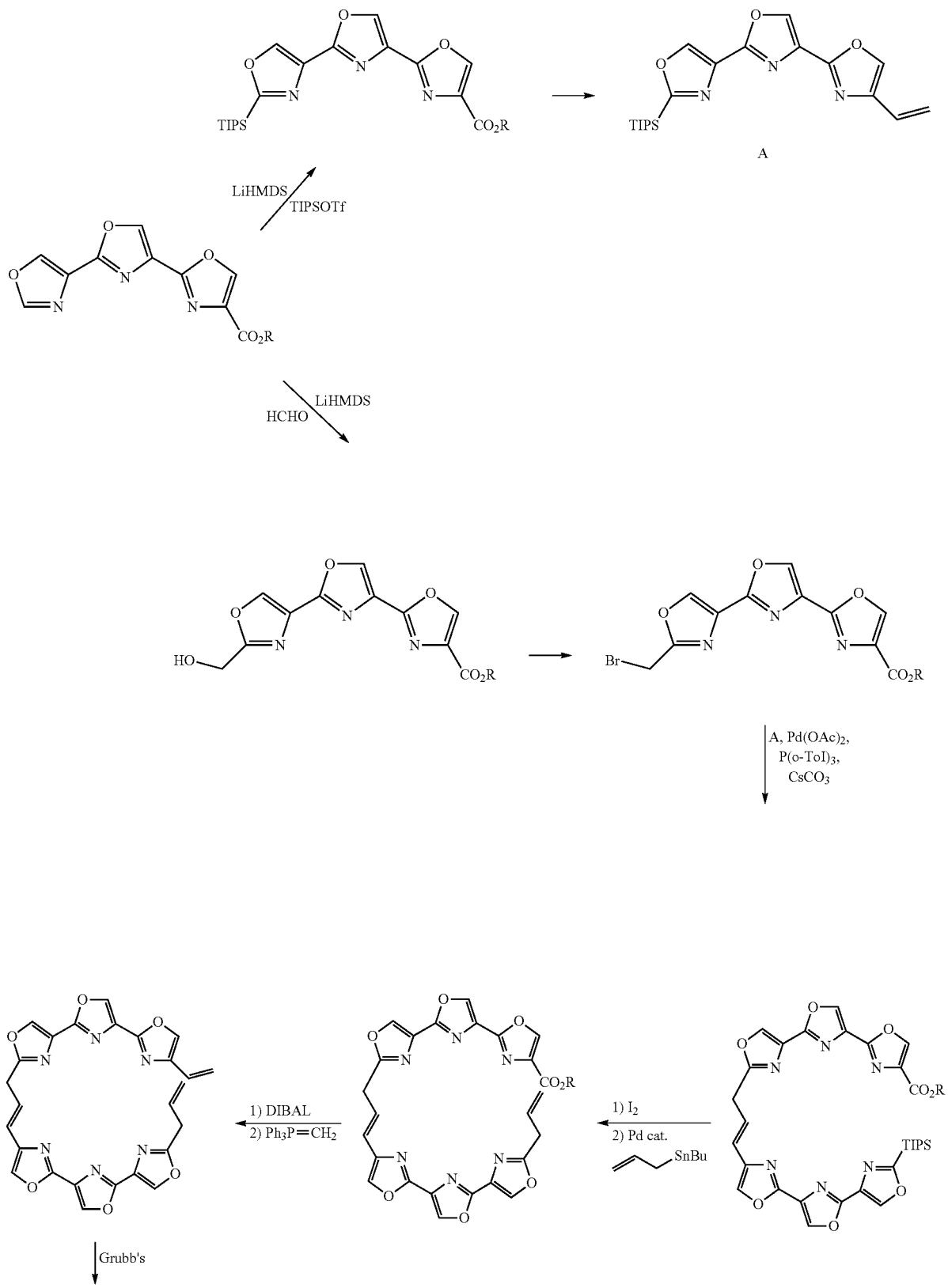

17
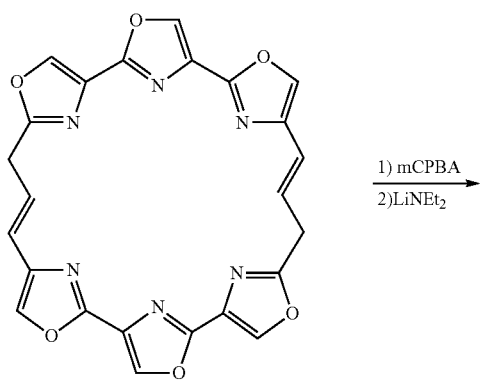
18
-continued
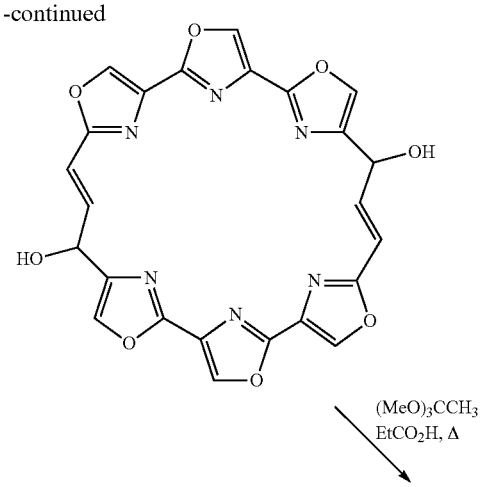
1) mCPBA
2) LiNEt₂
(MeO)₃CCH₃
EtCO₂H, Δ
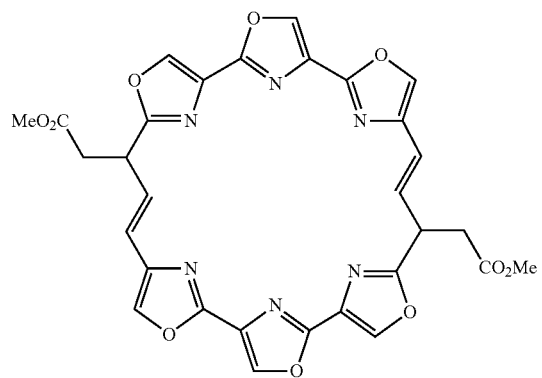 [SMILES: COC(=O)CC1/C=C/c2coc(n2)-c2coc(n2)-c2coc(n2)C(CC(=O)OC)/C=C/c2coc(n2)-c2coc(n2)-c2coc1n2]
Scheme 3
"Normal" Heck Coupling
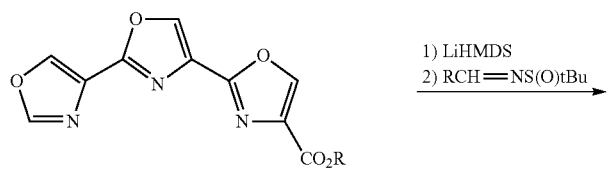
1) LiHMDS
2) RCH=NS(O)tBu
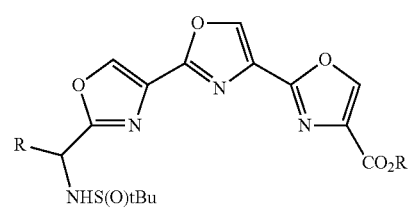
1) DIBAL
2) TsCl
3) (H₂C=CH)₂CuLi
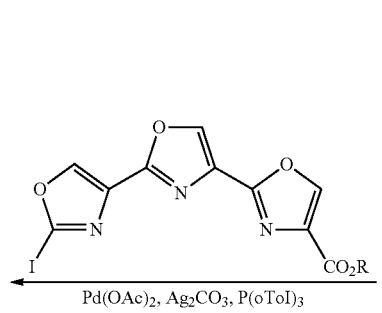
Pd(OAc)₂, Ag₂CO₃, P(oTol)₃
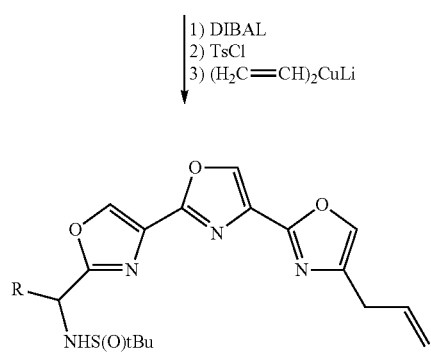

19
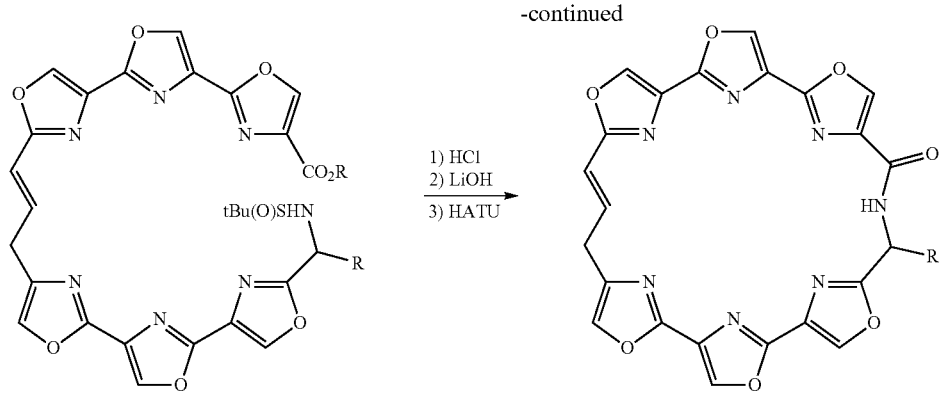
Scheme 4
"Normal" Metathesis
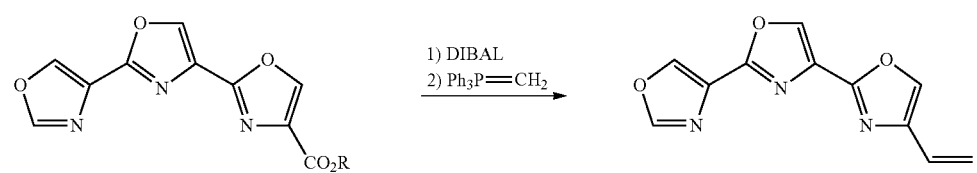
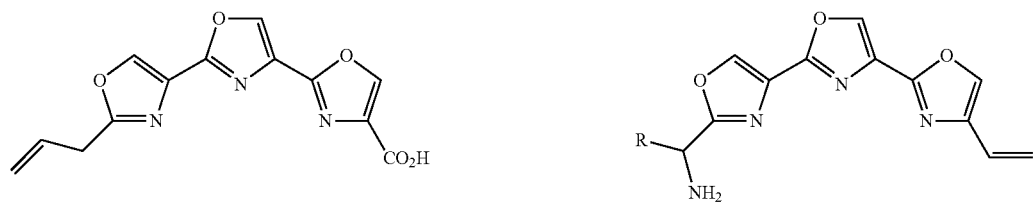
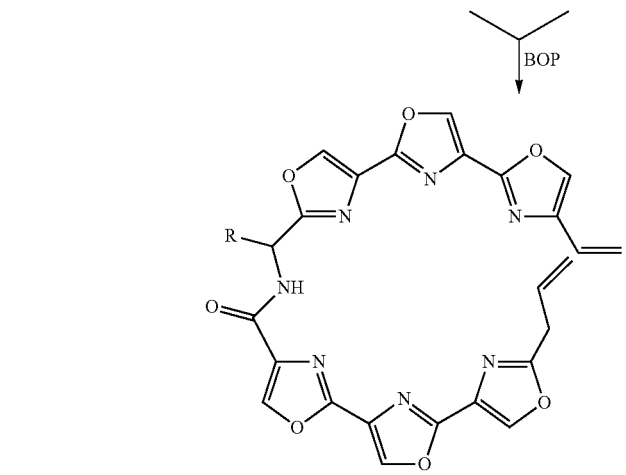
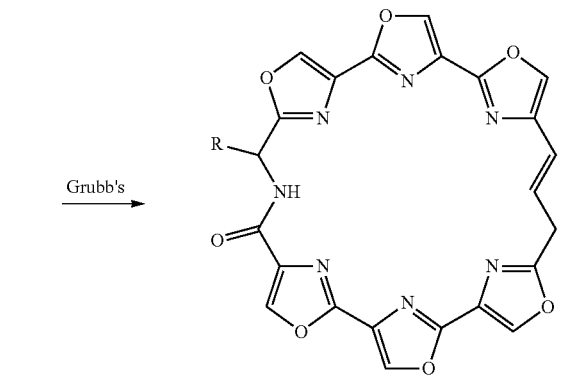

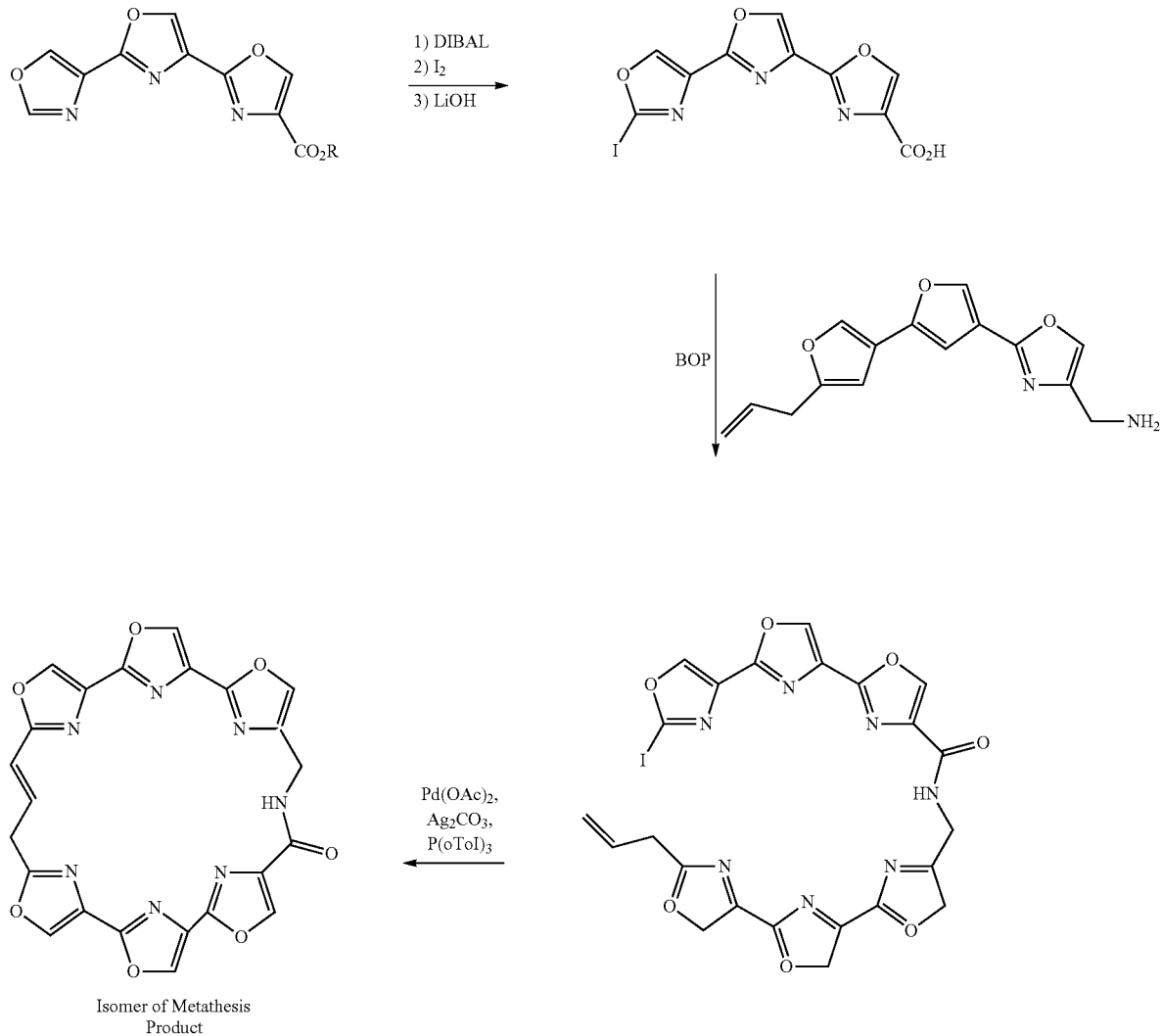
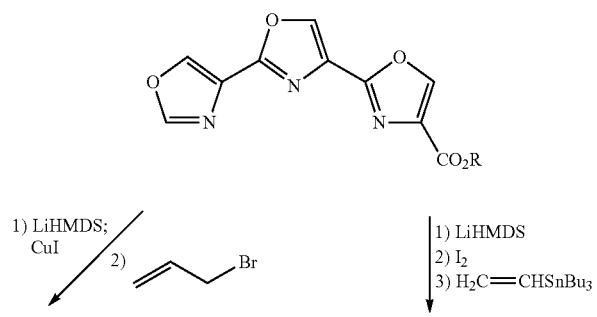

23
24
-continued
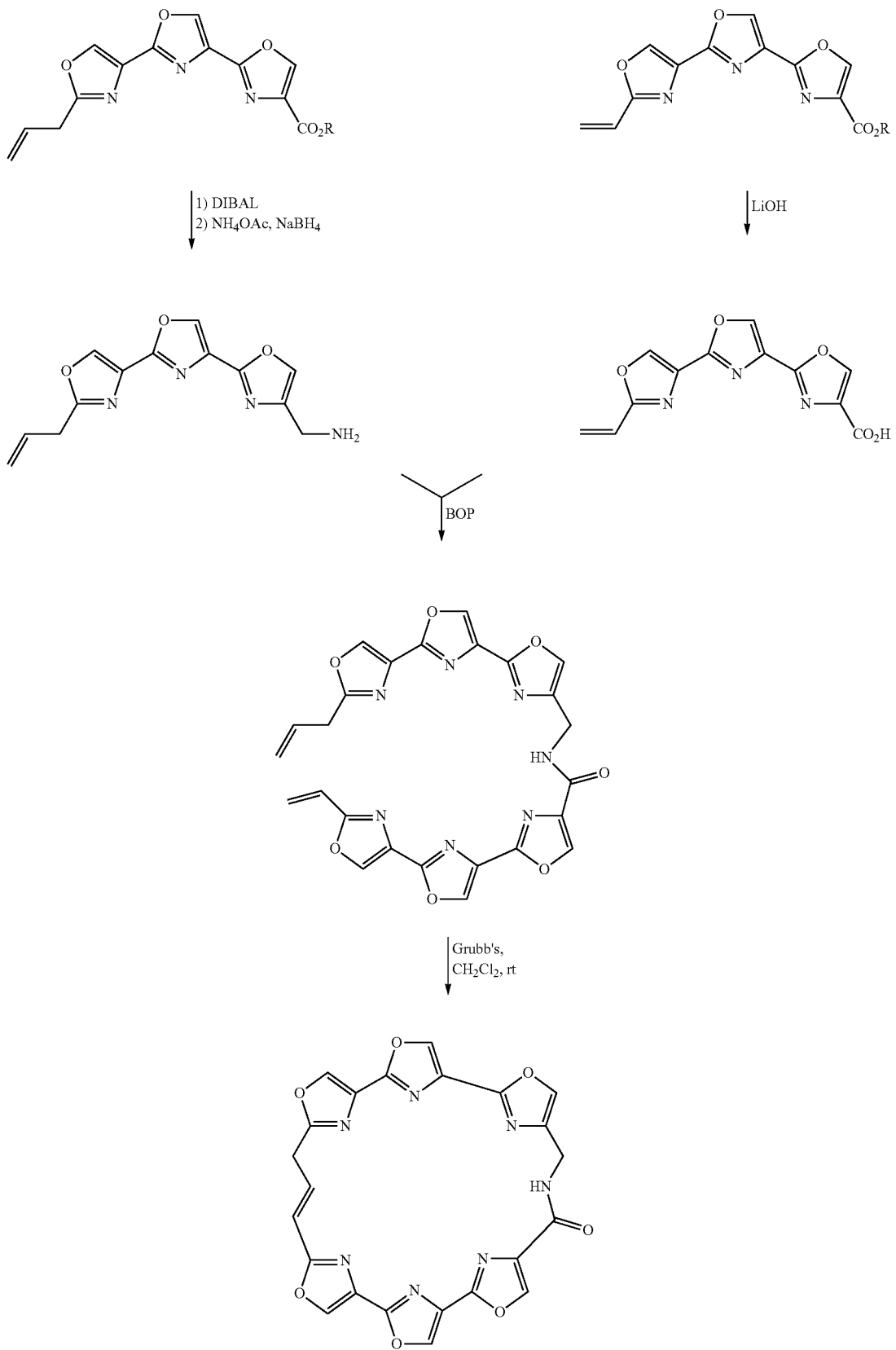

Additional examples of representative synthetic routes to compounds of formula (I) are provided in Scheme 7 below.
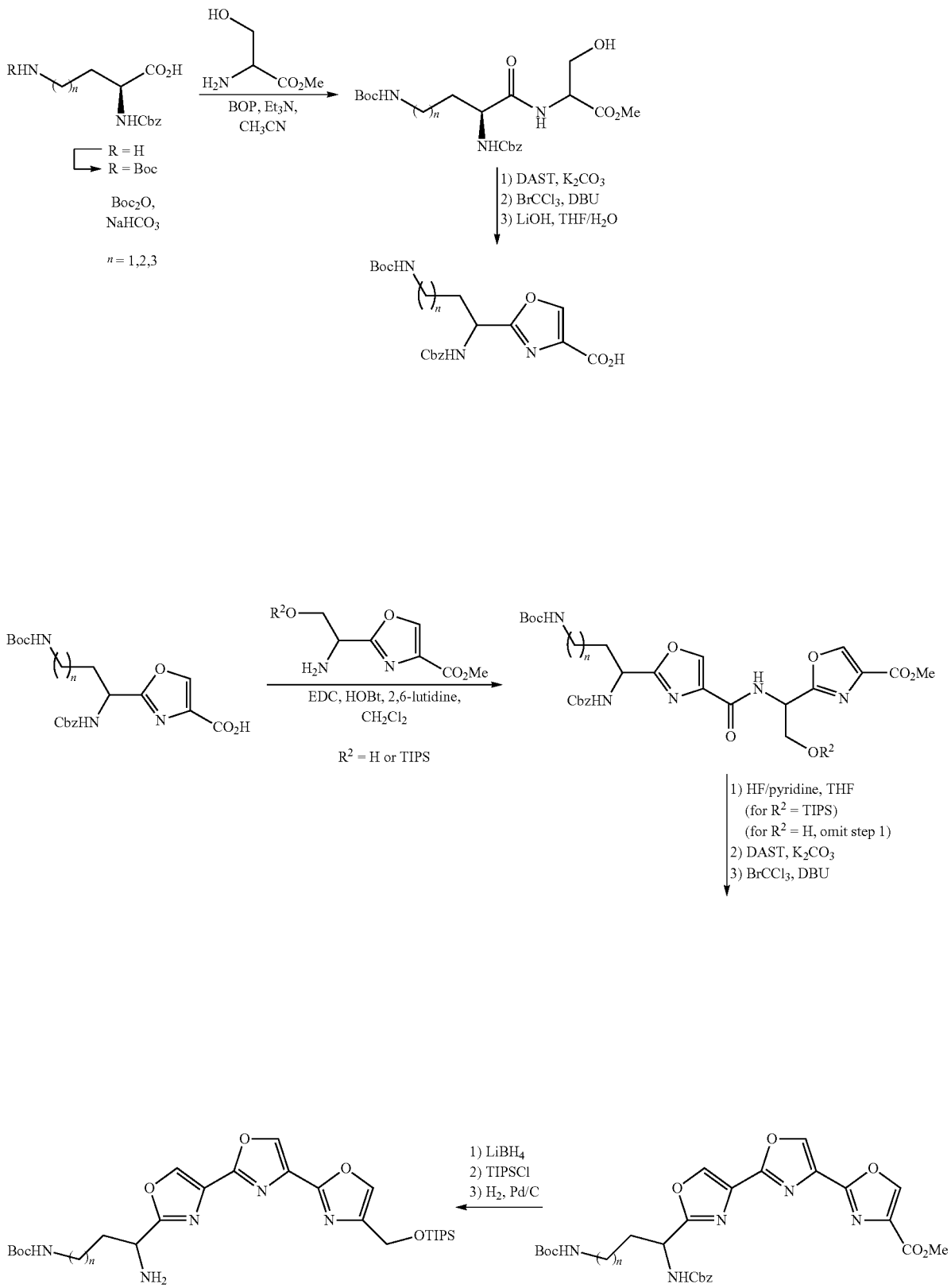
Scheme 7

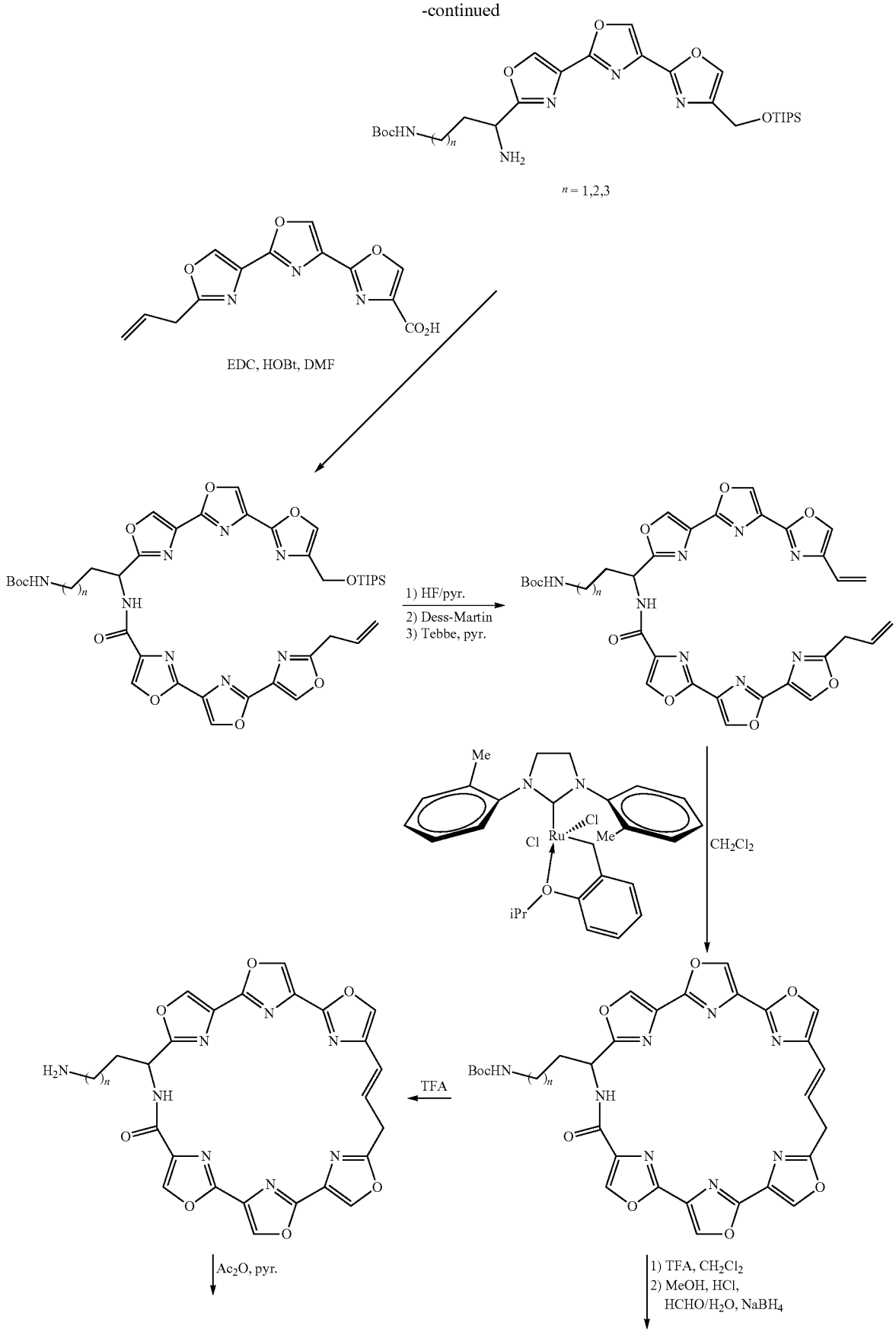

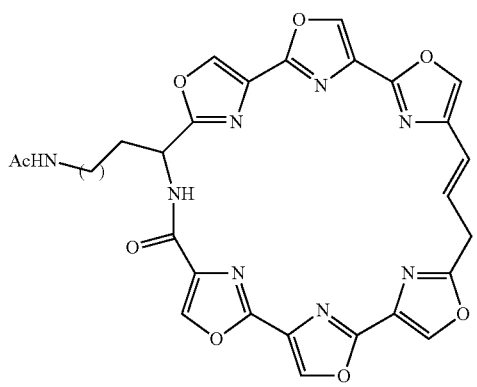 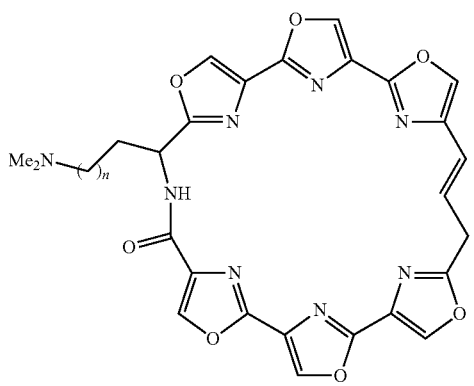

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), a vegetable oil, a nontoxic glyceryl ester, and suitable mixtures thereof. The proper fluidity can be maintained., for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula (I) in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g. from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of cancer. Accordingly, in one embodiment the invention also provides a composition comprising a compound of formula (I), or a pharmaceutically acceptable salt thereof, at least one other therapeutic agent, and a pharmaceutically acceptable diluent or carrier. The invention also provides a kit comprising a compound of formula (I), or a pharmaceutically acceptable salt thereof, at least one other therapeutic agent, packaging material, and instructions for administering the compound of formula I or the pharmaceutically acceptable salt thereof and the other therapeutic agent or agents to an animal to treat cancer.

The ability of a compound of the invention to stabilize G-quadroplex DNA may be determined using pharmacological models which are well known to the art, or using Test A described below.

Test A. Stabilization of G-quadruplex DNA

Analyses can be performed to determine the ability of the agents to bind and thermally stabilize the duplex, triplex, and quadruplex forms of nucleic acids. Toward this end, the UV absorbances of the nucleic acids as a function of temperature in the absence and presence of HXDV is monitored. The melting of duplex and triplex nucleic acids is generally associated with a hyperchromic shift at 260 nm, while the melting of quadruplex nucleic acids is associated with a hypochromic shift at 295 nm. Thus, the temperature-dependent absorbances of duplexes and triplexes is monitored at 260 nm, with corresponding quadruplex absorbances being monitored at 295 nm. ST DNA, p(rA)•p(rU), p(rA)•p(dT), p(dA)•2p(dT), p(rA)•2p(rU), d($T_2AG_3$)$_4$, and r($UG_4U$) is used as representative models of a DNA duplex, an RNA duplex, a hybrid DNA•RNA duplex, a DNA triplex, an RNA triplex, a DNA quadruplex, and an RNA quadruplex, respectively. All the UV melting studies are conducted at pH 7.5 in the presence of potassium ions.

The ability of compounds to stabilize G-quadroplex DNA may also be determined using Test B described below.

Test B. Temperature-Dependent Spectrophotometry

Temperature-dependent absorption experiments are conducted on an AVIV Model 14DS Spectrophotometer (Aviv Biomedical, Lakewood, N.J.) equipped with a thermoelectrically controlled cell holder. Quartz cells with a pathlength of 1.0 cm are sed for all the absorbance studies. Temperature-dependent absorption profiles are acquired at either 260 (for duplex and triplex) or 295 (for quadruplex) nm with a 5 sec averaging time. The temperature is raised in 0.5° C. increments, and the samples are allowed to equilibrate for 1.5 min at each temperature setting. In the quadruplex melting studies, the concentrations of d(T$_2$AG$_3$)$_4$, 9AP, 15AP, and 21AP are 5 µM in strand (120 µM in nucleotide), while the concentration of r(UG$_4$U) is 20 µM in strand (120 µM in nucleotide). In the duplex and triplex melting studies, the nucleic acid concentration is 15 µM in base pair (30 µM in nucleotide) or 15 µM in base triple (45 µM in nucleotide) and the HXDV concentration, when present, is 15 µM. The buffer for all the UV melting experiments contains 10 mM EPPS (pH 7.5). In addition, sufficient KCl is added to each solution to bring the total K$^+$ concentration to either 150 mM for d(T$_2$AG$_3$)$_4$ and p(rA)•p(dT), 2 mM for r(UG$_4$U), 50 mM for ST DNA, 250 mM for p(dA)•2p(dT), or 20 mM for p(rA)•2p(rU). Prior to their use in UV melting experiments, all nucleic acid solutions are preheated at 90° C. for 5 min and slowly cooled to room temperature over a period of 4 hr.

The anti-proliferative activity of a compound of the invention may be determined using pharmacological models which are well known to the art, or using Test C described below.

Test C. Evaluation of G-Quadruplex Stabilizers Using the MTT Assay.

Cell lines are selected based upon one or more factors including data on their relative telomerase activity, varied organ sites, available comparative data, and their ability to form solid tumors in athymic nude mice. The advantage of an MTT assay is that the cytotoxic/cytostatic activities can be readily determined. Cells are cultured for 4 days at 37° C. followed by addition of MTT (3-[4,5-dimethylthiozol-2-yl]-2,5-diphenyltetrazolium bromide (Sigma) (0.1 mg/ml). Cells are treated with MTT for 3 hrs and then dissolved in 100 µl 100% DMSO. Absorbance is measured at OD$_{570}$ using a microplate reader (Model 3550 UV from BIO-RAD). The MTT value is normalized to OD$_{570}$ of cells treated with Cellfectin alone. Stock solutions of each compound are prepared. MTT assays are performed using spectrometric analysis and 96 well plates. Compound 258, a representative compound of formula I, was evaluated against a variety of cell lines using the MTT assay compound. Compound 258 displays potent cytotoxic activity against murine leukemia P388 (IC$_{50}$=45 nM), human lymphoblastoma RPMI 8402 (IC$_{50}$=25 nM) and human nasopharyngeal carcinoma KB3-1 (IC$_{50}$=25 nM).

The following non-limiting examples illustrate the preparation of compounds of formula (I) as well as synthetic intermediates useful for the synthesis of compounds of formula (I).

EXAMPLE 1

Preparation of Representative Compounds of the Invention

Using procedures similar to those described herein, the following representative compounds of the invention can be prepared.

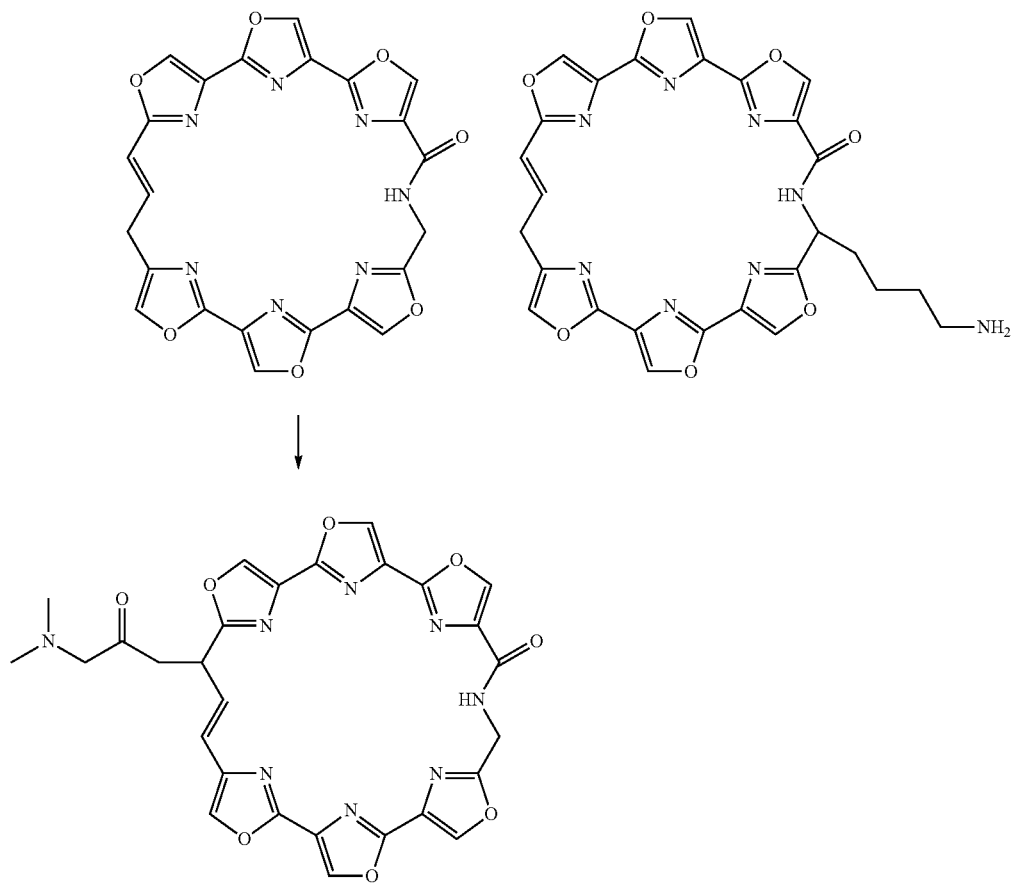

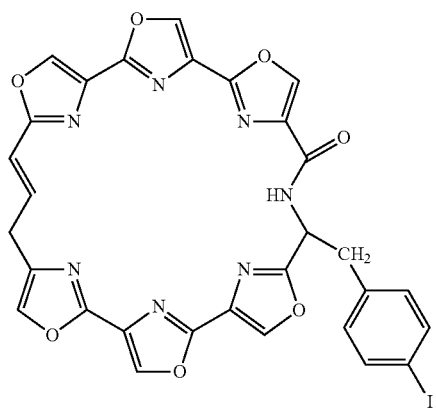
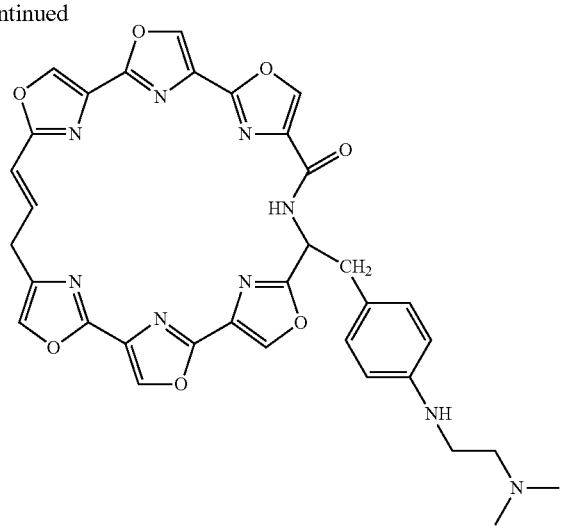
EXAMPLE 2
Preparation of Representative Compounds of the Invention
Using procedures similar to those described herein, the following representative compounds of the invention can be prepared.
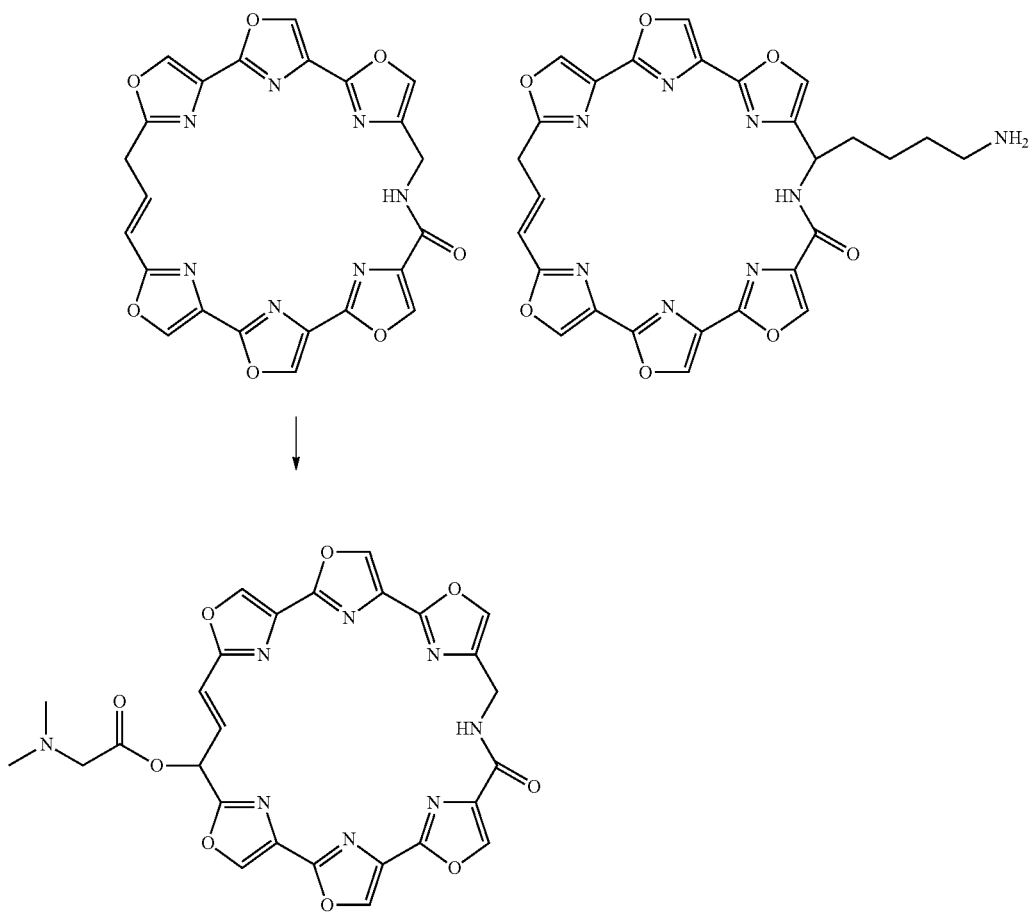

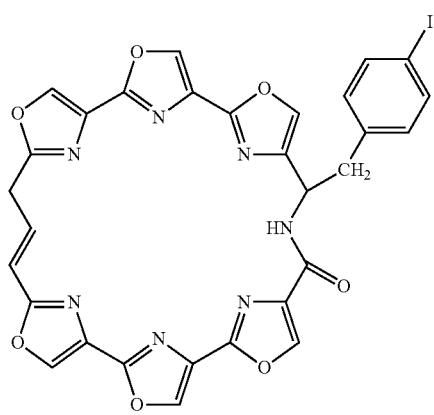

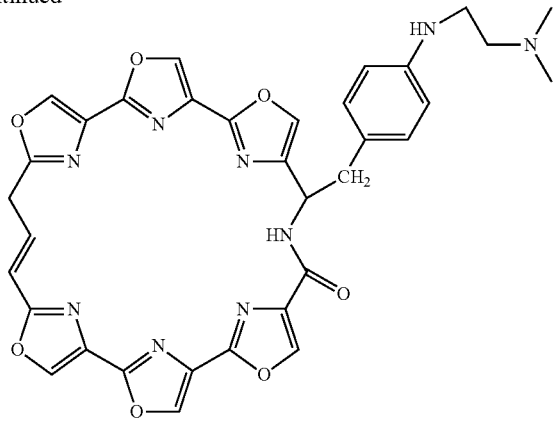

EXAMPLE 3

Preparation of Teroxazole Intermediate

A teroxazole intermediate that can be used to prepare compounds of the invention can be prepared as follows.

a. Synthesis of Compound 206 (N-Boc Valine Amide)

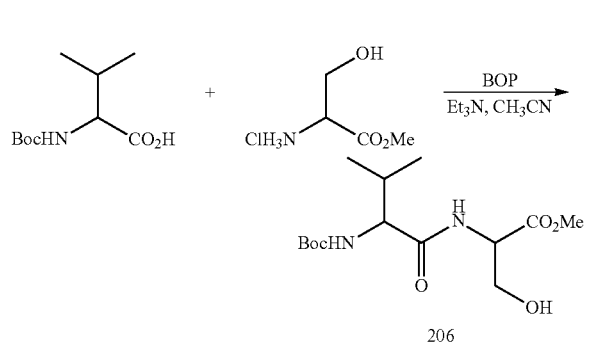

Dry acetonitrile (100 mL) was added to a mixture of N-Boc-L-valine (2.17 g, 10 mmol) and serine methyl ester hydrochloride (1.86 g, 12 mmol) and stirred for 5 min. BOP (4.42 g, 10 mmol) and triethylamine (3.1 mL, 22 mmol) were added and the mixture was stirred at room temperature for 12 h. The mixture was then evaporated under reduced pressure and diluted with EtOAc and brine. The phases were separated and then aqueous phase was extracted with EtOAc. The combined organic phases were then washed successively with 1N HCl, saturated NaHCO$_3$, and brine and then dried over Na$_2$SO$_4$, filtered and evaporated to give the amide as a colorless oil, 3.18 g (100%); $^1$H NMR (CDCl$_3$) δ 7.45 (dd, 1H, J=1.4), 5.58 (d, 1H, J=8.8), 4.45 (m, 1H), 4.37 (m, 1H), 3.79 (m, 2H), 3.54 (s, 3H), 1.88 (m, 1H), 1.23 (s, 9H), 0.74 (d, 6H, J=6.6); $^{13}$C-NMR δ 172.3, 171.0, 162.9, 156.0, 79.4, 62.3, 54.6, 52.3, 31.3, 28.2, 17.7, 17.4.

b. Synthesis of Compound 207 (N-Boc Valine Oxazoline)

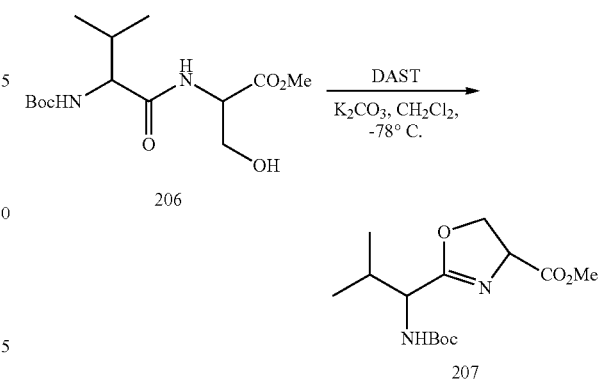

A solution of 206 (2.54 g, 8 mmol) in CH$_2$Cl$_2$ (16 mL) was cooled to −78° C. under nitrogen and treated with DAST (1.7 mL, 13.2 mmol). After stirring for 1.5 h anhydrous K$_2$CO$_3$ (1.32 g) was added and the mixture was then allowed to warm to room temperature. The mixture was poured into saturated NaHCO$_3$ and extracted several times with CH$_2$Cl$_2$. The combined extracts were dried over Na$_2$SO$_4$, filtered and concentrated to give oxazoline 207 as a red-yellow oil, 2.36 g (98%, crude); $^1$H NMR (CDCl$_3$) δ 5.12 (d, 1H, J=8.4), 4.70 (m, 1H), 4.41 (m, 3H), 3.74 (s, 3H), 2.02 (m, 1H), 1.24 (s, 9H), 0.74 (d, 6H, J=6.6); $^{13}$C-NMR δ 171.3, 169.5, 155.5, 79.6, 69.8, 67.8, 54.1, 52.6, 31.8, 28.3, 17.7, 17.3.

c. Synthesis of Compound 208 (N-Boc Valine Oxazole)

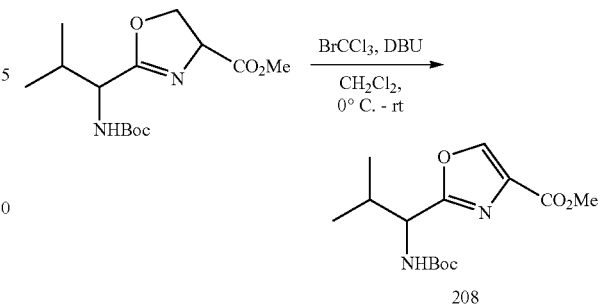

A solution of the crude oxazoline (2.36 g, 7.9 mmol) in dry CH$_2$Cl$_2$ (24 mL) was stirred under nitrogen at 0° C. as dry DBU (1.8 mL, 12.5 mmol) was added over 2 min followed by BrCCl$_3$ (1.2 mL, 12.5 mmol) which was then added over 5 min. The reaction was stirred at 0° C. for 5 h and was then poured into saturated NH$_4$Cl. The mixture was extracted with CH$_2$Cl$_2$ and the combined extracts were dried over Na$_2$SO$_4$, filtered, and evaporated. The product was purified by flash chromatography on silica gel eluting with 2:3 EtOAc/hexane to give the oxazole as a white solid, 2.36 g (75%); mp 125-129° C.; $^1$H NMR (CDCl$_3$) δ 8.1 (s, 1H), 5.31 (d, 1H, J=9.2), 4.63 (dd, 1H, J=9,6), 3.73 (s, 3H), 2.04 (m, 1H), 1.25 (s, 9H), 0.74 (d, 6H, J=6.6); $^{13}$C NMR δ 165.0, 161.5, 155.3, 143.9, 133.0, 79.7, 54.2, 52.0, 32.8, 28.2, 18.6, 17.9.

d. Synthesis of Compound 209 (N-Boc Valine Oxazole Carboxylic Acid)

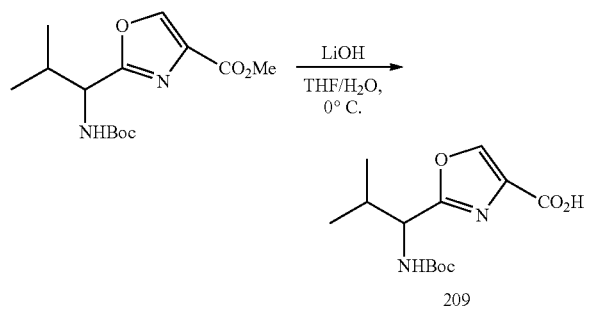

A solution of the ester (0.8 g, 2.68 mmol) in 3:1 THF/H$_2$O (32 mL) was stirred at 0° C. as LiOH (134 mg, 3.19 mmol) was added in one portion. The reaction mixture was stirred for 10 h and was then evaporated under reduced pressure to remove THF. The aqueous solution was brought to pH 3 with 1N HCl and was then extracted with EtOAc. The organic phase was washed with brine and dried over Na$_2$SO$_4$, filtered and evaporated to give the carboxylic acid as a white solid, 0.67 g (88%); mp 157-160° C.; $^1$H NMR (CDCl$_3$) δ 8.2 (s, 1H), 6.34 (d, 1H, J=8.4), 4.78 (t, 1H, J=8.3), 2.16 (m, 1H), 1.33 (s, 9H), 0.87 (dd, 6H, J=14.7); $^{13}$C NMR δ 166.4, 163.9, 155.9, 144.3, 133.8, 79.9, 54.6, 32.8, 28.3, 18.8, 18.3.

e. Synthesis of Compound 210 (N-Boc Valine O-Benzyl Bisoxazole Amide)

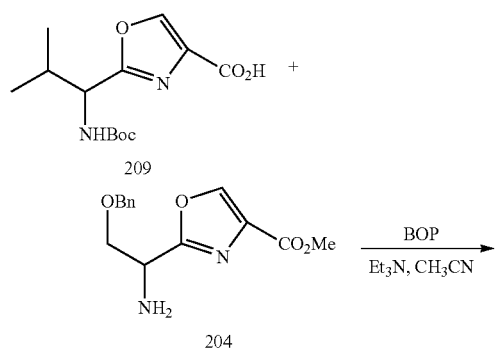

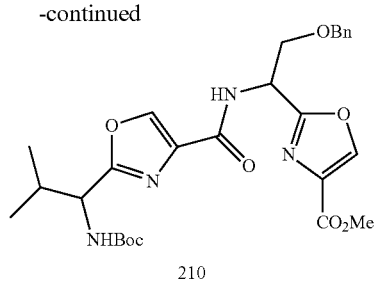

Dry acetonitrile (100 mL) was added to a mixture of amine 204 (3.24 g, 11.7 mmol) and acid 209 (3.33 g, 11.7 mmol) and stirred for 5 min BOP (5.17 g, 11.7 mmol) and triethylamine (3.6 mL, 25.7 mmol) were added and the mixture was stirred at room temperature for 12 h. The mixture was then evaporated under reduced pressure and diluted with EtOAc and brine. The phases were separated and then aqueous phase was extracted with EtOAc. The combined organic phases were then washed successively with 1N HCl, saturated NaHCO$_3$, and brine and then dried over Na$_2$SO$_4$, filtered and evaporated to give the amide as a colorless oil, 4.76 g (90%); $^1$H NMR (CDCl$_3$) δ 8.34 (s, 1H), 8.22 (s, 1H), 7.91 (d, 1H, J=8.4), 7.42 (m, 5H), 5.73 (m, 1H), 5.53 (m, 1H), 4.87 (m, 1H), 4.68 (s, 2H), 4.18 (m, 2H), 4.01 (s, 3H), 2.28 (m, 1H), 1.58 (s, 9H), 1.08 (d, 3H, J=6.6), 1.04 (d, 3H, J=7.0); $^{13}$C-NMR δ 163.2, 161.9, 161.8, 160.5, 159.5, 154.5, 143.4, 140.6, 136.4, 134.4, 132.5, 127.5, 126.9, 126.7, 79.1, 72.2, 68.9, 53.4, 51.2, 46.4, 31.7, 27.4, 17.9, 17.2.

f. Synthesis of Compound 211 (N-Boc Valine Serine Amide)

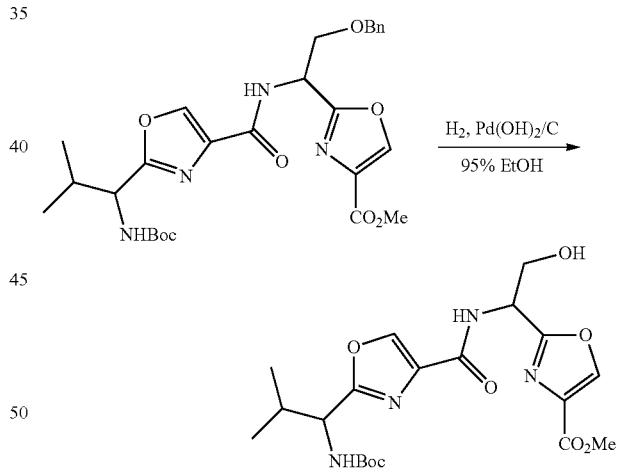

A solution of benzyl ether 9 (5.72 g, 10.6 mmol) in 95% EtOH (75 mL) was treated with 20% Pd(OH)$_2$/C (572 mg) and shaken in a Parr apparatus under 35 psi H$_2$ for 30 h at room temperature. The catalyst was filtered through a pad of Celite and the solvent was evaporated to give the alcohol as a colorless oil, 4.54 g (95%); $^1$H NMR (CDCl$_3$) δ 8.69 (d, 1H, J=8.2), 8.36 (s, 1H), 8.29 (s, 1H), 6.19 (d, 1H, J=6.2), 5.66 (m, 1H), 4.77 (m, 1H), 4.33 (m, 2H), 3.97 (s, 3H), 2.25 (m, 1H), 1.55 (s, 9H), 1.04 (d, 3H, J=6.6), 0.89 (d, 3H, J=6.6); $^{13}$C-NMR δ 163.2, 162.9, 161.9, 160.7, 160.5, 160.4, 154.7, 143.5, 140.9, 140.5, 134.2, 132.1, 127.4, 79.2, 61.7, 53.4, 51.4, 49.1, 48.3, 31.7, 30.8, 27.4, 18.2, 17.9, 17.3, 17.1.

g. Synthesis of Compound 212 (N-Boc Valine Dihydroteroxazole)

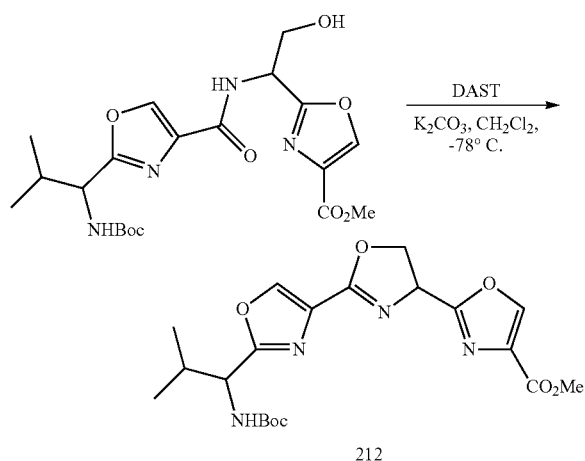

212

A solution of 211 (4.54 g, 10 mmol) in CH$_2$Cl$_2$ (20 mL) was cooled to −78° C. under nitrogen and treated with DAST (2.17 mL, 16.6 mmol). After stirring for 1.5 h anhydrous K$_2$CO$_3$ was added and the mixture was then allowed to warm to room temperature. The mixture was poured into saturated NaHCO$_3$ and extracted several times with CH$_2$Cl$_2$. The combined extracts were dried over Na$_2$SO$_4$, filtered and concentrated to give crude oxazoline 212 as a red-yellow foam, 3.44 g (79%, crude); $^1$H NMR (CDCl$_3$) δ 8.30 (s, 1H), 8.18 (s, 1H), 5.59 (m, 2H), 4.84 (m, 3H), 3.91 (s, 3H), 2.19 (m, 1H), 1.42 (s, 9H), 0.91 (d, 6H, J=6.8); $^{13}$C-NMR δ 164.4, 162.1, 162.0, 160.3, 159.2, 154.3, 143.9, 140.7, 132.3, 128.7, 78.7, 69.7, 53.2, 51.2, 31.9, 27.2, 17.7, 16.9.

h. Synthesis of Compound 213 (N-Boc Valine Teroxazole Ester)

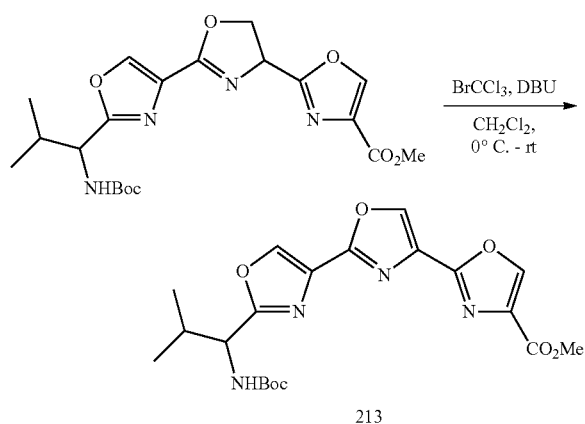

213

A solution of the crude oxazoline (3.44 g, 7.9 mmol) in dry CH$_2$Cl$_2$ (24 mL) was stirred under nitrogen at 0° C. as dry DBU (1.8 mL, 12.5 mmol) was added over 2 min followed by BrCCl$_3$ (1.2 mL, 12.5 mmol) which was then added over 5 min. The reaction was stirred at 0° C. for 5 h and was then poured into saturated NH$_4$Cl. The mixture was extracted with CH$_2$Cl$_2$ and the combined extracts were dried over Na$_2$SO$_4$, filtered, and evaporated. The product was purified by flash chromatography on silica gel eluting with 2:3 EtOAc/hexane to give the oxazole as a white solid, 1.64 g (48%); mp 214-224° C.; $^1$H NMR (CDCl$_3$) δ 8.58 (s, 1H), 8.48 (s, 1H), 8.46 (s, 1H), 5.53 (d, 1H, J=9.0), 4.95 (m, 1H), 4.08 (s, 3H), 2.35 (m, 1H), 1.56 (s, 9H), 1.07 (d, 6H, J=6.6); $^{13}$C NMR δ 164.8, 160.4, 154.5, 143.1, 138.5, 133.4, 129.9, 128.7, 79.1, 53.4, 51.4, 31.9, 27.4, 17.8, 17.1.

i. Synthesis of Compound 214 (N-Boc Valine Teroxazole Carboxylic Acid)

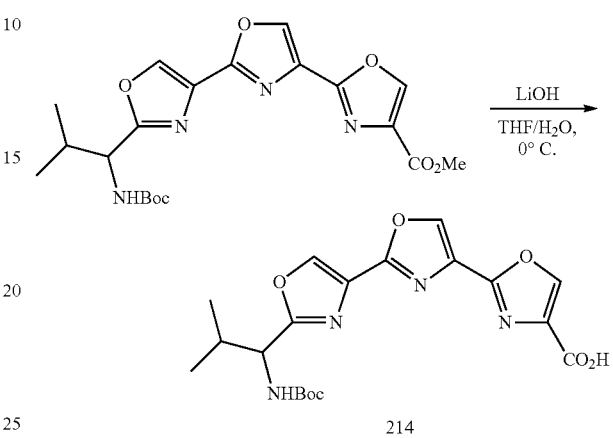

214

A solution of the ester (0.82 g, 1.9 mmol) in 3:1 THF/H$_2$O (32 mL) was stirred at 0° C. as LiOH (126 mg, 3 mmol) was added in one portion. The reaction mixture was stirred for 10 h and was then evaporated under reduced pressure to remove THF. The aqueous solution was brought to pH 3 with 1N HCl and was then extracted with EtOAc. The organic phase was washed with brine and dried over Na$_2$SO$_4$, filtered and evaporated to give the carboxylic acid as a white solid, 0.77 g (98%); mp 225° C. (dec.); $^1$H NMR (CDCl$_3$) δ 8.44 (s, 1H), 8.39 (s, 1H), 8.32 (s, 1H), 5.39 (d, 1H, J=8.4), 4.85 (m, 1H), 2.25 (m, 1H), 1.44 (s, 9H), 0.95 (d, 6H, J=6.0); $^{13}$C NMR δ 164.8, 160.4, 154.5, 143.1, 138.5, 133.4, 129.9, 128.7, 80.1, 51.4, 31.9, 27.4, 17.8, 17.1.

j. Synthesis of Compound 215 (Amino Valine Teroxazole Ester)

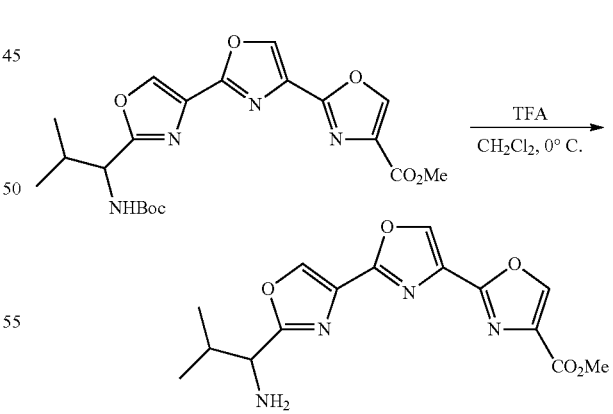

215

A solution of the N-Boc derivative (0.82 g, 1.9 mmol) in CH$_2$Cl$_2$ (10 mL) was cooled to 0° C. under protection from moisture by a drying tube. TFA (10 mL) was added and the solution was stirred for 1.5 h. Solvents were evaporated under reduced pressure and residual TFA was removed as an azeotrope with benzene. The residue was taken up in CH$_2$Cl$_2$ and washed with saturated NaHCO₃ and was then dried over Na₂SO₄, filtered, and evaporated to give the amine as a yellow-white solid, 0.62 g (98%); ¹H NMR (CDCl₃) δ 8.52 (s, 1H), 8.42 (s, 2H), 3.98 (s, 3H), 3.90 (m, 1H), 2.34 (m, 1H), 0.97 (d, 6H, J=6.6); ¹³C-NMR δ 163.5, 160.2, 155.1, 154.4, 154.1, 142.9, 138.6, 138.4, 133.4, 129.8, 128.8, 55.8, 51.9, 33.4, 18.9, 17.8.

The intermediate 204 can be prepared as follows.

k. Synthesis of Compound 201

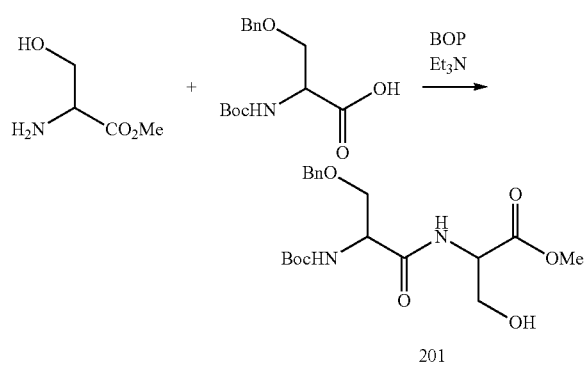

Boc-O-benzyl-L-serine (4.13 g, 14 mmol), serine methyl ester (2.18 g, 14 mmol) and BOP (6.19 g, 14 mmol) were dissolved in CH₃CN (40 mL). Then triethylamine (4.2 mL, 30.8 mmol, 2.2 eq) was added. The reaction stirred overnight at room temperature. The solvent was removed and the residue was dissolved in CH₂Cl₂ and washed successively with brine, 2N HCl, 0.5N NaHCO₃, water and brine. The organic extract was dried over Na₂SO₄ and concentrated to a clear oil weighing 5.54 g, 100%. ¹H NMR (CDCl₃) δ 7.31 (s, 6H), 5.49 (d, 1H, J=6), 4.64 (m, 1H), 4.55 (s. 2H), 4.31 (m, 1H), 3.88 (dd, 1H J=5, 10), 3.75 (s, 3H), 3.63 (dd, 1H J=6, 10), 2.96 (br s, 1H), 1.44 (s, 9H). ¹³C NMR (CDCl₃) δ 170.5, 170.3, 155.5, 137.2, 128.3, 127.8, 127.8, 127.7, 80.5, 73.3, 69.8, 69.4, 62.6, 62.4, 60.3, 54.8, 52.5, 28.1. IR (thin film NaCl) 3419, 3065, 3032, 2979, 2954, 2871, 2251, 1670, 1498, 1455, 1439, 1392, 1368, 1248, 1167, 1105, 1027 cm⁻¹. HRMS (FAB) m/z calcd for C₁₉H₂₈N₂O₇Li (M+Li) 403.2057; found, 403.2052.

l. Synthesis of Compound 202 (Serine Oxazoline)

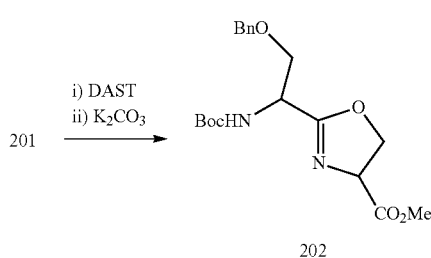 [SMILES: COC(=O)C1COC(C(COCc2ccccc2)NC(=O)OC(C)(C)C)=N1]

Compound 201 (5.54 g, 14 mmol) was dissolved in CH₂Cl₂ (20 mL) and placed under argon. After cooling to −78° C., DAST (2.8 mL 21.4 mmol, 1.5 eq) was added and the reaction stirred at low temperature for 2.5 hours. Then K₂CO₃ 2.9 g, 21.4 mmol, 1.5 eq) was added and the reaction warmed to room temperature. This was poured into saturated NaHCO₃. The layers were separated and the aqueous was extracted with CH₂Cl₂. The organic extracts were dried over Na₂SO₄ and concentrated to an orange oil weighing 5.28 g, 99%. ¹H NMR (CDCl₃) δ 7.50 (m, 5H), 5.66 (m, 1H), 4.99 (dd, 1H, J=8, 10), 4.71 (m, 5H), 3.96 (m, 5H), 1.64 (s, 9H). ¹³C NMR (CDCl₃) δ 170.2, 167.4, 154.3, 136.9, 134.2, 127.5, 126.8, 126.6, 79.0, 72.2, 69.2, 69.0, 67.2, 67.1, 52.5, 51.7, 48.5, 24.7. IR (neat NaCl) 3384, 3063, 3030, 2977, 2870, 1709, 1666, 1506, 1454, 1367, 1322, 1166, 1109, 1051 cm⁻¹.

m. Synthesis of Compound 203 (Boc-O-Benzyl Serine Oxazole)

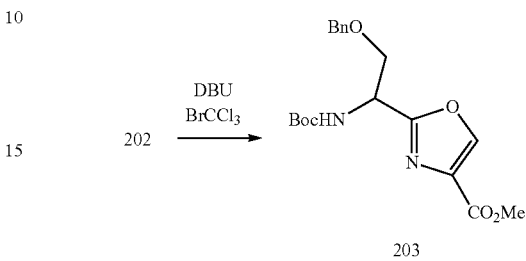

Oxazoline 202 (5.28 g, 14 mmol) in CH₂Cl₂ (20 mL) was placed under argon and cooled to 0° C. DBU (3.2 mL, 2 mmol, 1.6 eq) was added dropwise and the solution turned yellow. Then BrCCl₃ (2.2 mL, 22.4 mmol) was added dropwise and the solution became brown. This warmed to room temperature overnight and then poured into saturated ammonium chloride. The aqueous layer was extracted with CH₂Cl₂. The organic layers were dried over Na₂SO₄ and concentrated to a brown oil. This was flash chromatographed on SiO₂ with 15-50% EtOAc/hexane. The product was obtained as a clear oil 3.10 g, 59%. [α]²⁵_D-33.35 (c=2 g/100 mL in EtOH). ¹H NMR (CDCl₃) δ 8.36 (s, 1H) 7.41 (m, 5H), 5.76 (d, 1H, J=8), 5.30 (m, 1H), 4.66 (s, 2H), 4.07 (m, 3H), 3.97 (m, 2H), 1.61 (s, 9H). ¹³C NMR (CDCl₃) δ 163.4, 161.3, 154.9, 144.0, 137.2, 133.3, 128.2, 127.7, 127.4, 80.1, 73.1, 70.3, 52.0, 49.2, 28.1. IR (thin film NaCl) 3351, 3163, 3064, 3031, 2978, 2953, 2870, 2251, 1717, 1585, 1499, 1454, 1439, 1392, 13677, 1324, 1251, 1202, 1168, 1112, 1047, 1001 cm⁻¹.

n. Synthesis of Compound 204

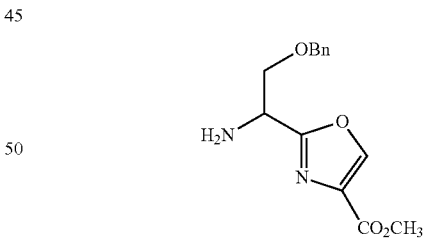

The Boc-protected serine oxazole (3.64 g, 9.68 mmol) was dissolved in dry CH₂Cl₂ (10 mL) and cooled to 0° C. This solution was treated with TFA (10 mL) and stirred for 6.5 hours. Solvent was removed in vacuo under aspirator pressure. Resulting dark brown residue was azeotroped with benzene (×2) and then dissolved in CH₂Cl₂ and poured into saturated sodium bicarbonate. Extracted with CH₂Cl₂ (4×15 mL) The organic layers were combined, dried over Na₂SO₄, filtered, and concentrated to a dark brown oil (2.65 g, 99% isolated yield). ¹H NMR (CDCl₃) δ 8.19 (s, 1H), 7.31 (m, 5H), 4.54 (s, 2H), 4.30 (m, 1H), 3.92 (s, 3H), 3.80 (dd, 2H, J=4.4, 9.5 Hz), 1.64 (br s, 2H); ¹³C NMR (CDCl₃) δ 170.2, 167.6, 143.2, 136.8, 132.4, 127.6, 126.9, 126.8, 72.5, 71.6, 51.3, 49.5; IR (neat) 3378, 3308, 3160, 3030, 2952, 2865, 1740 cm$^{-1}$.

EXAMPLE 4

Synthesis of Compound 258

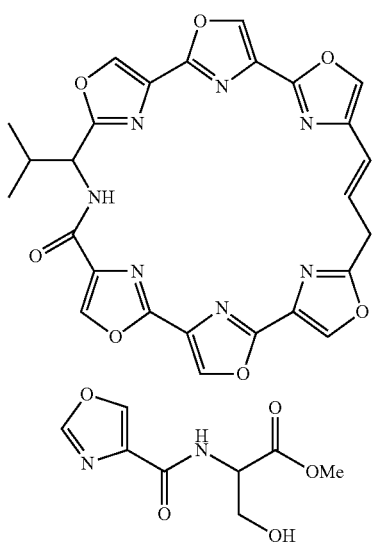

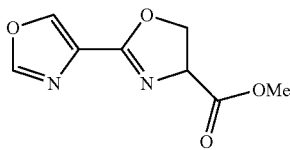 [SMILES: COC(=O)C1COC(c2cocn2)=N1]

Methyl 3-hydroxy-2-(oxazole-4-carboxamido)propanoate (244). Oxazole-4-carboxylic acid (3.88 g, 34.4 mmol), serine methyl ester (5.35 g, 34.4 mmol), EDC (13.2 g, 68.8 mmol) and HOBT (9.31 g, 68.8 mmol) were dissolved in dry DMF (100 mL) and placed under argon and 2,6-lutidine (2.8 mL, 172 mmol) was then added. The reaction was stirred at room temperature overnight after which solvent was removed by Kugelrohr distillation (50° C., 5 mm Hg). The residue was partitioned between ethyl acetate and water. The layers were separated and the organic layer was washed sequentially with saturated sodium bicarbonate, 5% HCl, and brine. The extract was dried with Na$_2$SO$_4$ and evaporated under reduced pressure to give a white solid, 6 g, 81%; mp 87-89° C.; $^1$H NMR (CDCl$_3$) δ 4.52 (d, 1H, J=1.1), 7.86 (m, 2H), 4.84 (dt, 1H, J=3.7, 8.1), 4.55 (br s, 1H), 4.06 (ddd, 2H, J=4, 8.8, 11.4) 3.8 (s, 3H); $^{13}$C NMR (CDCl$_3$) δ 669.6, 159.8, 149.9, 141.1, 134.5, 125.7, 125.4, 116.4, 110.2, 62.1, 53.6, 51.9; IR (Nujol) 3419, 3379, 3189, 3160, 3140, 1753, 1650, 1638, 1594, 1508, 1376, 1282, 1226, 1182, 1131, 1109, 1065, 1034, 969, 897, 887, 859, 822, 766, 741, 604 cm$^{-1}$; HRMS (ESI) m/z calculated for C$_8$H$_{10}$N$_2$O$_5$Na (M+Na) 237.0487; found 237.0487.

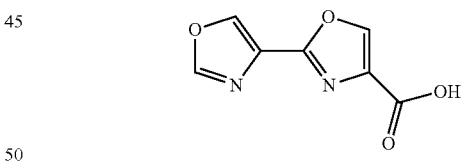

Methyl 2-(oxazol-4-yl)-4,5-dihydrooxazole-4-carboxylate(245). The amide 244 (6 g, 28 mmol) was dissolved in anhydrous CH$_2$Cl$_2$ and placed under argon. After cooling to −78° C., DAST was added (6.4 mL, 49 mmol) and the reaction stirred at low temperature for 4 h. Solid K$_2$CO$_3$ (6.77 g, 49 mmol) was then added and the reaction was warmed to room temperature. The reaction mixture was poured into saturated sodium bicarbonate solution and extracted with CH$_2$Cl$_2$. The organic extracts were dried with Na$_2$SO$_4$ and concentrated in vacuo to an orange oil weighing 3.72 g, 65%; $^1$H NMR (CDCl$_3$) δ 8.19 (s, 1H), 8.03 (s, 1H), 4.95 (dd, 1H, J=8, 11), 4.65 (m, 2H), 3.75 (s, 3H); $^{13}$C NMR (CDCl$_3$) δ 170.3, 159.4, 151.4, 140.7, 128.5, 69.4, 66.9, 51.8; IR (Thin film NaCl) 3655, 3408, 3227, 3150, 2997, 2957, 2910, 2849, 2244, 2197, 1740, 1678, 158:3, 1561, 1518, 1439, 1392, 1314, 1218, 1135, 1104, 1065, 981, 962, 935, 915, 844, 731, 650, 607, 558 cm$^{-1}$.

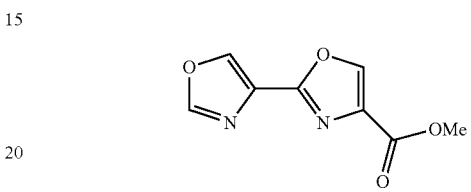

Methyl 2,4'-bioxazole-4-carboxylate(246). A solution of the oxazoline 245 (3.72 g, 19 mmol) in anhydrous CH$_2$Cl$_2$ was cooled to 0° C. under argon and treated dropwise with DBU (5.7 mL, 38 mmol) and then BrCCl$_3$ (5.2 mL, 53.2 mmol) both over a period of 10 min This was stirred and allowed to warm to room temperature overnight. The reaction mixture was poured into saturated ammonium chloride and extracted with CH$_2$Cl$_2$. After drying with Na$_2$SO$_4$, the organic solution was evaporated to a brown solid that was purified by flash chromatography on SiO$_2$ eluting with 100% CHCl$_3$ to 2% MeOH/CHCl$_3$. The product was obtained as a white solid, 2.77 g (75%); mp 177° C.; $^1$H NMR (CDCl$_3$) δ 8.44 (d, 1H, J=0.73), 8.34 (s, 1H), 8.05 (s, 1H), 3.96 (s, 3H); $^{13}$C NMR (CDCl$_3$) δ 160.5, 154.7, 151.1, 143.0, 138.9, 133.4, 128.7, 51.5; IR (Nujol) 3152, 3124, 2729, 1714, 1633, 1572, 1536, 1512, 1377, 1327, 1305, 1273, 1203, 1149, 1123, 1093, 1062, 999, 953, 917, 905, 849, 809, 775, 735, 668 cm$^{-1}$; HRMS (ESI) m/z calculated for C$_8$H$_6$N$_2$O$_4$Na (M+Na) 217.0225; found 217.0226.

2,4'-Bioxazole-4-carboxylic acid(247). A solution of the bis(oxazole) ester 246 (2.77 g, 14.2 mmol) in a 3:1 mixture of THF and water (200 mL) was cooled to 0° C. and treated with LiOH (721 mg, 17.2 mmol). The reaction was stirred and allowed to warm to room temperature overnight. The THF was removed under reduced pressure and the aqueous solution was treated with Amberlyst A-15 resin until the pH was 4. The resin was filtered and washed with MeOH. The filtrate was evaporated to yield a white solid, 2.49 g (97%); mp 240-243° C.; $^1$H NMR (DMSO-d$_6$) δ 8.98 (s, 1H), 8.85 (s, 1H), 8.66 (s, 1H); $^{13}$C NMR (DMSO-d$_6$) δ 161.6, 154.7, 153.3, 144.9, 140.6, 134.2, 128.5; IR (Nujol) 3134, 3096, 1684, 1642, 1561, 1542, 1509, 1377, 1313, 1257, 1226, 1172, 1123, 1108, 1093, 1061, 982, 954, 919, 851, 754, 732, 666, 616 cm$^{-1}$; HRMS (ESI) m/z calculated for C$_7$H$_4$N$_2$O$_4$Na (M+Na) 203.0069; found 203.0070.

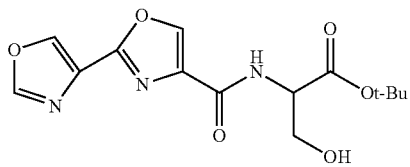 [SMILES: CC(C)(C)OC(=O)C(CO)NC(=O)c1coc(-c2cocn2)n1]

tert-Butyl 2-(2,4'-bioxazole-4-carboxamido)-3-hydroxypropanoate (248). A solution of the acid 247 from the previous reaction (2.49 g, 13.8 mmol), EDC (5.3 g, 27.7 mmol) and HOBT (3.74 g, 27.7 mmol) in anhydrous DMF (100 mL) was added to a solution of serine tert-butyl ester (2.23 g, 13.8 mmol) and 2,6-lutidine (16 mL, 138 mmol) in DMF (50 mL) at 0° C. under argon. This stirred and warmed to room temperature overnight. The solvent was removed by Kugelrohr distillation (50° C., 5 mm Hg) and the resulting residue was partitioned between EtOAc and $H_2O$. The layers were separated and the organic layer was washed with saturated sodium bicarbonate, 5% HCl, and brine. The organic layer was then dried with $Na_2SO_4$ and evaporated to a white solid, 3.32 g (74%); mp 85-87° C.; $^1$H NMR (CDCl$_3$) δ 8.30 (d, 1H, J=0.73), 8.27 (s, 1H), 8.09 (d, 1H, J=1.1), 7.85 (d, 1H, J=8), 4.73 (dt, 1H, J=3.7, 7.7), 4.03 (d, 2H, J=3.7), 1.48 (s, 9H); $^{13}$C NMR (CDCl$_3$) δ 168.2, 159.6, 153.7, 151.2, 140.6, 138.6, 136.0, 128.7, 81.9, 62.5, 54.4, 27.1; IR (Thin flim NaCl) 3397, 3143, 2979, 2942, 2252, 1734, 1663, 1597, 1514, 1463, 1397, 1369, 1236, 1158, 1121, 1067, 959, 909, 847, 733 cm$^{-1}$; HRMS (ESI) m/z calculated for $C_{14}H_{17}N_3O_6Na$ (M+Na) 346.1015; found 346.1014.

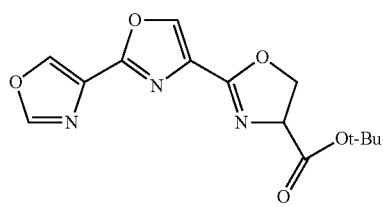 [SMILES: CC(C)(C)OC(=O)C1COC(c2coc(-c3cocn3)n2)=N1]

tert-Butyl 2-(2,4'-bisoxazol-4-yl)-4,5-dihydrooxazole-4-carboxylate(249). A solution of the amide 248 (3.32 g, 10.3 mmol) in $CH_2Cl_2$ (40 mL) was cooled to −78° C. under argon and treated with DAST (2 mL, 15.4 mmol). The reaction was stirred at that same temperature for 4 h and then solid $K_2CO_3$ (2.13 g, 15.4 mmol) was added. The reaction warmed to room temperature and was then poured into saturated NaHCO$_3$ solution. The layers were separated and the aqueous layer was extracted with $CH_2Cl_2$. The combined organic layers were dried over $Na_2SO_4$ and evaporated to an orange solid, 3.14 g (100%); mp 95-98° C.; $^1$H NMR (CDCl$_3$) δ 8.43 (d, 1H, J=0.73), 8.26 (s, 1H), 8.04 (d, 1H, J=1.1), 4.71 (m, 3H), 1.51 (s, 9H); $^{13}$C NMR (CDCl$_3$) δ 168.9, 158.5, 154.7, 151.0, 140.6, 140.4, 138.9, 138.7, 130.4, 128.8, 81.5, 69.2, 68.5, 27.1; IR (thin film NaCl) 3370, 3129, 3063, 2979, 2932, 1733, 1675, 1579, 1539, 1598, 1457, 1369, 1315, 1223, 1157, 1123, 1108, 1063, 988, 957, 908, 890, 845, 753, 715, 667 cm$^{-1}$; HRMS (ESI) m/z calculated for $C_{14}H_{15}N_3O_5Na$ (M+Na) 328.0909; found 328.0920.

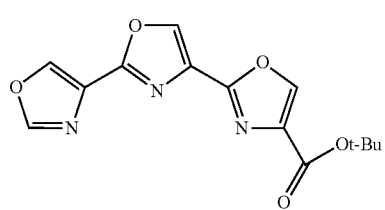 [SMILES: CC(C)(C)OC(=O)c1coc(-c2coc(-c3cocn3)n2)n1]

tert-Butyl teroxazole-4-carboxylate (250). The oxazoline 249 (3.14 g, 10.3 mmol) was dissolved in dry $CH_2Cl_2$ (30 mL) and placed under argon. After cooling to 0° C., the solution was treated dropwise with DBU (3.1 mL, 20.6 mmol) and then BrCCl$_3$ (2.4 mL, 24.7 mmol) over 10 min. The reaction was allowed to warm to room temperature overnight and was then poured into saturated aqueous NH$_4$Cl. The organic layer was separated and the aqueous solution was extracted with $CH_2Cl_2$. The combined organic layers were dried over $Na_2SO_4$ and evaporated under reduced pressure to afford a brown solid. Purification by flash chromatography on SiO$_2$ eluting with 100% CHCl$_3$ to 2% MeOH/CHCl$_3$ gave 1 as a white solid, 1.52 g (49%); mp 283° C. (dec.); $^1$H NMR (CDCl$_3$) δ 8.44 (s, 2H), 8.23 (s, 1H), 8.07 (d, 1H, J=0.74), 1.61 (s, 9H); $^{13}$C NMR (CDCl$_3$) δ 159.1, 155.0, 151.1, 142.3, 138.8, 138.5, 135.0, 130.2, 128.8, 81.6, 27.3; IR (thin film, NaCl) 3178, 3144, 2973, 2360, 2334, 1721, 1647, 1509, 1394, 1363, 1337, 1315, 1295, 1278, 1246, 1151, 1126, 1116, 1099, 1065, 987, 967, 956, 905, 832, 725 cm$^{-1}$; HRMS (ESI) m/z calculated for $C_{14}H_{13}N_3O_5Na$ (M+Na) 326.0753; found 326.0750.

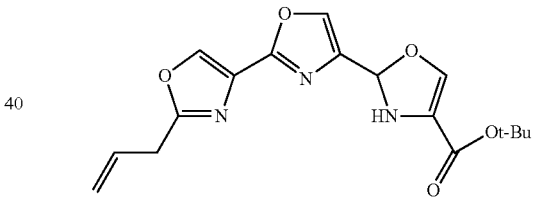

251 tert-Butyl 2"-allylteroxazole-4-carboxylate (251). To a solution of 250 (80 mg, 0.26 mmol) in anhydrous THF (7 mL) at −42° C. under a $N_2$ atmosphere was slowly added a solution of LiHMDS (528 µL, 1M in hexanes) via cannula. CuI (100 mg, 0.53 mmol) was added to the resulting yellow solution after it had stirred for 30 min at −42° C. After 5 min, allyl bromide (46 µL, 0.53 mmol) was added and the solution was stirred at −42° C. for 30 min. The solution was allowed to slowly warm to room temperature and was stirred overnight. Water (10 mL) was added and the solution was extracted with $CH_2Cl_2$ (2×20 mL). The organic layer was dried (Na$_2$SO$_4$), filtered, and concentrated. The crude product was purified by flash chromatography on SiO$_2$ eluting with 20% ethyl acetate in hexanes to afford the allylated product as a white solid, 32 mg, (37%); mp 277-279° C.; IR(CHCl$_3$) 1711 cm$^{-1}$; NMR (CDCl$_3$) δ 8.37 (s, 1H) 8.28 (s, 1H), 8.18 (s, 1H), 6.00 (m, 1H), 5.26 (m, 2H), 3.62 (d, 2H, J=6.6 Hz), 1.58 (s, 9H); $^{13}$C NMR (CDCl$_3$) δ 163.2, 159.1, 155.3, 154.3, 142.2, 138.5, 138.2, 134.9, 130.1, 129.5, 128.9, 118.2, 81.5, 31.6, 27.3; HRMS calcd for $C_{17}H_{17}N_3O_5Na$ (M+Na): 366.1066; found: 366.1065.

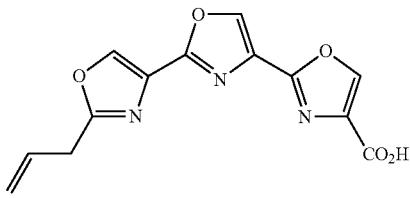

252

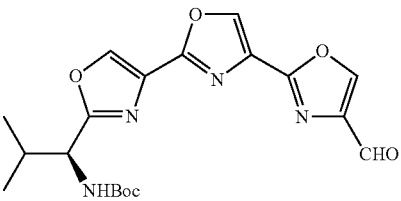

254

2"-Allylteroxazole-4-carboxylic acid (252). To an ice cold solution of the tert-butyl ester 251 (55 mg, 0.16 mmol) in CH$_2$Cl$_2$ (2 mL) was added anisole (400 μL) followed by TFA (2 mL) and the solution was stirred for 9 h at 0° C. The reaction mixture was concentrated in vacuo and the solid residue was triturated with diethyl ether (8×5 mL) and the solid was dried under high vacuum to give 252 as a white solid, 41 mg (89%); mp 283-285° C. (dec); IR(CHCl$_3$) 3135, 1686 cm$^{-1}$; $^1$H NMR (CDCl$_3$+CD$_3$OD) δ 8.38 (s, 1H) 8.27 (s, 1H), 8.26 (s, 1H), 5.91 (m, 1H), 5.19 (m, 2H), 3.55 (dt, 2H, J=1.4, 6.6 Hz); HRMS calcd for C$_{13}$H$_9$N$_3$O$_5$H (M+H): 288.0620; found: 288.0622.

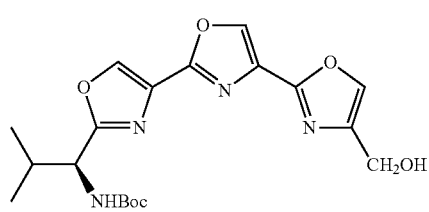

253

2"-[1-(tert-Butoxycarbonyl)amino-2-methylpropyl]-4-hydroxymethylteroxazole (253). To a solution of valine teroxazole 213 (100 mg, 0.23 mmol) in THF/EtOH (1:1, 20 mL) was added LiCl (59 mg, 1.39 mmol) followed by NaBH$_4$ (53 mg, 1.39 mmol). The solution was stirred at room temperature for 4 h and then water (10 mL) was added. THF and EtOH were removed under reduced pressure and the residue was further diluted with water (20 mL) and then acidified with acetic acid (pH ~6). The aqueous layer was extracted with chloroform (4×20 mL), dried over Na$_2$SO$_4$, filtered and the filtrate was evaporated in vacuo. The solid residue was purified by Chromatotron eluting with 2% MeOH in CHCl$_3$ to afford the title alcohol as a white solid, 68 mg (73%); mp 173-175° C.; IR(CHCl$_3$) 3430, 3326, 1705 cm$^{-1}$; 1H NMR (CDCl$_3$) δ 8.31 (s, 1H) 8.30 (s, 1H), 7.66 (s, 1H), 5.36 (d, 1H, J=9.2 Hz), 4.81 (dd, 1H, J=6.2, 9.0 Hz), 4.66 (s, 2H), 2.18 (m, 1H), 1.40 (s, 9H), 0.94 (d, 3H, J=4.0 Hz), 0.90 (d, 3H, J=3.6 Hz); $^{13}$C NMR (CDCl$_3$) δ 164.7, 155.1, 154.4, 154.2, 141.0, 138.4, 137.3, 134.3, 130.6, 128.8, 79.2, 55.9, 53.4, 31.9, 27.3, 17.8, 17.1; HRMS calcd for C$_{19}$H$_{24}$N$_4$O$_6$Na (M+Na): 427.1594; found: 427.1584.

2"-[1'-(tert-Butoxycarbonyl)amino-2-methylpropyl]-4-formylteroxazole (254). To a solution of oxalyl chloride (36 μL, 0.408 mmol) in CH$_2$Cl$_2$ (2 mL) at −78° C. under nitrogen was added DMSO (40 μL, 0.571 mmol) and the solution was stirred for ~10 min. A solution of the alcohol 253 from the previous reaction (33 mg, 0.081 mmol) in CH$_2$Cl$_2$ (5 mL) was added dropwise via cannula and stirred for 10 min at −78° C. Triethylamine (113 mL, 0.816 mmol) was added and the solution was allowed to warm to room temperature over 20 min with stirring. The reaction mixture was diluted with CH$_2$Cl$_2$ (20 mL) and washed with saturated NH$_4$Cl solution. The organic layer was separated and dried (Na$_2$SO$_4$), filtered and evaporated under reduced pressure. The residue was purified by Chromatotron eluting with 2% MeOH/CHCl$_3$ to yield aldehyde 254 as a white solid, 29 mg (88%); mp 196-198° C.; IR(CHCl$_3$) 3373, 1690 cm$^{-1}$; $^1$H NMR (CDCl$_3$) δ 10.0 (s, 1H), 8.38 (s, 1H) 8.33 (s, 1H), 8.32 (s, 1H), 5.29 (d, 1H, J=9.2 Hz), 4.83 (dd, 1H, J=6.2, 8.8 Hz), 2.23 (m, 1H), 1.42 (s, 9H), 0.94 (d, 3H, J=4.0 Hz), 0.92 (d, 3H, J=3.0 Hz); $^{13}$C NMR (CDCl$_3$) δ 183.1, 164.8, 155.5, 155.0, 154.4, 142.7, 140.7, 138.5, 138.4, 129.8, 128.7, 79.2, 53.4, 32.0, 27.4, 17.8, 17.1; HRMS calcd for C$_{19}$H$_{22}$N$_4$O$_6$Na (M+Na): 425.1437; found: 425.1432.

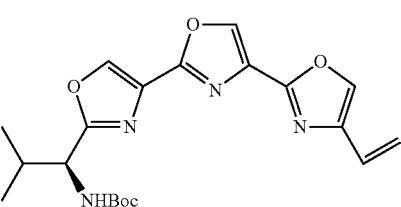

255

2"-[1-(tert-Butoxycarbonyl)amino-2-methylpropyl]-4-vinylteroxazole (255). A suspension of CH$_3$PPh$_3$Br (88 mg, 0.248 mmol) in anhydrous THF (5 mL) was cooled to 0° C. under nitrogen and n-BuLi (155 μL, 0.248 mmol, 1.6M in hexanes) was added dropwise via cannula. After stirring at 0° C. for 0.5 h the yellow solution was transferred to a solution of 254 (25 mg, 0.062 mmol) in THF (5 mL) at 0° C. via cannula and was allowed to warm to room temperature overnight while stirring. The reaction mixture was diluted with water (15 mL) and extracted with CHCl$_3$. The organic layer was dried over Na$_2$SO$_4$, filtered and evaporated under reduced pressure. The crude product was purified by flash chromatography eluting with 0.5% MeOH in CH$_2$Cl$_2$ to afford the vinyl derivative as a pale yellow solid, 18.3 mg (74%); mp 169-171° C.; IR(CHCl$_3$) 3364, 1706 cm$^{-1}$; $^1$H NMR (CDCl$_3$) δ 8.32 (s, 1H) 8.29 (s, 1H), 7.62 (s, 1H), 6.58 (dd, 1H, J=11, 17.4 Hz), 6.06 (d, 1H, J=17.4 Hz), 5.36 (d, 1H, J=11 Hz), 5.31 (d, 1H, J=10.2 Hz), 4.85 (app t, 1H, J=8.2 Hz), 2.21 (m, 1H), 1.44 (s, 9H), 0.96 (d, 3H, J=2.6 Hz), 0.93 (d, 3H, J=2.6 Hz); $^{13}$C NMR (CDCl$_3$) δ 164.7, 155.1, 154.5, 153.9, 139.6, 138.4, 137.5, 134.1, 130.8, 129.0, 123.8, 116.0, 79.2, 53.5, 32.1, 27.4, 17.8, 17.1; HRMS calcd for $C_{20}H_{24}N_4O_5Na$ (M+Na): 423.1644; found: 423.1631.

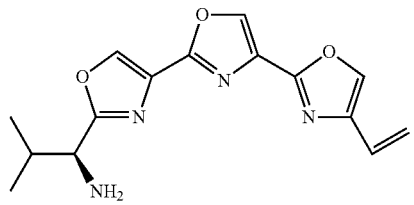

256

2"-(1-Amino-2-methylpropyl)-4-vinylteroxazole (256). The product from the previous reaction (60 mg, 0.15 mmol) was dissolved in $CH_2Cl_2$ (10 mL) at 0° C., treated with TFA (2.5 mL), and stirred at 0° C. for 6 h. The reaction mixture was evaporated under reduced pressure and the residue was diluted with saturated aqueous $NaHCO_3$ and extracted with $CH_2Cl_2$. The organic layer was separated and dried ($Na_2SO_4$), evaporated, and purified by flash chromatography to afford 256 as a white solid, 33 mg, (73%); mp 125-127° C.; IR($CHCl_3$) 3381 $cm^{-1}$; $^1H$ NMR ($CDCl_3$) δ 8.34 (s, 1H) 8.30 (s, 1H), 7.63 (s, 1H), 6.59 (dd, 1H, J=11, 17.4 Hz), 6.06 (d, 1H, J=17.4 Hz), 5.37 (d, 1H, J=11 Hz), 3.92 (d, 1H, J=6.6 Hz), 2.17 (m, 1H), 1.00 (d, 3H, J=5.6 Hz), 0.96 (d, 3H, J=7.0 Hz); $^{13}C$ NMR ($CDCl_3$) δ 167.4, 155.2, 153.9, 139.6, 138.3, 137.4, 134.1, 130.7, 128.7, 123.8, 116.0, 55.0, 32.5, 18.1, 17.1; HRMS calcd for $C_{15}Fl_{16}N_4O_3H$ (M+H): 301.1301; found: 301.1269.

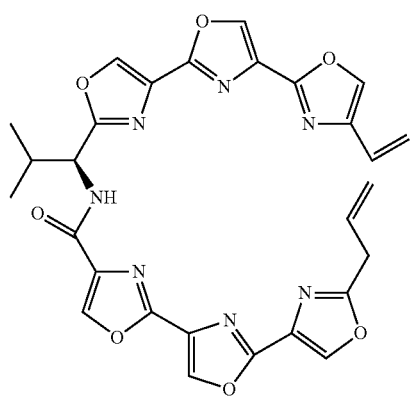

257

N-[2"-(2-Methylprop-1-yl)-4-vinylteroxazole]-2"-allylteroxazole-4-carboxamide (257). To a solution of 256 (10 mg, 0.033 mmol) in DMF (1 mL) at 0° C. under $N_2$ was added a solution of 252 (9.5 mg, 0.033 mmol), EDC HCl (13 mg, 0.066) and HOBt (9 mg, 0.066 mmol) in DMF (2 mL) and the mixture was stirred for 5 h at room temperature. Water (20 mL) was added and the mixture was extracted with EtOAc (3×25 mL). The organic layers were combined and dried over $Na_2SO_4$, filtered, and evaporated under reduced pressure. The residue was purified by flash chromatography eluting with 2% MeOH in $CH_2Cl_2$ to afford 257 as a white solid, 13 mg, (69%); mp 235-237° C. (dec); IR($CHCl_3$) 3363, 1653 $cm^{-1}$; $^1H$ NMR ($CDCl_3$) δ 8.34 (s, 2H) 8.33 (s, 1H), 8.30 (s, 1H), 8.26 (s, 1H), 7.62 (s, 1H), 7.59 (d, 1H, J=10.4 Hz), 6.57 (dd, 1H, J=11, 17.4 Hz), 6.01 (m, 2H), 5.32 (m, 4H), 3.64 (d, 2H, J=6.2 Hz), 2.41 (m, 1H), 1.07 (d, 3H, J=7.0 Hz), 1.00 (d, 3H, J=6.6 Hz); $^{13}C$ NMR ($CDCl_3$) δ 163.5, 163.3, 159.0, 155.6, 155.0, 153.9, 153.7, 140.7, 139.6, 138.6, 138.5, 138.2, 137.5, 135.9, 134.1, 130.7, 130.0, 129.5, 129.1, 128.8, 123.8, 118.3, 116.0, 51.6, 31.9, 31.6, 18.0, 17.5; HRMS calcd for $C_{28}H_{23}N_7O_7$-1 (M+H): 570.1737; found: 570.1732.

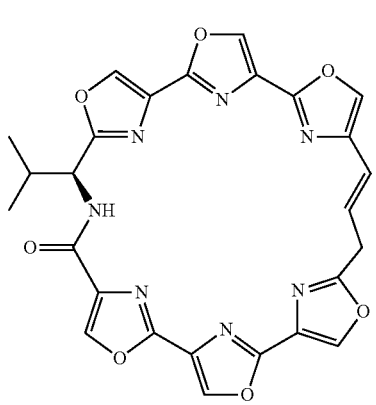

258

Macrocyclic Hexaoxazole (258). A 1.83 mM solution of 257 (13 mg, 0.022 mmol) and the second generation Grubb's catalyst (5.8 mg, 0.007 mmol) in $CH_2Cl_2$ (12 mL) was heated at reflux for 24 h. The reaction mixture was concentrated in vacuo and purified by Chromatotron eluting with 5% MeOH in $CHCl_3$ to afford 258 as an off white solid, 3 mg, (32%); mp 195-197° C. (dec); $[α]_D$=+2° (c 3.7, $CHCl_3$); IR($CHCl_3$) 3149, 1669, 1658 $cm^{-1}$; $^1H$ NMR ($CD_2Cl_2$, 400 MHz) δ 8.29 (d, 1H, J=8.4 Hz), 8.258 (s, 1H) 8.254 (s, 1H), 8.23 (s, 1H), 8.20 (s, 1H), 8.18 (s, 1H), 7.60 (m, 1H), 7.56 (s, 1H), 6.49 (d, 1H, J=15.6 Hz), 5.32 (m, 1H), 3.84 (ddd, 1H, J=2.4, 2.8, 19.4 Hz), 3.73 (ddd, 1H, J=8.4, 8.8, 20.2 Hz), 2.39 (m, 1H), 1.02 (d, 3H, J=6.8 Hz), 0.94 (d, 3H, J=6.8 Hz); $^{13}C$ NMR ($CDCl_3$) δ 163.4, 163.1, 159.1, 155.7, 154.9, 153.9, 153.8, 140.1, 139.0, 137.6, 137.40, 137.38, 136.29, 136.27, 132.7, 130.8, 130.2, 129.0, 128.9, 127.7, 118.0, 52.2, 33.0, 28.8, 17.7, 17.1; HRMS calcd for $C_{26}H_{19}N_7O_7$ (M+H): 542.1424; found: 542.1429.

EXAMPLE 5

Synthesis of Compound 259

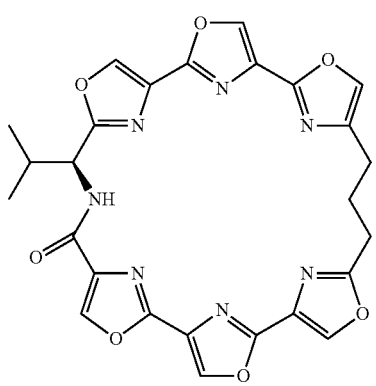

259

Compound 258 (5.5 mg, 0.01 mmol) and Wilkinson's catalyst (4.6 mg, 0.005 mmol) was taken in a round bottom flask fitted with stirring bar and rubber septa was placed under high vacuum for 0.5 h. Reaction flask was fitted with a hydrogen balloon, ethanol (6 mL) was added and stirred at room temperature for overnight. The reaction mixture was concentrated on rotavap and purified on chromatotron eluting with 8% methanol/chloroform to get a pale yellow solid in 49% yield; $[\alpha]_D=(-)2.4°$ (c 0.125, CHCl$_3$); IR (neat) 3381, 1655 cm$^{-1}$; $^1$H NMR (CDCl$_3$, 400 MHz) δ 8.61 (d, 1H, J=8.4 Hz), 8.20 (s, 1H) 8.14 (s, 2H), 8.10 (s, 1H), 8.07 (s, 1H), 7.42 (s, 1H), 5.28 (m, 1H), 2.94 (m, 1H), 2.85 (m. 1H), 2.64 (m, 3H), 2.42 (m, 1H), 2.35 (m, 1H), 1.04 (d, 3H, J=6.8 Hz), 0.97 (d, 3H, J=6.8 Hz); HRMS calcd for C$_{26}$H$_{21}$N$_7$O$_7$H (M+H): 544.1575; found: 544.1571.

EXAMPLE 6

Synthesis of Lysine Teroxazole Intermediate 309

A lysine teroxazole intermediate that can be used to prepare compounds of the invention can be prepared as follows a. Synthesis of Compound 301 (NBoc-Cbz Lysine)

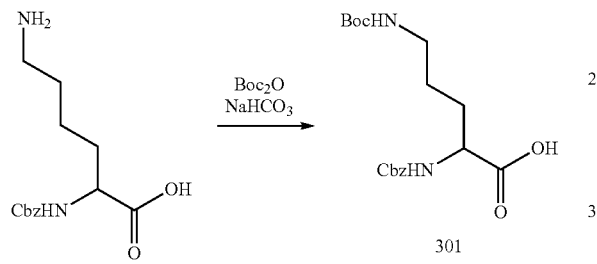

N-α-Cbz-(S)-Lysine (5 g, 17.85 mmol) was dissolved in a mixture of THF (50 mL) and water (50 mL). To this sodium bicarbonate (3 g, 35.5 mmol, 2 eq) and a solution of Boc$_2$O (9 g, 41 mmol, 2.3 eq) in THF (50 mL). After stirring at room temperature overnight, the THF was removed under reduced pressure and the resulting aqueous solution was neutralized with 2N HCl. This was extracted with ethyl acetate and the combined organic layers were washed with brine. The organic layer was dried with sodium sulfate and concentrated to a clear oil. Removal of excess Boc$_2$O by Kugelrhor distillation resulted in a thick clear oil weighing 6.8 g, 100%. $^1$H NMR (CDCl$_3$) δ 11.6 (s, 1H), 7.32 (s, 5H), 6.36 (s, 1H), 5.75 (d, 1H, J=8), 5.09 (s, 2H), 4.37 (m, 1H), 3.06 (m, 2H), 1.78 (m, 2H), 1.53 (s, 4H), 1.42 (s, 9H). $^{13}$C NMR (CDCl$_3$) δ 174.8, 155.4, 135.4, 127.6, 127.3, 127.2, 78.6, 66.1, 52.9, 39.2, 31.0, 28.6, 27.5, 26.6, 21.4.

b. Synthesis of Compound 302

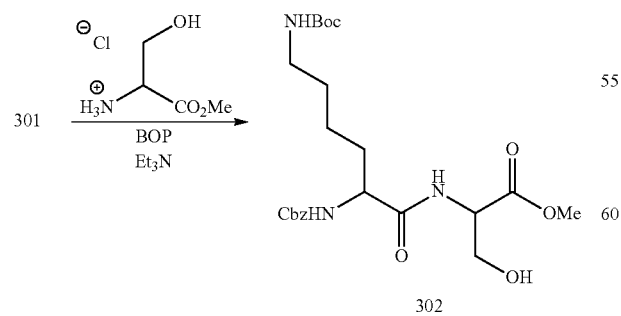

(DL)-serine methyl ester hydrochloride (2.78 g, 17.85 mmol 1 eq), BOP (7.9 g, 17.85 mmol, 1 eq) and 301 (6.8 g, 17.85 mmol) were dissolved in dry CH$_3$CN (100 mL). To this triethylamine (6.2 mL, 44.6 mmol, 2.5 eq) was added and the reaction stirred at room temperature overnight. The solvent was then removed in vacuo and the residue was taken up in ethyl acetate. This was washed successively with brine, 2N HCl, 0.5N NaHCO$_3$, water and brine. The organic layer was dried with sodium sulfate and concentrated to a clear oil weighing 8.6 g, 100%. $^1$H NMR (CDCl$_3$) δ 7.50 (m, 1H), 7.31 (s, 5H), 6.12 (m, 1H), 5.06 (m, 3H), 4.63 (m, 1H), 4.30 (m, 1H), 3.94 (m, 2H), 3.71 (s, 3H), 3.07 (m, 2H), 1.63 (m, 21-1), 1.43 (m, 11H). $^{13}$C NMR (CDCl$_3$) δ 171.6, 170.3, 170.0, 155.7, 135.3, 127.6, 127.2, 127.1, 78.3, 66.1, 61.6, 53.8, 51.7, 51.7, 39.0, 31.4, 31.2, 28.5, 27.5, 21.5. IR (thin film, NaCl) 3336, 3068, 3014, 2981, 2937, 2866, 1693, 1525, 1455, 1392, 1366, 1250, 1170, 1061, 912, 849, 755, 698, 666 cm$^{-1}$.

c. Synthesis of Compound 303 (Lysine Oxazoline)

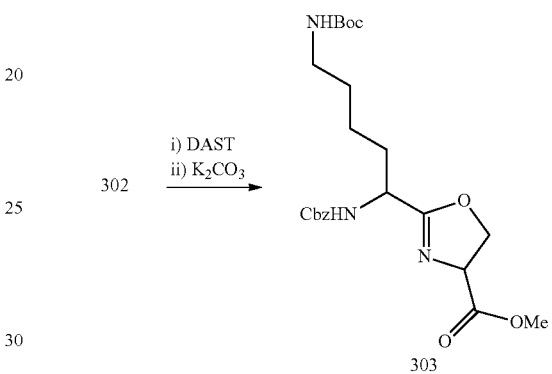

Compound 302 (8.6 g, 17.85 mmol) was dissolved in dry CH$_2$Cl$_2$ (40 mL) and placed under argon. After cooling to −78° C., DAST (3.5 mL, 26.8 mmol, 1.5 eq) was added. After stirring at low temperature for 4 hours, solid K$_2$CO$_3$ (3.7 g, 26.8 mmol, 1.5 eq) was added and the reaction warmed to room temperature. The reaction mixture was poured into saturated NaHCO$_3$ and the layers were separated. The aqueous layer was further extracted with CH$_2$Cl$_2$ and the combined organic layers were dried with sodium sulfate. Removal of solvent under reduced pressure afforded the oxazoline as an orange oil weighing 8.3 g, 99%. $^1$H NMR (CDCl$_3$) δ 7.34 (s, 5H), 5.67 (t, 1H, J=9), 5.10 (s, 2H), 4.73 (m, 2H) 4.46 (m, 3H), 3.77 (s, 3H), 3.00 (m, 2H), 1.75 (m, 214), 1.42 (s, 13H). $^{13}$C NMR(CDCl$_3$) δ 170.4, 170.3, 169.2, 168.8, 155.2, 154.9, 135.4, 127.6, 127.2, 78.1, 69.4, 69.2, 66.9, 66.8, 66.0, 51.8, 48.2, 39.3, 31.9, 31.8, 28.6, 27.5, 21.3, 21.1. IR (thin film, NaCl) 3349, 3069, 3034, 2981, 2953, 2866, 2249, 1705, 1666, 1519, 1455, 1439, 1392, 1366, 1337, 1249, 1174, 1060, 988, 912, 848, 777, 733, 698, 647 cm$^{-1}$.

d. Synthesis of Compound 304 (Lysine oxazole)

Compound 303 (8.3 g, 17.85 mmol) was dissolved in dry $CH_2Cl_2$ (40 mL) and placed under argon. This was cooled to 0° C. and treated dropwise with DBU (5.3 mL, 35.7 mmol, 2 eq) and $BrCCl_3$ (4.2 mL, 42.8 mmol, 2.4 eq) successively. The reaction mixture turned from orange to dark brown in color and was allowed to warm to room temperature overnight. It was then poured into a solution of saturated ammonium chloride and extracted with $CH_2Cl_2$. The organic layers were dried with sodium sulfate and concentrated to a brown oil. This was flash chromatographed on $SiO_2$ with 1-5% methanol/chloroform which gave the product as an amber oil weighing 7.0 g, 85%. $^1H$ NMR ($CDCl_3$) δ 8.18 (s, 1H), 7.31 (m, 6H), 5.71 (d, 1H, J=8), 5.10 (s, 2H), 5.00 (m, 1H), 4.61 (M, 1H), 3.90 (s, 3H), 3.08 (m, 2H), 1.90 (m, 2H), 1.41 (m, 12H). $^{13}C$ NMR ($CDCl_3$) δ 164.1, 160.5, 155.2, 154.9, 143.1, 135.3, 132.4, 127.6, 127.3, 127.2, 78.3, 76.4, 66.3, 51.3, 48.5, 39.1, 32.7, 28.6, 27.5, 21.5. IR (thin film, NaCl) 3337, 3167, 3069, 3034, 2975, 2952, 2866, 2250, 1705, 1585, 1523, 1455, 1439, 1392, 1366, 1325, 1249, 1170, 1111, 1044, 1002, 912, 863, 805, 733, 698, 647 $cm^{-1}$.

e. Synthesis of Compound 305 (Lysine Oxazole Acid)

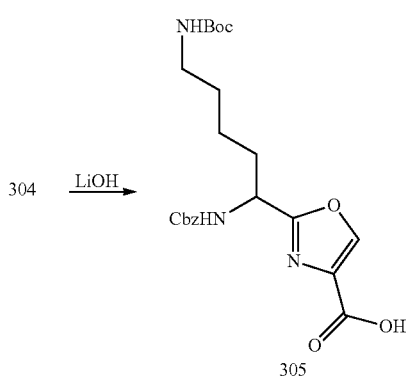 [SMILES: "LiOH" ; CC(C)(C)OC(=O)NCCCCC(NC(=O)OCc1ccccc1)c1nc(C(=O)O)co1]

Compound 304 (7.0 g, 15.23 mmol) was dissolved in a 3:1 mixture of THF and water (40 mL) and cooled to 0° C. To this LiOH (767 mg, 18.3 mmol, 1.2 eq) was added and the reaction warmed to room temperature overnight. After removing the solvent under vacuum, 1N HCl (22 mL) was added until the pH was slightly acidic. This was extracted with ethyl acetate and the combined organic layers were washed with brine. After drying with sodium sulfate, the organic phase was concentrated to a pale yellow, sticky solid weighing 5.9 g, 87%. Melting point 65-67° C. $^1H$ NMR ($CDCl_3$) δ 12.39 (s, 1H), 8.17 (s, 1H), 7.25 (m, 614), 6.52 (m, 1H), 5.08 (m, 3H), 4.69 (m, 1H), 3.09 (m, 2H), 1.92 (m, 2H), 1.42 (s, 12H). $^{13}C$ NMR ($CDCl_3$) δ 165.1, 162.7, 155.3, 143.7, 135.3, 132.5, 128.2, 127.6, 127.3, 127.2, 124.4, 78.5, 66.2, 48.5, 39.1, 32.7, 28.5, 27.5, 21.6. IR (thin film, NaCl) 3321, 2934, 2551, 2250, 1701, 1527, 1455, 1367, 1251, 1164, 1111, 1045, 982, 911, 860, 732, 697, 947 $cm^{-1}$. HRMS (FAB) m/z calcd for $C_{22}H_{29}N_3O_7Li$ (M+Li) 455.2194; found, 455.2179.

f. Synthesis of Compound 306 (TIPS Bisoxazole)

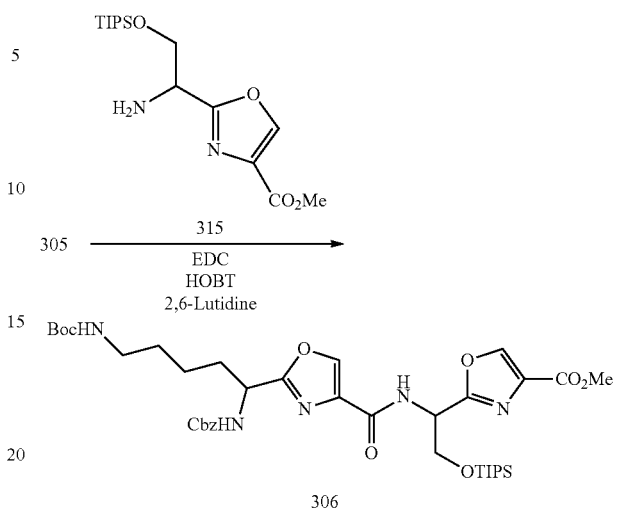

The TIPS oxazole 315 (synthesis outlined below) (3.58 g, 10.47 mmol) was dissolved in dry $CH_2Cl_2$ (20 mL) and placed under argon. To this was added freshly distilled 2,6-lutidine (6.1 mL, 52.4 mmol, 5 eq) and the flask was cooled to 0° C. Then a solution of 305 (4.68 g, 10.47 mmol, 1 eq), EDC (4.02 g, 20.94 mmol, 1.2 eq) and HOBT (2.83 g, 20.94 mmol, 1.2 eq) in $CH_2Cl_2$ (40 mL) was added. The reaction warmed to room temperature overnight and then the solvent was removed under reduced pressure. The residue was taken up in ethyl acetate and washed successively with saturated $NaHCO_3$, 5% HCl, water and brine. The organic phase was dried over sodium sulfate and concentrated to an orange oil weighing 7.04 g, 87%. $^1H$ NMR ($CDCl_3$) δ 8.20 (s, 1H), 8.10 (s, 1H), 7.39 (d, 1H, J=8), 7.35 (s, 6H), 5.66 (d, 1H, J=8), 5.46 (dt, 1H, J=5, 8), 5.11 (s, 2H), 4.97 (dt, 1H J=7, 7), 4.67 (dd, 111 J=4, 10), 4.20 (m, 3H), 3.79 (s, 3H), 3.90 (m, 2H), 1.90 (m, 2H), 1.42 (m, 11H), 1.02 (m, 21H). $^{13}C$ NMR ($CDCl_3$) δ 163.0, 162.5, 160.6, 159.2, 155.2, 154.9, 143.2, 140.6, 135.3, 134.7, 132.6, 127.6, 127.3, 127.3, 97.4, 78.5, 66.3, 63.9, 51.2, 48.4, 39.2, 32.5, 28.7, 27.5, 21.5, 17.2, 16.9, 12.1, 11.5, 10.9. IR (thin film, NaCl) 3295, 3034, 2944, 2866, 2250, 1712, 1599, 1520, 1461, 1391, 1366, 1324, 1249, 1204, 1171, 1115, 1045, 998, 912, 883, 843, 803, 733, 684, 647 $cm^{-1}$. HRMS (FAB) m/z calcd for $C_{38}H_{57}N_5O_{10}SiLi$ (M+Li) 778.4029; found 778.4053.

g. Synthesis of Compound 307 (Lysine Bisoxazole)

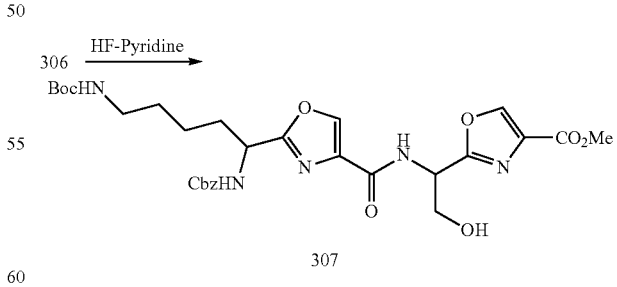

Compound 306 (7.2 g, 9.3 mmol) was dissolved in THF (50 mL) and pyridine (10 mL) This was treated dropwise with HF-pyridine complex (3 mL) during which a gas was evolved. The reaction stirred at room temperature for 18 hours and then slowly poured into saturated $NaHCO_3$. This was extracted with chloroform and dried with sodium sulfate. After concentrating and azeotroping with toluene, the product was obtained as an orange oil weighing 5.76 g, 100%. $^1$H NMR (CDCl$_3$) δ 9.09 (d, 1H, J=7), 8.26 (s, 1H), 8.21 (s, 1H), 7.30 (m, 6H), 6.63 (d, 1H, J=9), 5.46 (m, 1H), 5.08 (s, 2H), 4.68 (m, 2H), 4.26 (m, 2H), 3.86 (s, 3H), 3.07 (m, 2H), 1.43 (s, 12H). $^{13}$C NMR (CDCl$_3$) δ 162.9, 162.8, 160.8, 155.2, 143.4, 143.2, 135.4, 134.4, 132.1, 128.2, 127.7, 127.3, 127.2, 124.4, 78.3, 66.2, 63.8, 61.9, 51.5, 51.3, 49.4, 47.5, 39.3, 32.2, 31.2, 28.5, 27.5, 21.7. IR (thin film, NaCl) 3307, 3034, 2945, 2867, 2250, 1712, 1599, 1519, 1456, 1392, 1367, 1324, 1249, 1170, 1113, 1001, 911, 863, 805, 732, 697, 647 cm$^{-1}$.

h. Synthesis of Compound 308

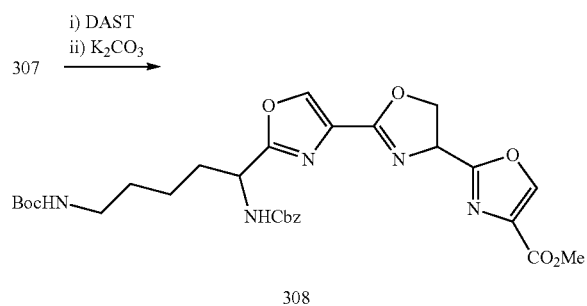

Compound 307 (2.76 g, 9.3 mmol) was dissolved in dry CH$_2$Cl$_2$ (40 mL) and placed under argon. After cooling to −78° C., DAST (1.8 mL, 13.95 mmol, 1.5 eq) was added and the reaction stirred at low temperature for 4 hours. This was followed by addition of solid K$_2$CO$_3$ (1.9 g, 13.95 mmol, 1.5 eq) and the mixture warmed to room temperature. The solution was poured into saturated NaHCO$_3$ and extracted with CH$_2$Cl$_2$. The combined organic layers were dried with sodium sulfate and concentrated to afford an orange oil weighing 5.58 g, 100%. $^1$H NMR (CDCl$_3$) δ 8.25 (s, 1H), 8.20 (s, 1H), 8.11 (d, 1H, J=3), 7.91 (d, 1H, J=10), 7.33 (s, 5H), 5.71 (d, 1H, J=9), 5.53 (m, 1H), 5.10 (s, 2H), 4.87 (m, 2H), 4.62 (m, 1H), 3.91 (s, 3H), 3.07 (m, 2H), 1.85 (m, 2H), 1.41 (s, 14H). $^{13}$C NMR (CDCl$_3$) δ 164.5, 163.0, 162.5, 162.1, 160.4, 159.3, 155.2, 144.0, 143.2, 140.9, 135.3, 134.7, 132.4, 129.1, 127.6, 127.3, 127.2, 78.3, 69.8, 66.2, 63.8, 62.8, 51.3, 48.4, 39.2, 35.5, 32.9, 28.7, 27.5, 21.5, 12.8. IR (thin film, NaCl) 3323, 3155, 3034, 2944, 2867, 2248, 1713, 1584, 1522, 1456, 1391, 1366, 1322, 1249, 1171, 1111, 1044, 995, 914, 885, 804, 775, 733, 698, 646 cm 1.

i. Synthesis of Compound 309 (Lysine Teroxazole)

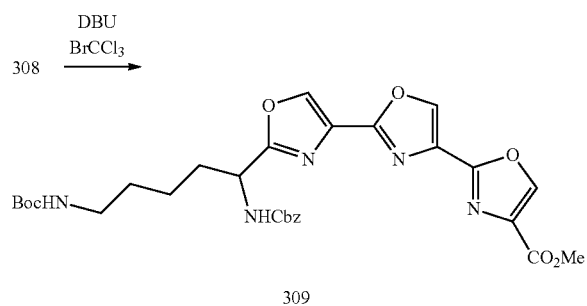

Compound 308 (5.58 g, 9.3 mmol) was dissolved in dry CH$_2$Cl$_2$ (40 mL) and placed under argon. The flask was cooled to 0° C. and DBU (2.8 mL, 18.6 mmol, 2 eq) and BrCCl$_3$ (2.2 mL, 22.3 mmol, 2.4 eq) were both added dropwise. This warmed to room temperature overnight and was then poured into saturated ammonium chloride solution. The layers were separated and the aqueous extracted with CH$_2$Cl$_2$. The combined organic layers were dried with sodium sulfate and concentrated to a brown oil. Flash chromatography on SiO$_2$ with 1-2% methanol/chloroform afforded a thick yellow oil. The product obtained from the column was recrystallized from benzene to give white sand like crystals weighing 2.52 g, 46%. Melting point 135-137° C.; Optical rotation [α]$_D^{22}$=−37° (c=1 g/100 mL in CHCl$_3$). $^1$H NMR (CDCl$_3$) δ 8.44 (s, 1H), 8.34 (s, 1H), 8.31 (s, 1H), 7.35 (m, 51-1), 5.68 (d, 1H, J=8), 5.12 (s, 21-1), 5.04 (m, 1H), 4.61 (m, 1H), 3.95 (s, 3H), 3.10 (m, 2H), 1.98 (m, 2H), 1.41 (s, 14H). $^{13}$C NMR (CDCl$_3$) δ 164.7, 160.4, 155.2, 155.1, 155.0, 154.5, 143.4, 143.0, 139.8, 138.7, 138.5, 135.2, 133.6, 130.0, 128.9, 127.6, 127.4, 127.3, 127.3, 78.3, 66.3, 57.6, 51.4. 48.6, 39.1, 32.7, 28.7, 27.5, 21.5. IR (nujol) 3325, 3156, 3117, 1721, 1689, 1644, 1578, 1518, 1377, 1327, 1247, 1116, 999, 976, 816, 805, 775, 725 cm$^{-1}$ HRMS (FAB) m/z calcd for C$_{29}$H$_{33}$N$_5$O$_9$Li (M+Li) 602.2433; found 602.2436.

The intermediate Compound 315 used in step f above was prepared as follows.

p. Synthesis of Compound 310

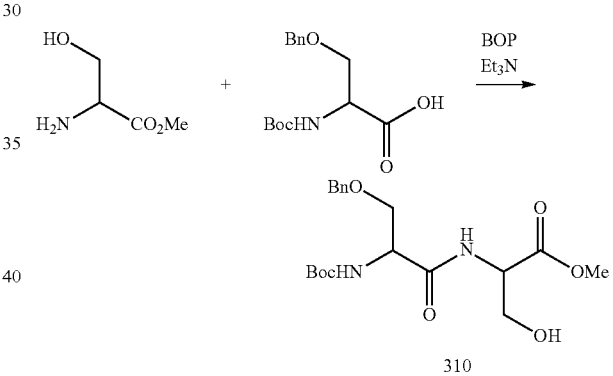

Boc-O-benzyl-L-serine (4.13 g, 14 mmol), serine methyl ester (2.18 g, 14 mmol) and BOP (6.19 g, 14 mmol) were dissolved in CH$_3$CN (40 mL) Then triethylamine (4.2 mL, 30.8 mmol, 2.2 eq) was added. The reaction stirred overnight at room temperature. The solvent was removed and the residue was dissolved in CH$_2$Cl$_2$ and washed successively with brine, 2N HCl, to 0.5N NaHCO$_3$, water and brine. The organic extract was dried over Na$_2$SO$_4$ and concentrated to a clear oil weighing 5.54 g, 100%. $^1$H NMR (CDCl$_3$) δ 7.31 (s, 6H), 5.49 (d, 1H, J=6), 4.64 (m, 1H), 4.55 (s, 2H), 4.31 (m, 1H), 3.88 (dd, 1H J=5, 10), 3.75 (s, 3H), 3.63 (dd, 1H J=6, 10), 2.96 (br s, 1H), 1.44 (s, 9H). $^{13}$C NMR (CDCl$_3$) δ 170.5, 170.3, 155.5, 137.2, 128.3, 127.8, 127.8, 127.7, 80.5, 73.3, 69.8, 69.4, 62.6, 62.4, 60.3, 54.8, 52.5, 28.1. IR (thin film NaCl) 3419, 3065, 3032, 2979, 2954, 2871, 2251, 1670, 1498, 1455, 1439, 1392, 1368, 1248, 1167, 1105, 1027 cm$^{-1}$. HRMS (FAB) m/z calcd for C$_{19}$H$_{28}$N$_2$O$_7$Li (M+Li) 403.2057; found, 403.2052.

q. Synthesis of Compound 311 (Serine Oxazoline)

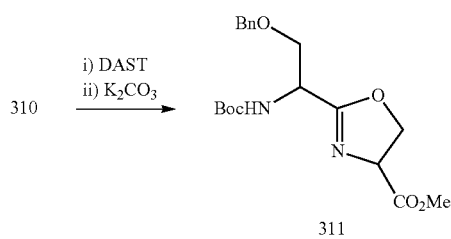 [SMILES: COC(=O)C1COC(C(COCc2ccccc2)NC(=O)OC(C)(C)C)=N1]

Compound 310 (5.54 g, 14 mmol) was dissolved in CH$_2$Cl$_2$ (20 mL) and placed under argon. After cooling to −78° C., DAST (2.8 mL 21.4 mmol, 1.5 eq) was added and the reaction stirred at low temperature for 2.5 hours. Then K$_2$CO$_3$ 2.9 g, 21.4 mmol, 1.5 eq) was added and the reaction warmed to room temperature. This was poured into saturated NaHCO$_3$. The layers were separated and the aqueous was extracted with CH$_2$Cl$_2$. The organic extracts were dried over Na$_2$SO$_4$ and concentrated to an orange oil weighing 5.28 g, 99%. $^1$H NMR (CDCl$_3$) δ 7.50 (m, 5H), 5.66 (m, 1H), 4.99 (dd, 1H, J=8, 10), 4.71 (m, 5H), 3.96 (m, 5H), 1.64 (s, 9H). $^{13}$C NMR (CDCl$_3$) δ 170.2, 167.4, 154.3, 136.9, 134.2, 127.5, 126.8, 126.6, 79.0, 72.2, 69.2, 69.0, 67.2, 67.1, 52.5, 51.7, 48.5, 24.7. IR (neat NaCl) 3384, 3063, 3030, 2977, 2870, 1709, 1666, 1506, 1454, 1367, 1322, 1166, 1109, 1051 cm$^{-1}$.

r. Synthesis of Compound 312 (Boc-O-Benzyl Serine Oxazole)

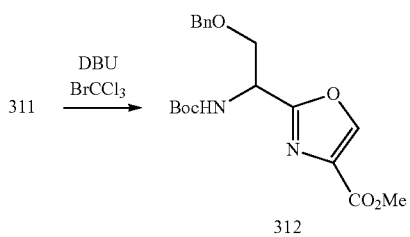 [SMILES: COC(=O)c1coc(C(COCc2ccccc2)NC(=O)OC(C)(C)C)n1]

Oxazoline 311 (5.28 g, 14 mmol) in CH$_2$Cl$_2$ (20 mL) was placed under argon and cooled to 0° C. DBU (3.2 mL, 2 mmol, 1.6 eq) was added dropwise and the solution turned yellow. Then BrCCl$_3$ (2.2 mL, 22.4 mmol) was added dropwise and the solution became brown. This warmed to room temperature overnight and then poured into saturated ammonium chloride. The aqueous layer was extracted with CH$_2$Cl$_2$. The organic layers were dried over Na$_2$SO$_4$ and concentrated to a brown oil. This was flash chromatographed on SiO$_2$ with 15-50% EtOAc/hexane. The product was obtained as a clear oil 3.10 g, 59%. [α]$^{25}_D$ −33.35 (c=2 g/100 mL in EtOH). $^1$H NMR (CDCl$_3$) δ 8.36 (s, 1H) 7.41 (m, 5H), 5.76 (d, 1H, J=8), 5.30 (m, 1H), 4.66 (s, 2H), 4.07 (m, 3H), 3.97 (m, 2H), 1.61 (s, 9H). $^{13}$C NMR (CDCl$_3$) δ 163.4, 161.3, 154.9, 144.0, 137.2, 133.3, 128.2, 127.7, 127.4, 80.1, 73.1, 70.3, 52.0, 49.2, 28.1. IR (thin film NaCl) 3351, 3163, 3064, 3031, 2978, 2953, 2870, 2251, 1717, 1585, 1499, 1454, 1439, 1392, 13677, 1324, 1251, 1202, 1168, 1112, 1047, 1001 cm$^{-1}$.

s. Synthesis of Compound 313 (Boc Serine Oxazole Alcohol)

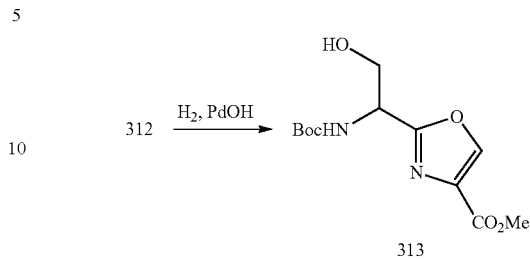

Compound 312 (3.10 g, 8.24 mmol) was dissolved in methanol (50 mL) and 20% palladium hydroxide on carbon (500 mg) was added to the reaction vessel. This was hydrogenated in a Parr hydrogenator at 40 psi for 72 hours. The reaction mixture was filtered through Celite while washing with methanol. The filtrate concentrated to a clear oil weighing 1.71 g, 75% (some material lost in hydrogenator). $^1$H NMR (CDCl$_3$) δ 8.21 (s, 1H), 5.67 (s, 1H), 5.02 (s, 1H), 3.96 (m, 5H), 1.45 (s, 9H). $^{13}$C NMR (CDCl$_3$) δ 143.5, 79.7, 62.8, 51.4, 49.8, 27.4 IR (thin film, NaCl) 3364, 2979, 2251, 1716, 1585, 1519, 1456, 1440, 1393, 1368, 1324, 1252, 1168, 1112, 1061, 1001, 915, 861, 804, 774, 733 cm$^{-1}$.

t. Synthesis of Compound 314 (Boc-O-TIPS Serine Oxazole)

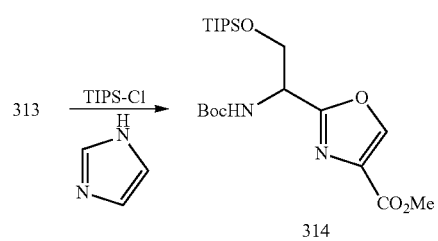

Compound 313 (1.71 g, 6 mmol) was dissolved in dry DMF (15 mL) and imidazole (1.02 g, 15 mmol, 2.5 eq) was added to the flask. This was placed under argon and treated with TIPS-Cl (1.52 mL, 7.2 mmol, 1.2 eq). The reaction stirred at room temperature overnight and then poured into water. This was extracted with ethyl acetate and the combined organic layers were washed with brine and dried with sodium sulfate. Concentration afforded yellow oil that was flash chromatographed on SiO$_2$ with 5-15% ethyl acetate/hexane. This was concentrated to a clear oil weighing 1.9 g, 72%. $^1$H NMR (CDCl$_3$) δ 8.20 (s, 1H), 5.58 (d, 1H, J=8), 5.03 (m, 1H), 4.09 (dq, 2H, J=3, 19), 3.92 (s, 3H), 1.17 (m, 3H), 1.07 (s, 9H), 1.02 (m, 18H). $^{13}$C NMR (CDCl$_3$) δ 169.3, 169.1, 163.0, 160.7, 143.1, 132.5, 79.3, 64.1, 51.3, 50.4, 27.4, 17.0, 11.5. IR (thin film NaCl) 3447, 3353, 3159, 3112, 2944, 2892, 2867, 2756, 2723, 2251, 1720, 1585, 1500, 1463, 1391, 1367, 1324, 1250, 1171, 1113, 1068, 998, 920, 882, 804, 766, 733, 684, 660 u. Synthesis of Compound 315 (TIPS Serine Oxazole Amine)

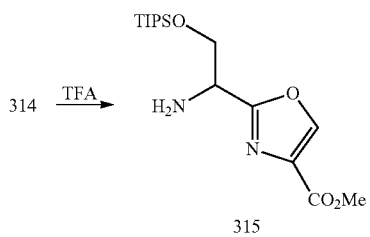

Compound 314 (1.9 g, 4.3 mmol) was dissolved in $CH_2Cl_2$ (5 mL) and cooled to 0° C. Then TFA (5 mL) was added and the reaction stirred under a drying tube for 2 hours. The reaction mixture was concentrated and azeotroped with benzene twice. The residue was dissolved in $CH_2Cl_2$ and poured into saturated $NaHCO_3$. The layers were separated and the aqueous layer was extracted with $CH_2Cl_2$. The combined organic layers were dried with sodium sulfate and concentrated to a pale yellow oil weighing 1.43 g, 97%. $^1H$ NMR ($CDCl_3$) δ 8.21 (s, 1H), 4.21 (t, 1H, J=5), 4.04 (d, 1H, J=5), 3.92 (s, 3H), 3.74 (d, 1H, J=3), 2.23 (s, 2H), 1.02 (m, 21H). $^{13}C$ NMR ($CDCl_3$) δ 165.7, 160.8, 143.1, 132.3, 65.5, 55.6, 51.5, 16.9, 10.9. IR (thin film, NaCl) 3376, 3315, 3168, 2944, 2893, 2866, 2762, 2726, 2625, 2247, 1744, 1673, 1583, 1514, 1463, 1439, 1384, 1367, 1345, 1323, 1203, 1110, 1069, 998, 918, 883, 841, 803, 769, 733, 683, 660, 647 $cm^{-1}$.

EXAMPLE 7

Synthesis of Ethylamine Teroxazole Intermediate 409

An ethylamine teroxazole intermediate that can be used to prepare compounds of the invention can be prepared as follows.

a. Synthesis of Compound 401

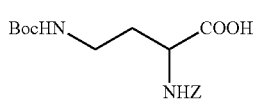

To a suspension of Z-L-2,4-diamino butyric acid (5.0 g, 19.8 mmol) in a mixture of THF/water (100 mL, 1:1) was added sodium bicarbonate (3.3 g, 39.6 mmol, 2.0 equiv.) and stirred for 15 min. Then a solution of $Boc_2O$ (9.9 g, 45.5 mmol, 2.3 equiv.) in THF (50 mL) was added and stirred at room temperature for overnight. Reaction mixture was concentrated and pH was adjusted with 2N HCl to pH ~2. It was extracted with ethyl acetate, dried ($Na_2SO_4$), filtered and concentrated to clear oil. The oily residue was placed on Kugelrohr to remove excess of $Boc_2O$ at 85° C. for 2 h to get thick clear oil weighing 6.5 g (93%); $^1H$ NMR ($CD_3OD$) δ 7.31 (m, 5H), 5.09 (s, 2H), 4.20 (dd, 1H, J=9.2, 4.4), 3.12 (m, 2H), 2.02 (m, 1H), 1.78 (m, 1H), 1.42 (s, 9H); $^{13}C$ NMR ($CD_3OD$) δ 174.3, 157.3, 157.1, 136.8, 128.1, 127.6, 127.4, 78.8, 66.3, 51.7, 36.7, 31.6, 27.4.

b. Synthesis of Compound 402

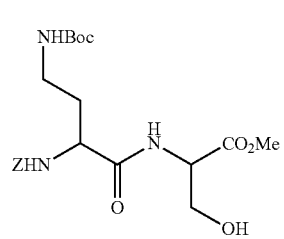

A mixture of Z-dab(Boc)-OH (401, 6.3 g, 17.9 mmol), (DL)-serine methyl ester hydrochloride (2.8 g, 17.9 mmol) and BOP (8.7 g, 19.7 mmol, 1.1 equiv.) was dissolved in DMF (50 mL) and stirred with diisopropyl ethylamine (6.8 mL, 39.4 mmol, 2.2 equiv.) at room temperature for 8 h. Reaction mixture was concentrated on Kugelrohr, diluted with ethyl acetate (250 mL) and washed with 20% aqueous Citric acid (80 mL), saturated sodium bicarbonate solution (100 mL) and brine (100 mL) Organic layer was dried ($Na_2SO_4$), filtered and concentrated to get a foam like sticky compound weighing 8.0 g (99%); $^1H$ NMR ($CD_3OD$) δ 7.34 (m, 5H), 6.54 (m, 1H), 5.10 (s, 2H), 4.51 (m, 1H), 4.23 (m, 1H), 3.88 (m, 2H), 3.72 (s, 3H), 3.17 (m, 2H), 1.98 (m, 1H), 1.79 (m, 1H), 1.43 (s, 9H); $^{13}C$ NMR ($CD_3OD$) δ 173.1, 170.7, 157.1, 136.7, 128.1, 127.6, 127.4, 78.8, 66.4, 61.3, 54.8, 52.8, 51.8, 36.6, 32.3, 27.4.

c. Synthesis of Compound 403

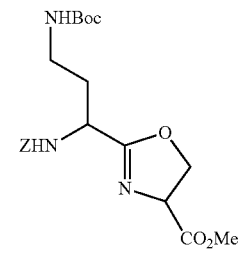

Compound 402 (8.0 g, 17.6 mmol) was dissolved in anhydrous $CH_2Cl_2$ (30 mL) and placed under nitrogen. After cooling to −78° C., DAST (3.47 mL, 26.5 mmol, 1.5 equiv.) was added over a period of 30 min and stirred at the same temperature for 4 h. Then solid $K_2CO_3$ (3.65 g, 26.5 mmol, 1.5 equiv.) was added and stirred for 1 h, and the reaction mixture was poured into saturated sodium bicarbonate solution. Aqueous layer was extracted with $CH_2Cl_2$ (2*100 mL) and the combined organic layers were dried over $Na_2SO_4$, filtered and concentrated to get an oily compound weighing 7.60 g (99%); $^1H$ NMR ($CDCl_3$) δ 7.21 (m, 5H), 6.16 (m, 1H), 5.29 (m, 1H), 4.98 (s, 2H), 4.60 (m, 1H), 4.35 (m, 3H), 3.62 (s, 3H), 3.16 (m, 2H), 1.91 (m, 1H), 1.74 (m, 1H), 1.32 (s, 9H); $^{13}C$ NMR ($CDCl_3$) δ 170.3, 169.0, 155.2, 154.9, 135.3, 127.5, 127.1, 127.0, 77.9, 69.3, 66.7, 65.9, 51.6, 46.3, 35.5, 32.3, 27.4.

d. Synthesis of Compound 404

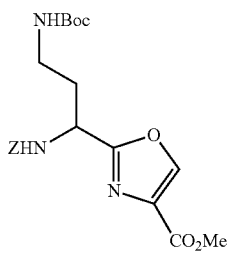

404

A solution of 403 (7.82 g, 17.9 mmol) in anhydrous CH$_2$Cl$_2$ (50 mL) under nitrogen atmosphere was cooled to −5° C. and DBU (5.38 mL, 35.9 mmol, 2.0 equiv.) followed by BrCCl$_3$ (4.25 mL, 43.1 mmol, 2.4 equiv.) was added over a period of 1 h using syringe pump. The reaction mixture was turned from orange to dark brown in color and was allowed to warm to room temperature overnight. Reaction mixture was diluted with saturated sodium bicarbonate solution and CH$_2$Cl$_2$ was removed under reduced pressure. Aqueous layer was extracted with ethyl acetate, dried over Na$_2$SO$_4$, filtered and concentrated to a brown residue. The residue was purified by flash chromatography eluting with 45% ethyl acetate/hexane get an amber oil weighing 5.44 g (70%); mp 113-115° C.; $^1$H NMR (CDCl$_3$) δ 8.07 (s, 1H), 7.19 (s, 5H), 6.36 (d, 1H, J=7.8), 5.18 (m, 1H), 4.97 (m, 3H), 3.74 (s, 3H), 3.20 (m, 1H), 3.03 (m, 1H), 1.99 (m, 2H), 1.29 (s, 9H); $^{13}$C NMR (CDCl$_3$) δ 163.8, 160.4, 155.3, 155.1, 143.3, 135.2, 132.1, 127.5, 127.1, 127.0, 78.2, 66.1, 51.1, 46.3, 35.7, 32.9, 27.4.

e. Synthesis of Compound 405

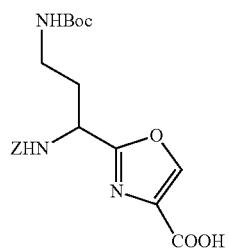

405

Compound 404 (5.4 g, 12.5 mmol) was dissolved in a 3:1 mixture of THF/water (40 mL) and cooled to 0° C. To this LiOH (628 mg, 14.9 mmol, 1.2 equiv.) was added and stirred at room temperature for 3 h. Reaction mixture was concentrated to remove THF and diluted with ether. Ether layer was decanted, and the aqueous layer was acidified with 2N HCl (~pH 2) and extracted with ethyl acetate. Organic layer was washed with water, dried over Na$_2$SO$_4$, filtered and concentrated to get a white solid weighing 4.96 g (95%); mp 52-53° C.; $^1$H NMR (CDCl$_3$) δ 9.01 (s, 1H), 8.13 (s, 1H), 7.26 (s, 5H), 6.48 (d, 1H, J=8.4), 5.05 (m, 4H), 3.13 (m, 2H), 2.12 (m, 2H), 1.38 (s, 9H); $^{13}$C NMR (CDCl$_3$) δ 164.3, 162.4, 155.4, 143.9, 135.1, 132.3, 127.5, 127.2, 127.1, 78.8, 66.3, 46.4, 35.7, 33.2, 27.4.

f. Synthesis of 406

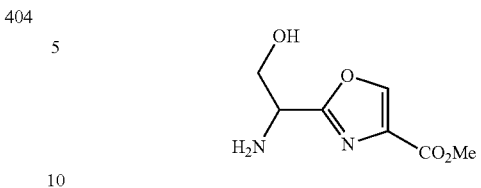

406

Compound 204 (5.5 g, 19.9 mmol) was dissolved in EtOH/THF (3:1, 300 mL) and added TFA (6.14 mL, 79.7 mmol, 4.0 equiv.) followed by Pd(OH)$_2$ (2.0 g) and stirred at room temperature under hydrogen atmosphere for 24 h. Reaction mixture was filtered through celite and the filtrate was concentrated under vacuum. The residue was further dried under high vacuum to get sticky brown solid weighing 3.6 g (97%); $^1$H NMR (CD$_3$OD) δ 8.65 (s, 1H), 4.73 (t, 1H, J=4.8), 4.07 (d, 2H, J=4.6), 3.89 (s, 3H); $^{13}$C NMR (CD$_3$OD) δ 161.6, 159.3, 146.1, 133.0, 60.0, 51.6, 50.5.

g. Synthesis of Compound 407

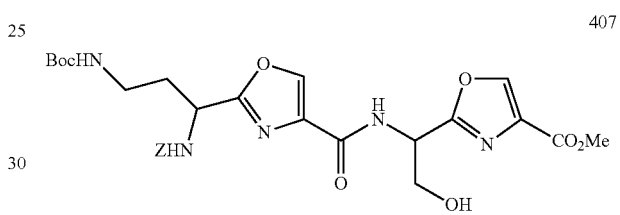

407

To a solution of 406 (2.2 g, 11.8 mmol) and 2,6-lutidine (6.85 mL, 59.0 mmol, 5.0 equiv.) in DMF (25 mL) at 0° C. under nitrogen atmosphere, a solution of 405 (4.95 g, 11.8 mmol), HOBT (3.21 g, 23.6 mmol, 2.0 equiv.), EDC (4.53 g, 23.6 mmol, 2.0 equiv.) in DMF (45 mL) was added and stirred at room temperature for 16 h. Reaction mixture was concentrated on Kugelrohr, diluted with 20% citric acid (100 mL) and extracted with ethyl acetate (200 mL) Organic layer was washed with saturated sodium bicarbonate solution (3*100 mL), brine (100 mL), dried over Na$_2$SO$_4$, filtered and concentrated to get a brown solid weighing 6.83 g (98%); $^1$H NMR (CD$_3$OD) δ 8.53 (s, 1H), 8.34 (s, 1H), 7.32 (s, 5H), 6.60 (m, 1H), 5.36 (t, 1H, J=5.3), 5.10 (s, 2H), 4.90 (m, 1H), 4.05 (d, 2H, J=5.6), 3.86 (s, 3H), 3.16 (m, 2H), 2.12 (m, 2H), 1.41 (s, 9H); $^{13}$C NMR (CD$_3$OD) δ 164.3, 163.2, 161.6, 161.2, 156.9, 145.1, 142.3, 136.6, 135.4, 132.8, 128.2, 127.8, 127.6, 78.8, 66.6, 61.9, 60.2, 51.4, 49.6, 36.7, 32.8, 27.6.

g. Synthesis of Compound 408

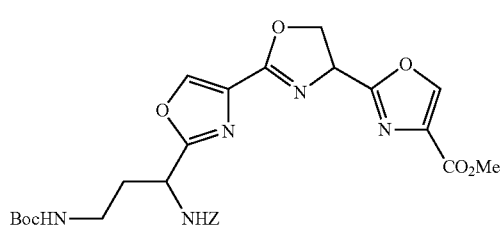

408

Compound 407 (6.83 g, 11.6 mmol) was dissolved in anhydrous CH$_2$Cl$_2$ (60 mL) and placed under nitrogen. After cooling to −78° C., DAST (2.28 ml, 17.4 mmol, 1.5 equiv.) was added over a period of 30 min and stirred at the same temperature for 4 h. Then solid $K_2CO_3$ (2.40 g, 17.4 mol, 1.5 equiv.) was added and stirred for 1 h, and the reaction mixture was poured into saturated sodium bicarbonate solution. Aqueous layer was extracted with $CH_2Cl_2$ and the combined organic layers were dried over $Na_2SO_4$, filtered and concentrated to get an oily compound weighing 6.1 g (92%); $^1H$ NMR (CDCl$_3$) δ 8.15 (s, 1H), 8.02 (s, 1H), 7.26 (s, 5H), 5.69 (m, 1H), 5.47 (m, 1H), 4.99 (m, 4H), 4.72 (m, 2H), 3.84 (s, 3H), 3.24 (m, 1H), 3.04 (m, 1H), 2.12 (m, 1H), 1.88 (m, 1H), 1.34 (s, 9H).

h. Synthesis of Compound 409

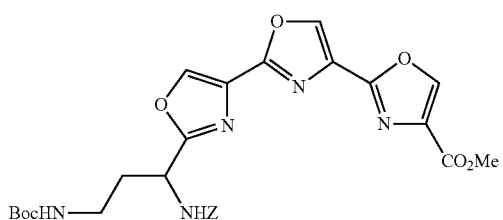

409

A solution of 408 (6.1 g, 10.7 mmol) in anhydrous $CH_2Cl_2$ (50 mL) under nitrogen atmosphere was cooled to −5° C. and DBU (3.2 mL, 21.4 mmol, 2.0 equiv.) followed by BrCCl$_3$ (2.5 mL, 25.7 mmol, 2.4 equiv.) was added over a period of 0.5 h using syringe pump. The reaction mixture was turned from orange to dark brown in color and started precipitating out. To this, anhydrous $CH_2Cl_2$ (100 mL) was added and allowed to warm to room temperature overnight. Reaction mixture was diluted with saturated sodium bicarbonate solution and $CH_2Cl_2$ was removed under reduced pressure. Aqueous layer was extracted with chloroform, dried over $Na_2SO_4$, filtered and concentrated to a brown residue.

EXAMPLE 8

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula (I):

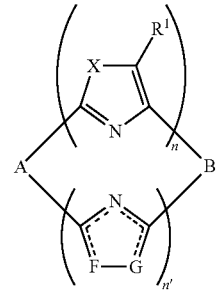

(I)

wherein:
one of A and B is —CH($R^b$)CH($R^c$)C($R^d$)($R^e$)—; and the other of A and B is:

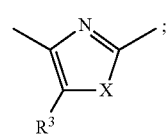

—CH(R$^a$)NHC(=O)— or —CH(R$^{b1}$)CH(R$^{c1}$)C(R$^{d1}$)(R$^{e1}$)—;

one of F and G is X and the other is C(R$^2$);

each X is independently NH, S, or O;

the dotted line in the ring containing F and G signifies that two double bonds are present in the ring, the positions of which depend upon the values selected for F and G;

n and n' each independently represents 1, 2, 3, 4 and 5, provided that the sum of n and n' is 6;

R$^a$ represents hydrogen, (C$_1$-C$_6$)alkyl, (C$_2$-C$_6$)alkenyl, (C$_1$-C$_6$)alkoxy or (C$_1$-C$_6$)alkanoyloxy, wherein each (C$_1$-C$_6$)alkyl, (C$_2$-C$_6$)alkenyl, (C$_1$-C$_6$)alkoxy and (C$_1$-C$_6$)alkanoyloxy is optionally substituted with OH, (C$_1$-C$_6$)alkoxy, (C$_1$-C$_6$)alkylthio, aryl, heteroaryl, NR$^f$R$^g$, or —C(=O)NR$^f$R$^g$; and wherein each aryl and heteroaryl is optionally substituted with one or two substituents selected independently from halo, hydroxy, (C$_1$-C$_6$)alkyl, NR$^f$R$^g$, and NR$^f$R$^g$(C$_1$-C$_6$)alkyl- R$^b$ and R$^c$ each represents hydrogen, or R$^b$ and R$^c$ together represent a bond or —O—;

R$^d$ and R$^e$ together represent (=O) or R$^d$ represents hydrogen and R$^e$ represents hydrogen, hydroxy, (C$_1$-C$_6$)alkanoyloxy, NR$^j$R$^k$, CH$_2$C(=O)OR$^s$ or CH$_2$C(=O)NR$^m$R$^n$, wherein each (C$_1$-C$_6$)alkanoyloxy is optionally substituted with one or more NR$^t$R$^u$;

R$^{b1}$ and R$^{c1}$ each represents hydrogen, or R$^{b1}$ and R$^{c1}$ together represent a bond or —O—;

R$^{d1}$ and R$^{e1}$ together represent (=O) or R$^{d1}$ represents hydrogen and R$^{e1}$ represents hydrogen, hydroxy, (C$_1$-C$_6$)alkanoyloxy, NR$^j$R$^k$, CH$_2$C(=O)OR$^s$ or CH$_2$C(=O)NR$^m$R$^n$, wherein each (C$_1$-C$_6$)alkanoyloxy is optionally substituted with one or more NR$^t$R$^u$;

each of R$^f$ and R$^g$ is independently hydrogen, (C$_1$-C$_6$)alkyl or (C$_1$-C$_6$)alkanoyl, which (C$_1$-C$_6$)alkyl is optionally substituted with one or more NR$^t$R$^u$; or R$^f$ and R$^g$ together with the nitrogen to which they are attached form a pyrrolidino, piperidino, piperazino, morpholino, thiomorpholino, or azepino ring;

each of R$^j$ and R$^k$ is independently hydrogen or (C$_1$-C$_6$)alkyl, which (C$_1$-C$_6$)alkyl is optionally substituted with one or more NR$^t$R$^u$; or R$^j$ and R$^k$ together with the nitrogen to which they are attached form a pyrrolidino, piperidino, piperazino, morpholino, thiomorpholino, or azepino ring;

each of R$^m$ and R$^n$ is independently hydrogen or (C$_1$-C$_6$)alkyl, which (C$_1$-C$_6$)alkyl is optionally substituted with one or more NR$^t$R$^u$; or R$^m$ and R$^n$ together with the nitrogen to which they are attached form a pyrrolidino, piperidino, piperazino, morpholino, thiomorpholino, or azepino ring;

each of R$^1$, R$^2$, and R$^3$ is independently hydrogen (C$_1$-C$_6$)alkyl, (C$_1$-C$_6$)alkoxy, aryl or heteroaryl wherein each (C$_1$-C$_6$)alkyl and (C$_1$-C$_6$)alkoxy is optionally substituted with OH, (C$_1$-C$_6$)alkoxy, (C$_1$-C$_6$)alkylthio, aryl, NR$^o$R$^p$, or —C(=O)NR$^q$R$^r$; and wherein each aryl or heteroaryl is optionally substituted with one or two substituents selected independently from a halogen atom and (C$_1$-C$_4$)alkyl wherein (C$_1$-C$_4$)alkyl is optionally substituted with NR$^o$R$^p$;

each of R$^o$ and R$^p$ is independently hydrogen or (C$_1$-C$_6$)alkyl, which (C$_1$-C$_6$)alkyl is optionally substituted with one or more NR$^t$R$^u$; or R$^o$ and R$^p$ together with the nitrogen to which they are attached form a pyrrolidino, piperidino, piperazino, morpholino, thiomorpholino, or azepino ring; and each of R$^q$ and R$^r$ is independently hydrogen or (C$_1$-C$_6$)alkyl, which (C$_1$-C$_6$)alkyl is optionally substituted with one or more NR$^t$R$^u$; or R$^q$ and R$^r$ together with the nitrogen to which they are attached form a pyrrolidino, piperidino, piperazino, morpholino, thiomorpholino, or azepino ring;

R$^s$ is hydrogen or (C$_1$-C$_6$)alkyl, which (C$_1$-C$_6$)alkyl is optionally substituted with one or more NR$^t$R$^u$;

each of R$^t$ and R$^u$ is independently hydrogen, (C$_1$-C$_6$)alky or (C$_1$-C$_6$)alkanoyl; or R$^t$ and R$^u$ together with the nitrogen to which they are attached form a pyrrolidino, piperidino, piperazino, morpholino, thiomorpholino, or azepino ring;

or a salt thereof.

2. The compound of claim 1 wherein:

one of A and B is —CH(R$^b$)CH(R$^c$)C(R$^d$)(R$^e$)—;

and the other of A and B is:

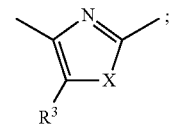

—CH(R$^a$)NHC(=O)— or —CH(R$^{b1}$)CH(R$^{c1}$)C(R$^{d1}$)(R$^{e1}$)—;

one of F and G is X and the other is C(R$^2$);

each X is independently NH, S, or O;

the dotted line in the ring containing F and G signifies that two double bonds are present in the ring, the positions of which depend upon the values selected for F and G;

n and n' each independently represents 1, 2, 3, 4 and 5, provided that the sum of n and n' is 6;

R$^a$ represents hydrogen, (C$_1$-C$_6$)alkyl, (C$_1$-C$_6$)alkoxy or (C$_1$-C$_6$)alkanoyloxy, wherein each (C$_1$-C$_6$)alkyl, (C$_1$-C$_6$)alkoxy and (C$_1$-C$_6$)alkanoyloxy, is optionally substituted with OH, (C$_1$-C$_6$)alkoxy, (C$_1$-C$_6$)alkylthio, aryl, heteroaryl, NR$^f$R$^g$ or —C(=O)NR$^f$R$^g$; and wherein each aryl and heteroaryl is optionally substituted with one or two substituents selected independently from halo, (C$_1$-C$_6$)alkyl, NR$^f$R$^g$ and NR$^f$R$^g$(C$_1$-C$_6$)alkyl- R$^b$ and R$^c$ each represents hydrogen, or R$^b$ and R$^c$ together represent a bond or —O—;

R$^d$ and R$^e$ together represent (=O) or R$^d$ represents hydrogen and R$^e$ represents hydrogen, hydroxy, (C$_1$-C$_6$)alkanoyloxy, NR$^j$R$^k$, CH$_2$C(=O)OR$^s$ or CH$_2$C(=O)NR$^m$R$^n$, wherein each (C$_1$-C$_6$)alkanoyloxy is optionally substituted with one or more NR$^t$R$^u$;

R$^{b1}$ and R$^{c1}$ each represents hydrogen, or R$^{b1}$ and R$^{c1}$ together represent a bond or —O—;

R$^{d1}$ and R$^{e1}$ together represent (=O) or R$^{d1}$ represents hydrogen and R$^{e1}$ represents hydrogen, hydroxy, (C$_1$-C$_6$)alkanoyloxy, NR$^j$R$^k$, CH$_2$C(=O)OR$^s$ or CH$_2$C(=O)NR$^m$R$^n$, wherein each (C$_1$-C$_6$)alkanoyloxy is optionally substituted with one or more NR$^t$R$^u$;

each of R$^f$ and R$^g$ is independently hydrogen or (C$_1$-C$_6$)alkyl, which (C$_1$-C$_6$)alkyl is optionally substituted with one or more NR$^t$R$^u$; or R$^f$ and R$^g$ together with the nitrogen to which they are attached form a pyrrolidino, piperidino, piperazino, morpholino, thiomorpholino, or azepino ring;

each of R$^j$ and R$^k$ is independently hydrogen or (C$_1$-C$_6$)alkyl, which (C$_1$-C$_6$)alkyl is optionally substituted with one or more NR$^t$R$^u$; or R$^j$ and R$^k$ together with the nitrogen to which they are attached form a pyrrolidino, piperidino, piperazino, morpholino, thiomorpholino, or azepino ring;

each of $R^m$ and $R^n$ is independently hydrogen or $(C_1$-$C_6)$ alkyl, which $(C_1$-$C_6)$alkyl is optionally substituted with one or more $NR^tR^u$; or $R^m$ and $R^n$ together with the nitrogen to which they are attached form a pyrrolidino, piperidino, piperazino, morpholino, thiomorpholino, or azepino ring;

each of $R^1$, $R^2$, and $R^3$ is independently hydrogen, $(C_1$-$C_6)$alkyl, $(C_1$-$C_6)$alkoxy, aryl or heteroaryl wherein each $(C_1$-$C_6)$alkyl and $(C_1$-$C_6)$alkoxy is optionally substituted with OH, $(C_1$-$C_6)$alkoxy, $(C_1$-$C_6)$alkylthio, aryl, $NR^oR^p$, or —C(=O)$NR^qR^r$; and wherein each aryl or heteroaryl is optionally substituted with one or two substituents selected independently from a halogen atom and $(C_1$-$C_4)$alkyl wherein $(C_1$-$C_4)$alkyl is optionally substituted with $NR^oR^p$;

each of $R^o$ and $R^p$ is independently hydrogen or $(C_1$-$C_6)$ alkyl, which $(C_1$-$C_6)$alkyl is optionally substituted with one or more $NR^tR^u$; or $R^o$ and $R^p$ together with the nitrogen to which they are attached form a pyrrolidino, piperidino, piperazino, morpholino, thiomorpholino, or azepino ring; and each of $R^q$ and $R^r$ is independently hydrogen or $(C_1$-$C_6)$ alkyl, which $(C_1$-$C_6)$alkyl is optionally substituted with one or more $NR^tR^u$; or $R^q$ and $R^r$ together with the nitrogen to which they are attached form a pyrrolidino, piperidino, piperazino, morpholino, thiomorpholino, or azepino ring;

$R^s$ is hydrogen or $(C_1$-$C_6)$alkyl, which $(C_1$-$C_6)$alkyl is optionally substituted with one or more $NR^tR^u$;

each of $R^t$ and $R^u$ is independently hydrogen, $(C_1$-$C_6)$ alkyl or $(C_1$-$C_6)$alkanoyl, or $R^t$ and $R^u$ together with the nitrogen to which they are attached form a pyrrolidino, piperidino, piperazino, morpholino, thiomorpholino, or azepino ring.

3. A compound as claimed in claim 1, in which n and n' each represents 3.

4. A compound as claimed in claim 1, which is selected from formulae:

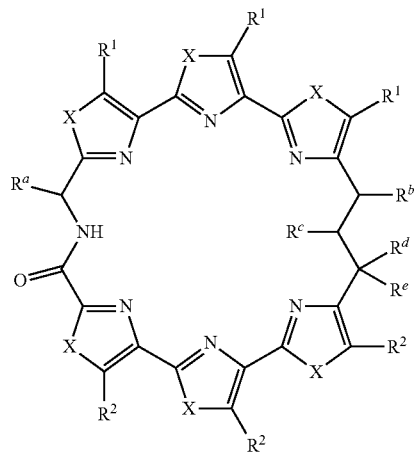

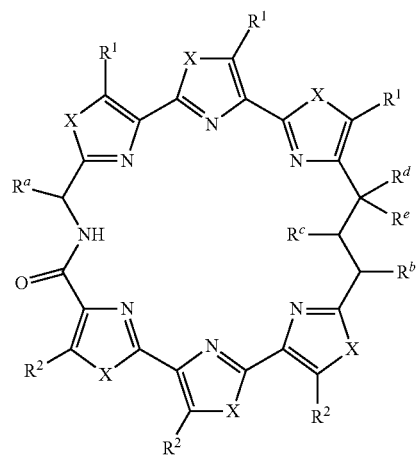

71
-continued
(Ic′)
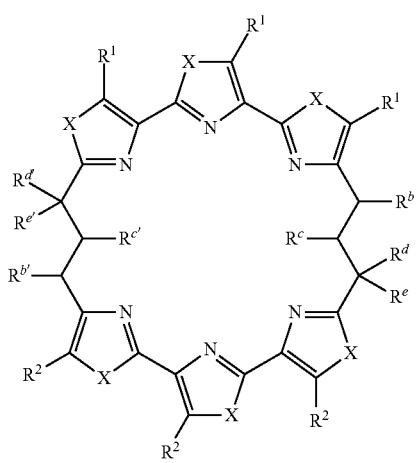
(Ic″)
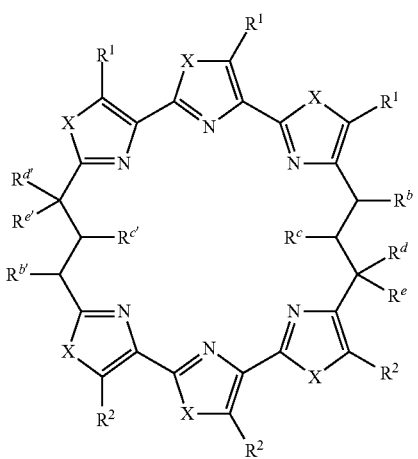
(Id′)
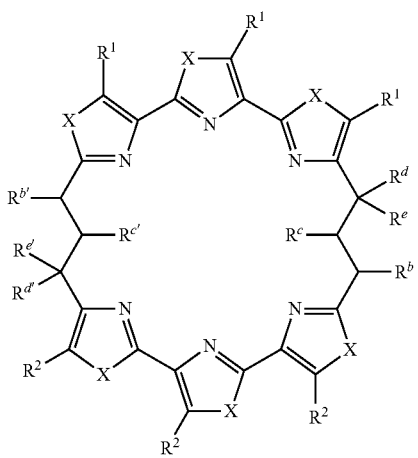
72
-continued
(Id″)
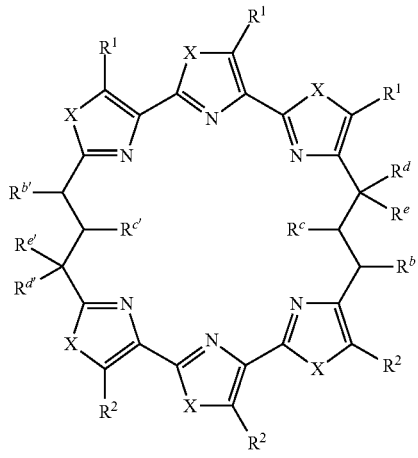
(Ie″)
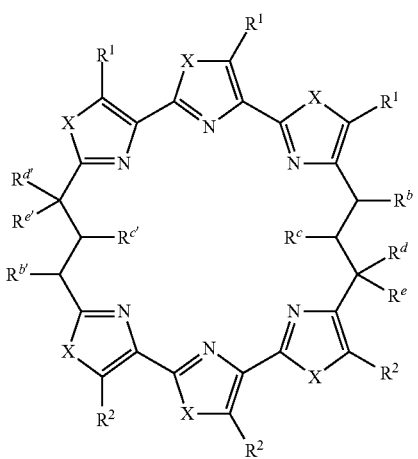
and
(If″)
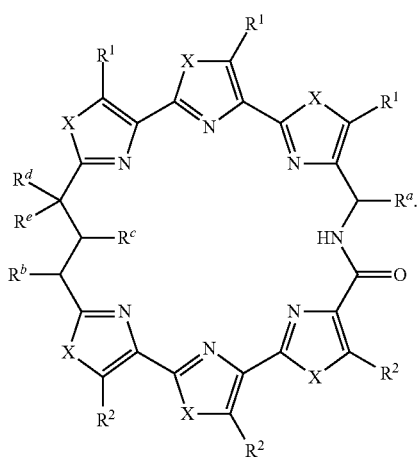

5. A compound as claimed in claim 1, which has formula (Ia'):

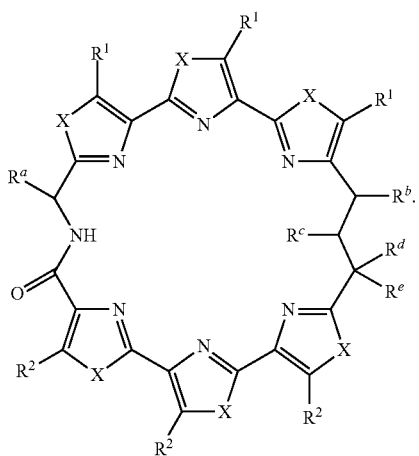

(Ia')

6. A compound as claimed in claim 1, which has formula (Ig'):

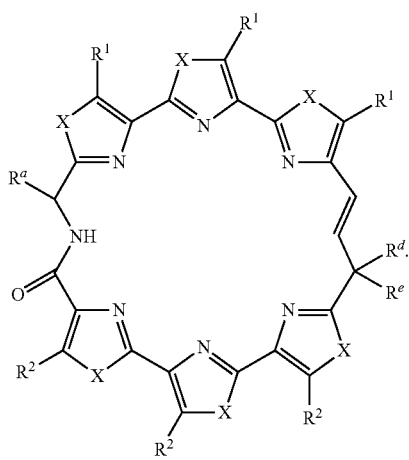

(Ig')

7. A compound as claimed in claim 1, which has formula (Ih'):

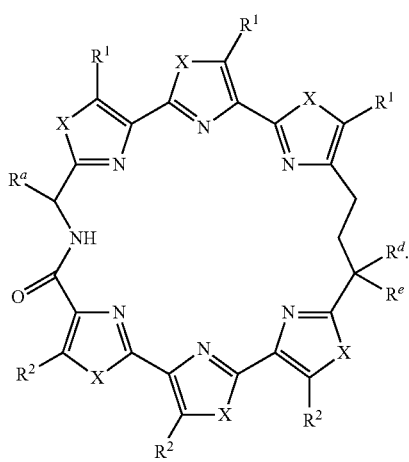

(Ih')

8. A compound as claimed in claim 1, in which each X is O.
9. A compound as claimed in claim 1, in which each $R^1$ is hydrogen.

10. A compound as claimed in claim 1, in which each $R^2$ is hydrogen.

11. A compound as claimed in claim 1, in which
$R^a$ is selected from hydrogen, methyl, isopropyl, 1-methylpropyl, 2-methylpropyl, benzyl, 4-hydroxybenzyl, 4-iodobenzyl, 4-aminobenzyl, and 4-(2-N,N-dimethylaminoethylamino)benzyl;
$R^b$ and $R^c$ are, together are a bond;
$R^d$ is hydrogen and
$R^e$ is hydrogen, hydroxy, $CH_2C(=O)OCH_3$, $CH_2C(=O)N(CH_3)_2$, or $CH_2C(=O)NHCH_2CH_2N(CH_3)_2$.

12. A compound as claimed in claim 1, in which
$R^{b\prime}$ and $R^{c\prime}$ together are a bond;
$R^{d\prime}$ is hydrogen; and
$R^{e\prime}$ is hydrogen, hydroxy, $CH_2C(=O)OCH_3$ or $CH_2C(=O)N(CH_3)_2$, or $CH_2C(=O)NHCH_2CH_2N(CH_3)_2$.

13. A compound as claimed in claim 1, in which $R^a$ is alkyl.

14. A compound as claimed in claim 1, in which $R^a$ is isopropyl.

15. A compound as claimed claim 1 in which $R^a$ is $(C_1$-$C_6)$ alkyl or $(C_2$-$C_6)$alkenyl wherein each $(C_1$-$C_6)$alkyl, and $(C_2$-$C_6)$alkenyl, is optionally substituted with $NR^fR^g$.

16. A compound as claimed in claim 1 in which $R^a$ is aminomethyl, 2-aminoethyl, 3-aminopropyl or 4-aminobutyl.

17. A compound as claimed in claim 1, in which $R^d$ and $R^e$ are hydrogen.

18. The compound of claim 1 which is

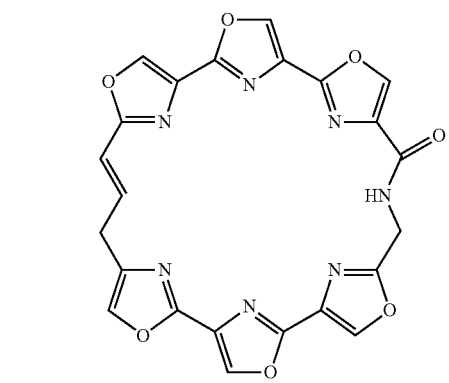

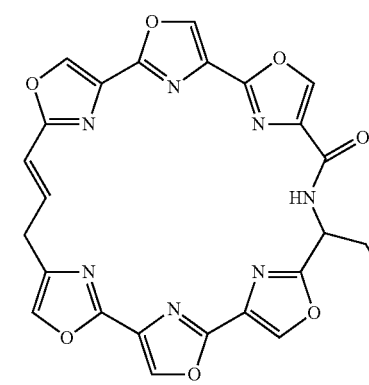

75
-continued
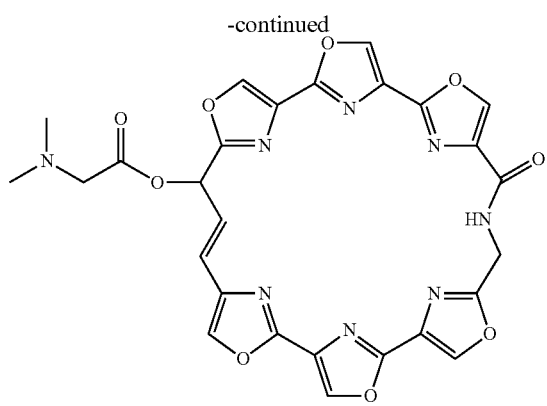
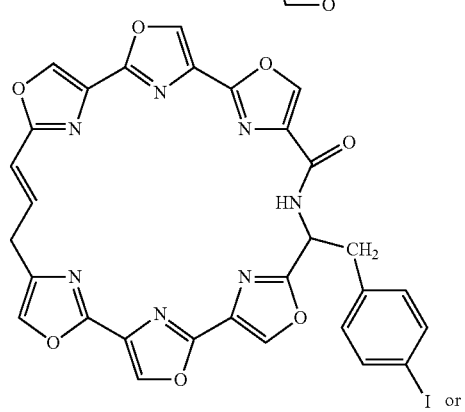
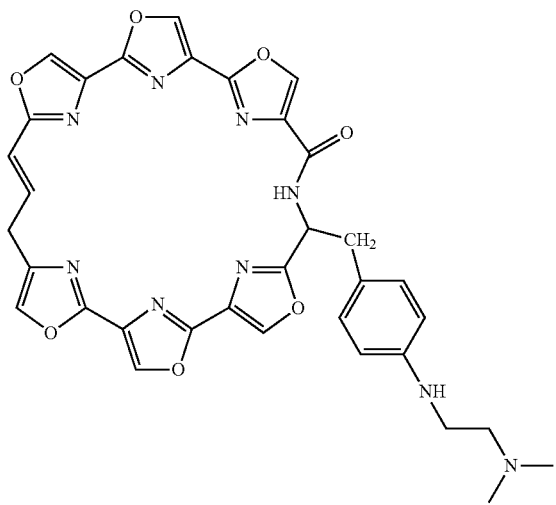 [SMILES: CN(C)CCNc1ccc(CC2NC(=O)c3coc(n3)-c3coc(n3)-c3coc(n3)/C=C/Cc3coc(n3)-c3coc(n3)-c3coc2n3)cc1]
or a salt thereof.
19. The compound of claim 1 which is,
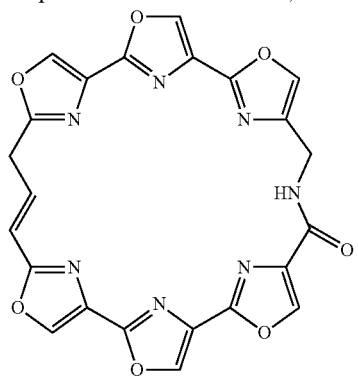
76
-continued
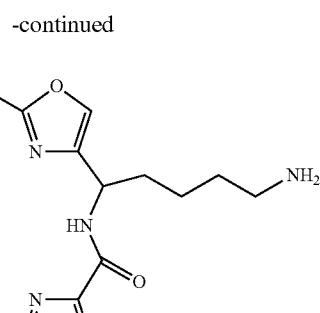
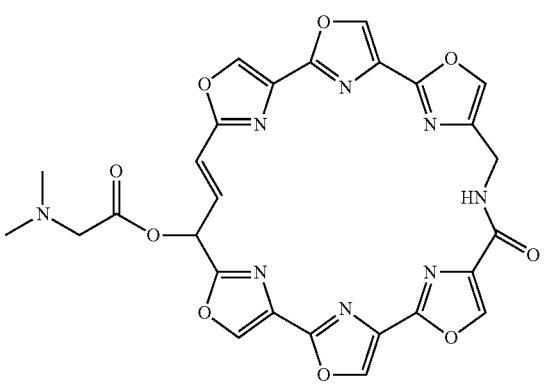
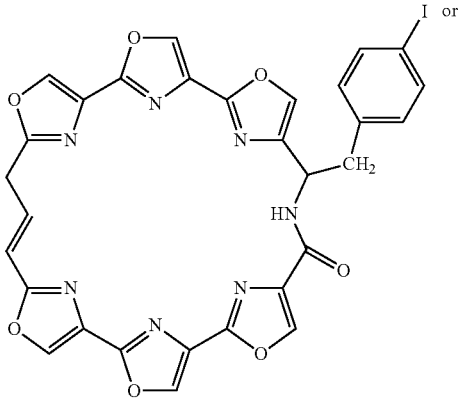
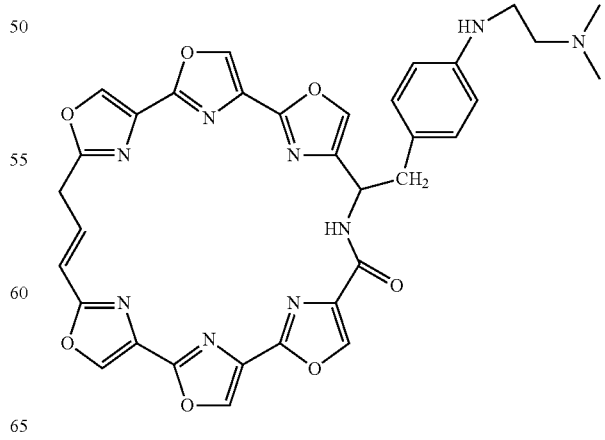
or a salt thereof.

20. The compound of claim 1 which is,

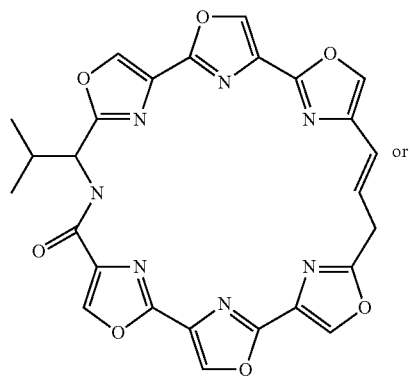 or 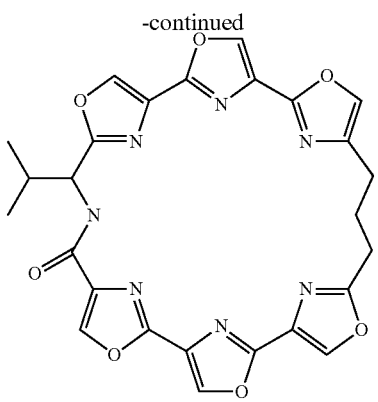

or a salt thereof.

21. A pharmaceutical composition comprising a compound of formula (I) as defined in claim 1; or a pharmaceutically acceptable salt thereof; and a pharmaceutically acceptable carrier.

22. A method to stabilize G-quadruplex DNA comprising contacting the G-quadruplex DNA with a compound of formula I as defined in claim 1, or a salt thereof.

* * * * *